United States Patent
Simmons et al.

(10) Patent No.: US 12,089,592 B1
(45) Date of Patent: Sep. 17, 2024

(54) POST-HARVEST LETTUCE TREATMENT METHODS

(71) Applicant: BioSure North America LLC, Fair Oaks Ranch, TX (US)

(72) Inventors: Darren Simmons, Fair Oaks Ranch, TX (US); Angelita Simmons, Fair Oaks Ranch, TX (US); Jeffrey R. Foote, Milton, GA (US); Christopher Salaski, Peachtree City, GA (US); Ivor J. J. Longo, Atlanta, TX (US); Wayne Simmons, Adkins, TX (US); H. Brock Kolls, Alpharetta, GA (US)

(73) Assignee: BioSure North America LLC, Fair Oaks Ranch, TX (US)

( * ) Notice: Subject to any disclaimer, the term of this patent is extended or adjusted under 35 U.S.C. 154(b) by 0 days.

(21) Appl. No.: 18/628,678

(22) Filed: Apr. 6, 2024

Related U.S. Application Data

(63) Continuation-in-part of application No. 18/428,523, filed on Jan. 31, 2024, and a continuation-in-part of application No. 18/528,162, filed on Dec. 4, 2023, now Pat. No. 11,975,118, and a continuation-in-part of application No. 18/528,194, filed on Dec. 4, 2023.

(51) Int. Cl.
| | |
|---|---|
| *A01N 59/00* | (2006.01) |
| *A01H 6/14* | (2018.01) |
| *A01N 3/00* | (2006.01) |
| *A01P 1/00* | (2006.01) |

(52) U.S. Cl.
CPC ............. *A01N 3/00* (2013.01); *A01H 6/1472* (2018.05); *A01N 59/00* (2013.01); *A01P 1/00* (2021.08)

(58) Field of Classification Search
CPC ........ A01N 3/00; A01N 59/00; A01H 6/1472; A01P 1/00
See application file for complete search history.

(56) References Cited

U.S. PATENT DOCUMENTS

2013/0028787 A1* 1/2013 Takeuchi ............... A01N 59/00
424/682

FOREIGN PATENT DOCUMENTS

WO    WO-2016072411 A1 * 5/2016 ............... A23B 7/00

\* cited by examiner

Primary Examiner — Sean E Conley
(74) Attorney, Agent, or Firm — H. Brock Kolls

(57) ABSTRACT

The present invention relates to post-harvest lettuce treatment methods that use aqueous ozone to disinfect, extend vitality, and reduce the amount of lettuce used in food preparation. The methods include steps such as creating an ozonated concentrate liquid by way of an aqueous ozone generator, removing pesticide residues from lettuce by a rinse in the ozonated concentrate liquid, disinfecting the lettuce by immersion in the ozonated concentrate liquid, oxygenating lettuce plant tissue to reinvigorate the lettuce, neutralizing the odor of the plant tissue by misting the ozonated concentrate liquid onto the plant tissue at a periodic mist interval, and other method steps and features including being able to disinfect and oxygenate lettuce in prepackaged produce packaging.

21 Claims, 33 Drawing Sheets

Post-Harvest Produce Treatment

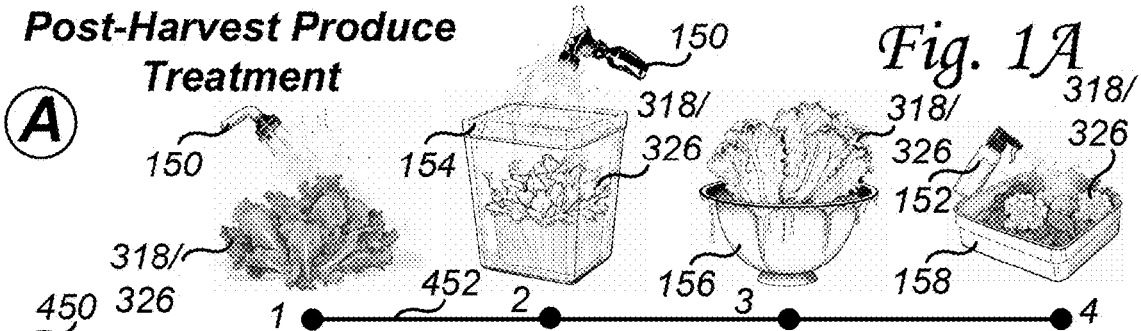

*Fig. 1A*

| O₃ Delivery | Spray | Immersion | Delay Drying | Mist |
|---|---|---|---|---|
| Action | Remove Pesticide Residuals | Disinfect | Oxygenate | Neutralize Odor |
| Duration | Seconds | < 1 Min | > 1 Min | Repeat > 1 Hr & Air Dry |
| Outcome | Produce Surface Decontamination And Pathogen Inactivation || Plant Tissue Cellular Revitalization ||

Food Preparation Disinfection Treatment

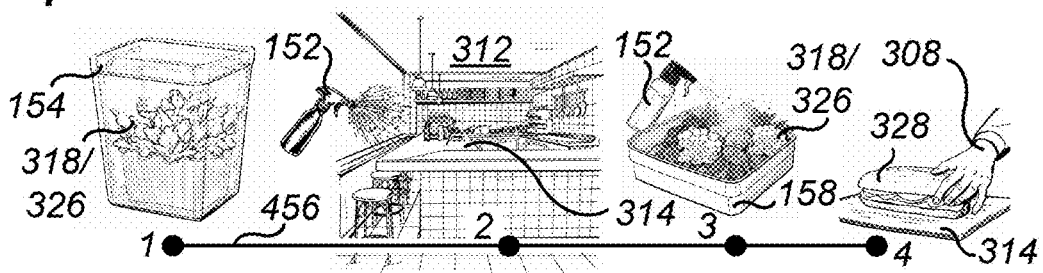

Prepare Food Item

| O₃ Delivery | Immersion | Mist | Mist | |
|---|---|---|---|---|
| Action | Disinfect (Produce) | Disinfect (Food Prep Areas) | Oxygenate & Neutralize Odor (Produce) | |
| Duration | < 1 Min | Wipe > 30 Sec Prefer Air Dry | Repeat > 1 Hr & Air Dry | 454 |
| Outcome | Produce/Prep Area Surfaces Decontamination And Pathogen Inactivation || Plant Tissue Cellular Revitalization | |

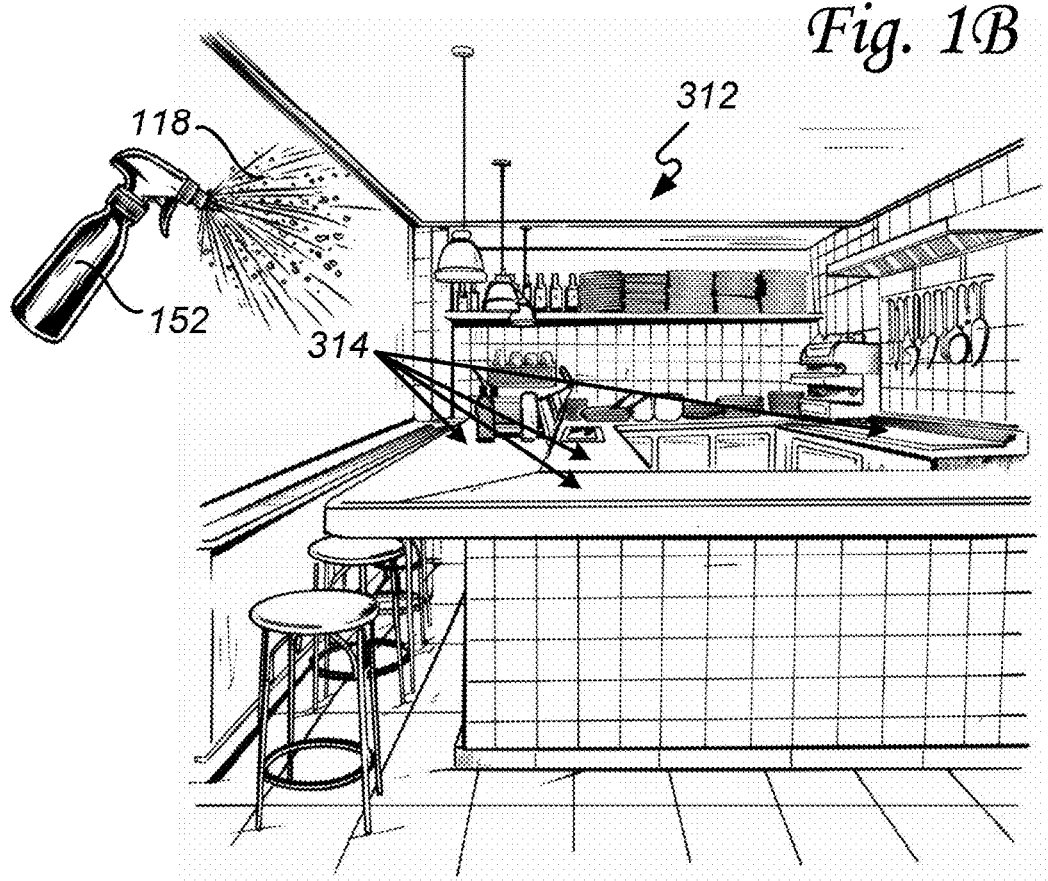
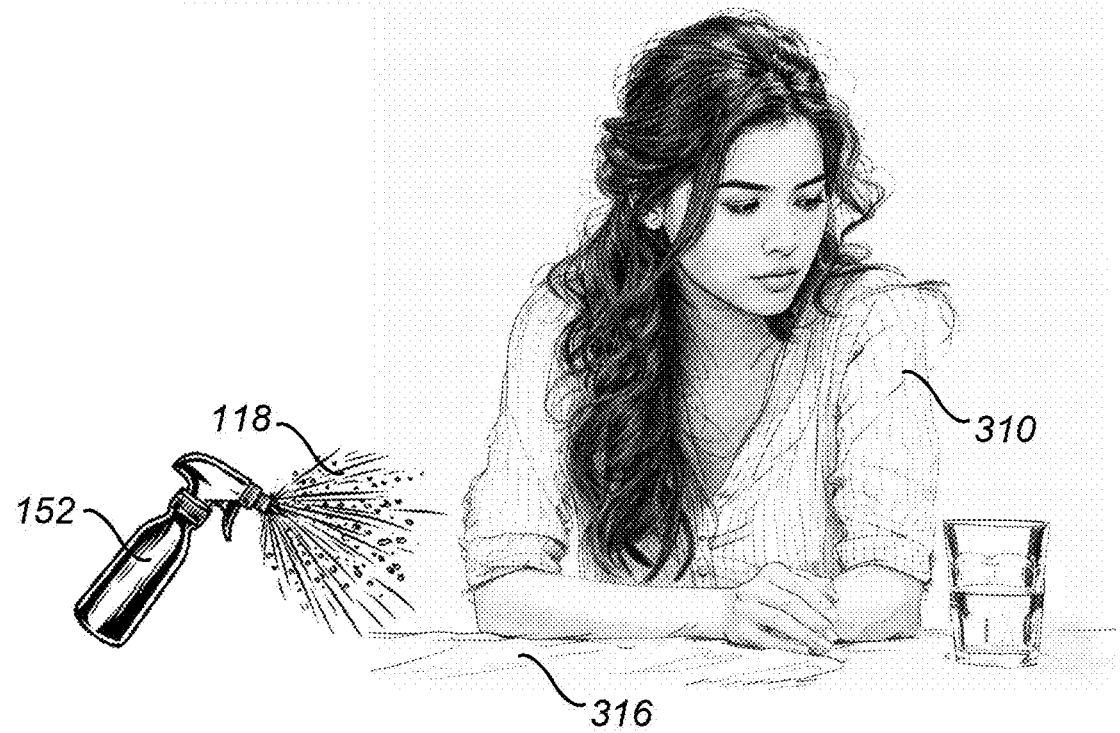
Fig. 1B

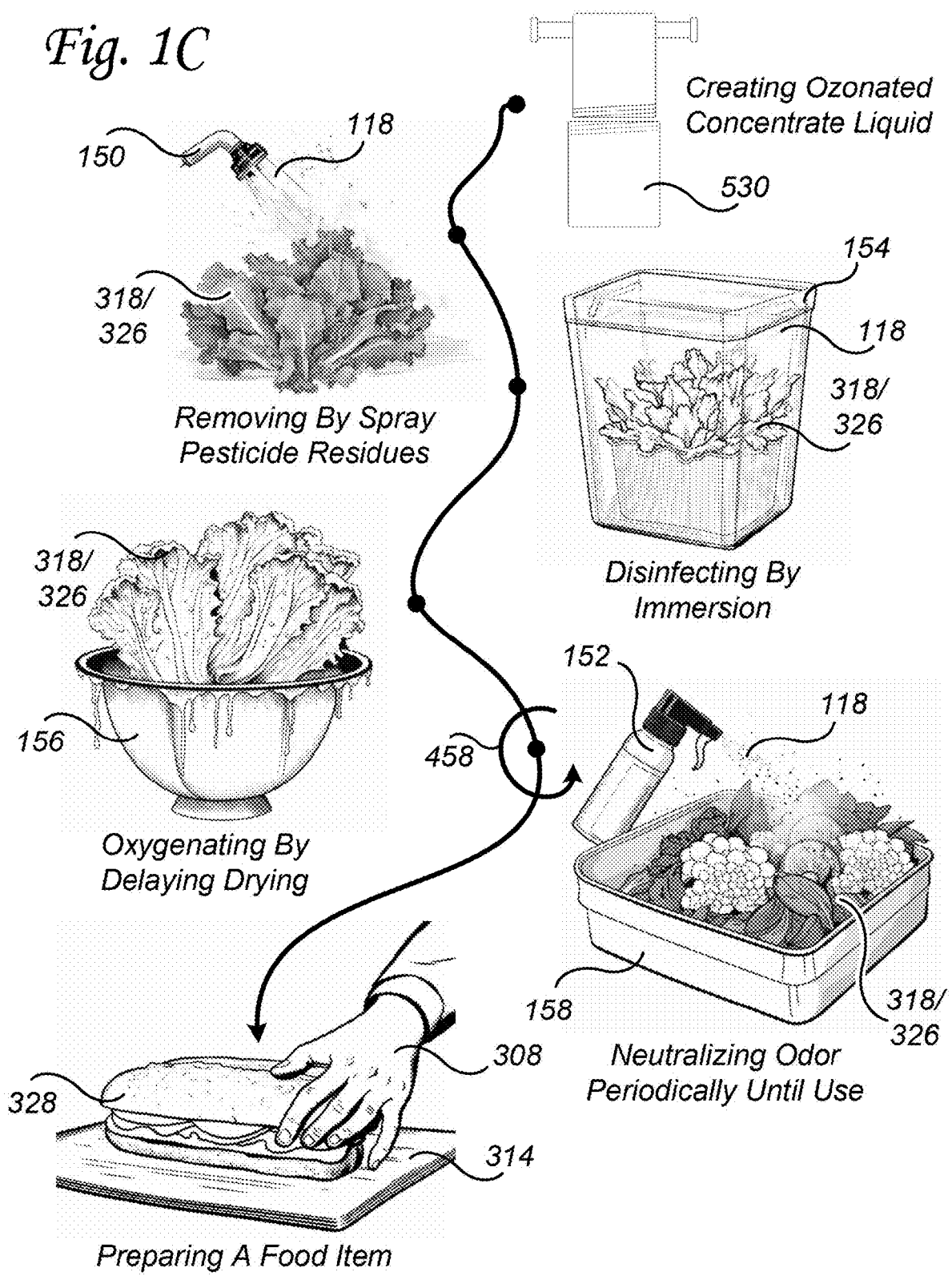

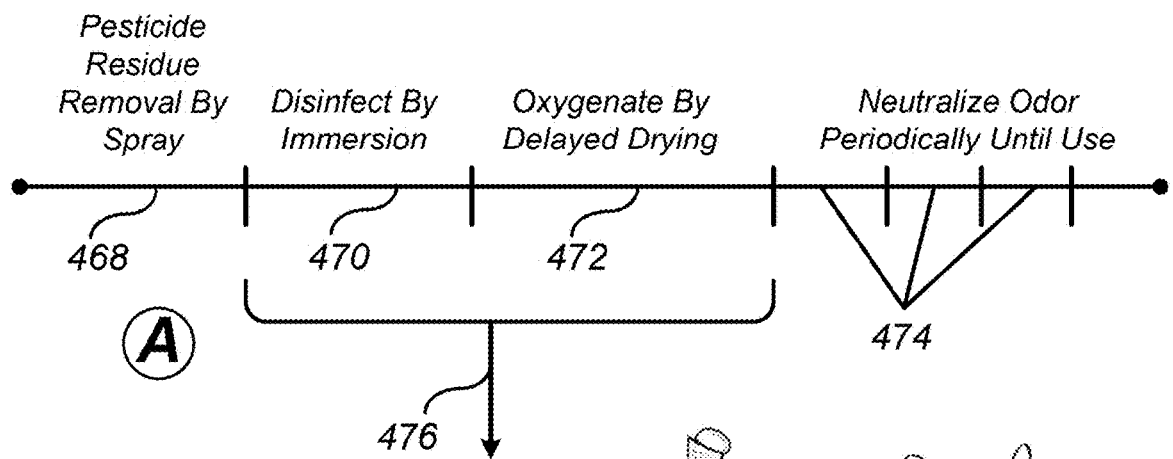
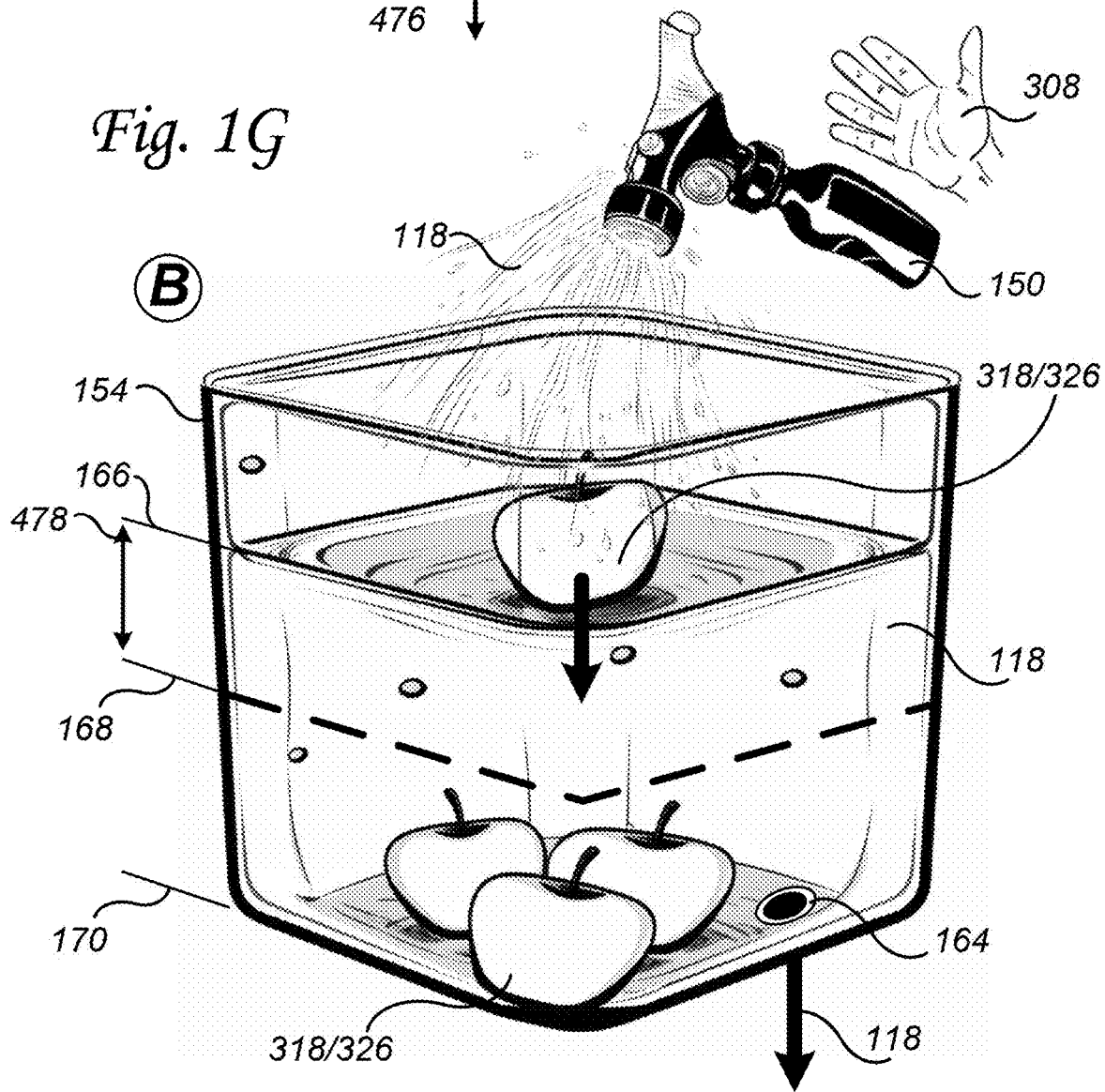
Fig. 1G

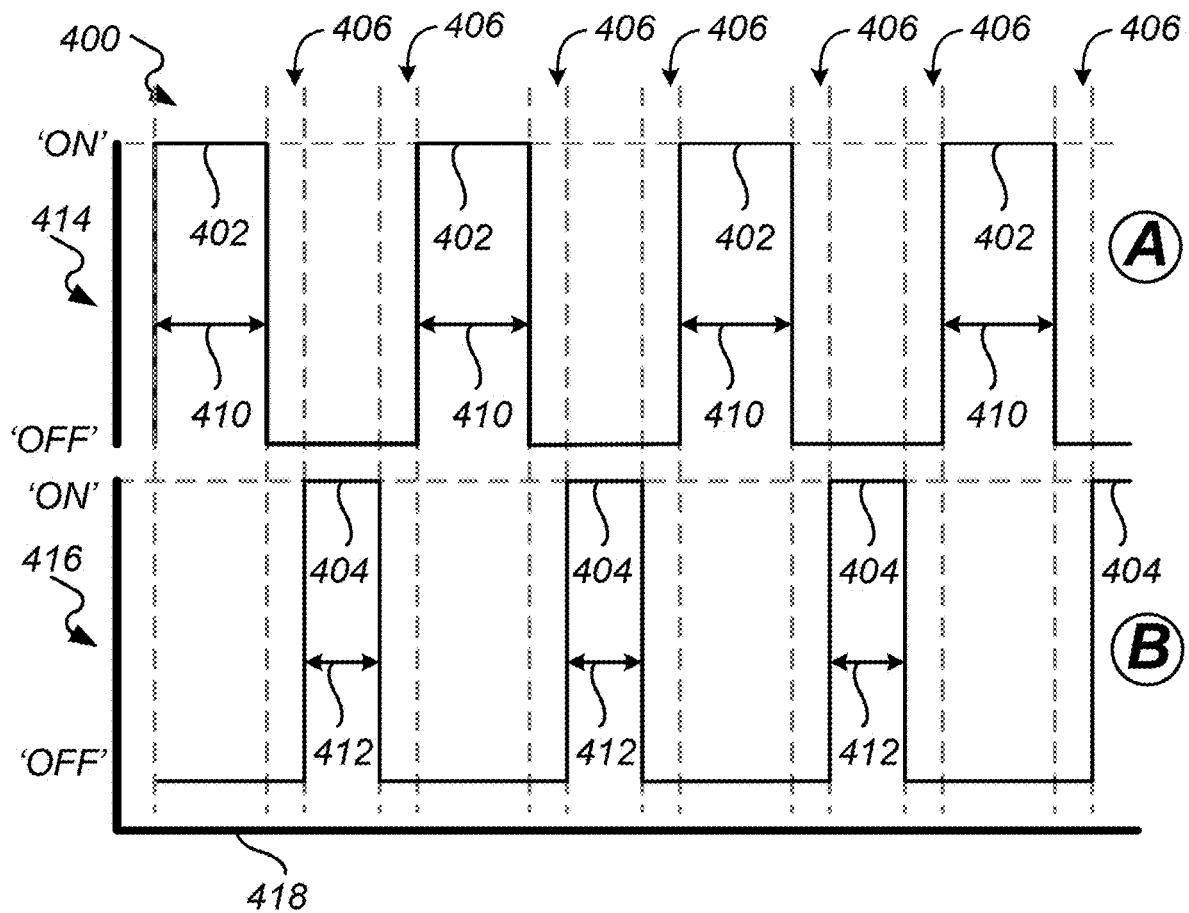
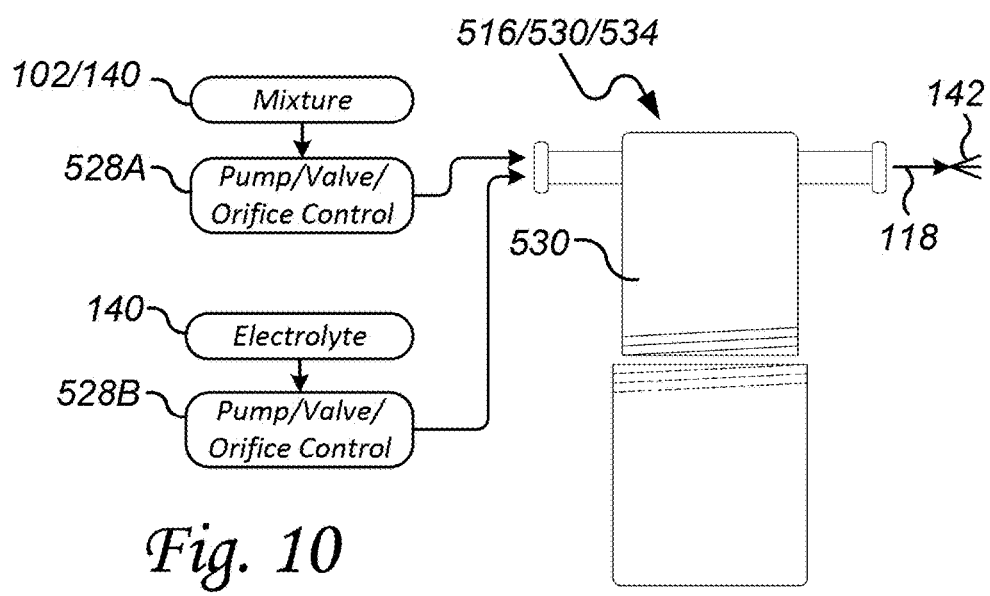
Fig. 10

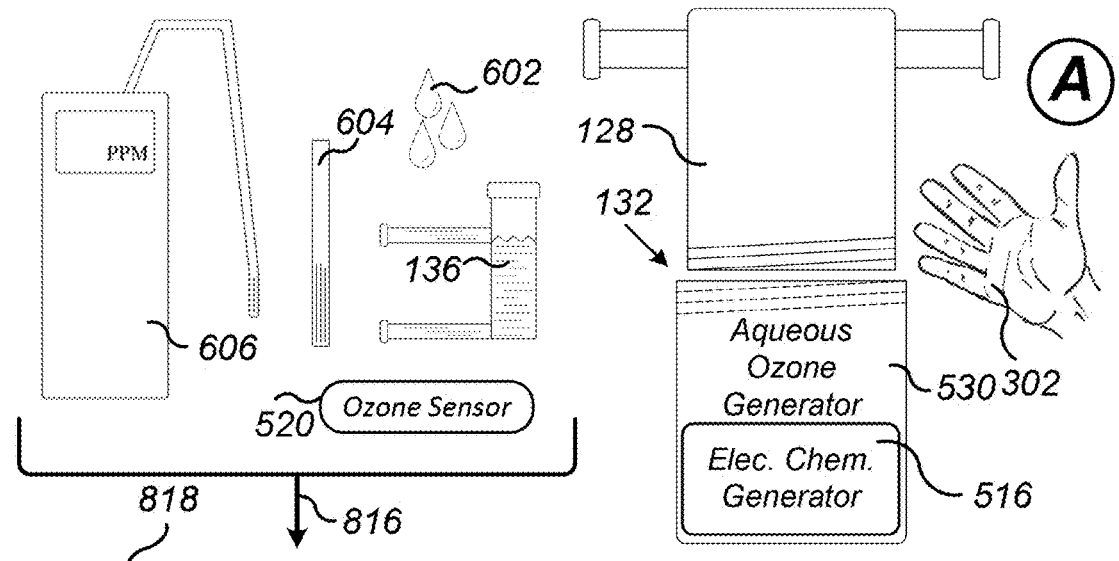
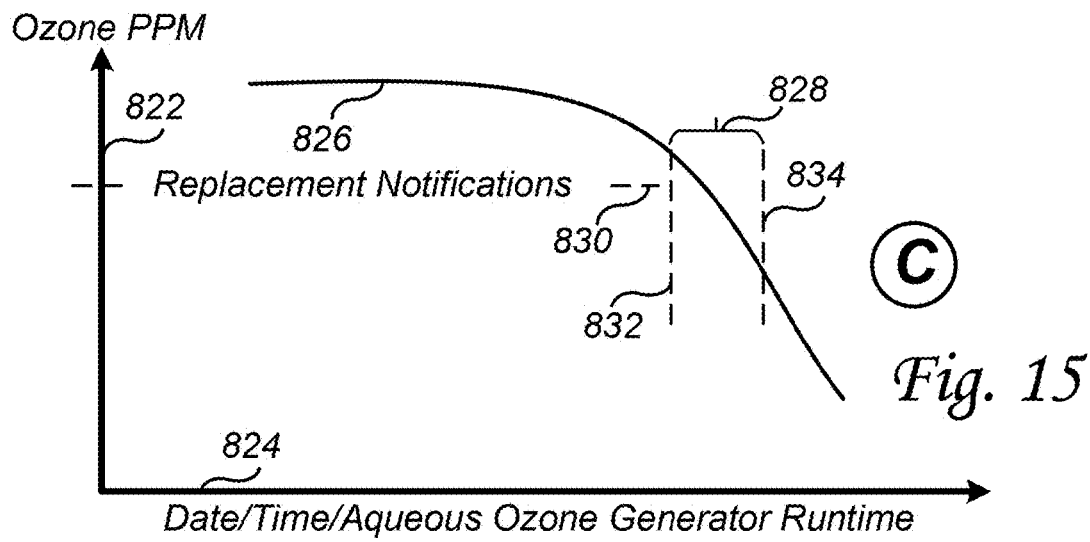
Fig. 15

2102 — Drying The Fruit Or The Vegetable By Air Drying, Salad Spinning, Blotting With Paper Towel Or Clean Kitchen Towel, Commercial Salad Dryers, Or Draining Rack 2104 — Spinning The Fruit Or Vegetable Dry Prior To The Step Of Returning The Fruit Or The Vegetable To The Prepackaged Produce Packaging For Storage 2106 — The Food Item Is A Sandwich, A Salad, A Hamburger, A Pizza, A Taco, Or A Burrito 2108 — Removing Pesticide Residues From The Fruit Or The Vegetable By A Rinse With The Ozonated Concentrate Liquid 2110 — Removing The Fruit Or The Vegetable From A Prepackaged Lettuce Packaging, Prior To The Step Of Removing Pesticide Residues 2112 — Returning The Fruit Or The Vegetable To The Prepackaged Produce Packaging For Storage After The Steps Of Removing, Disinfecting, And Oxygenating 2114 — Oxygenating The Plant Tissue By Removing The Fruit Or The Vegetable From The Immersion And Delaying Frying For An Oxygenation Treatment Time 2116 — Disinfecting A Customer Accessible Countertop Or Table By Misting The Ozonated Concentrate Liquid Onto The Surface Of The Countertop Or The Table And Allowed To Air Dry Absent Agitation Or Removal

*Fig. 28*

POST-HARVEST LETTUCE TREATMENT METHODS

CROSS-REFERENCE TO RELATED APPLICATIONS

This application contains subject matter which is related to the subject matter of the following co-pending applications. The below-listed applications are hereby incorporated herein by reference in its entirety:

This is a U.S. non-provisional application that is a continuation in part of a U.S. non-provisional application Ser. No. 18/428,523, inventor Darren Simmons et al., entitled "AQUEOUS OZONE DISINFECTION SYSTEM", filed Jan. 31, 2024;

this U.S. non-provisional application is a continuation in part of a U.S. non-provisional application Ser. No. 18/528,162, inventor Darren Simmons et al., entitled "AQUEOUS OZONE FLOOR DISINFECTION SYSTEM", filed Dec. 4, 2023; and this U.S. non-provisional application a continuation in part of a U.S. non-provisional application Ser. No. 18/528,194, inventor Darren Simmons et al., entitled "AQUEOUS OZONE FLOOR DISINFECTION SYSTEM", filed Dec. 4, 2023.

TECHNICAL FIELD OF THE INVENTION

This invention relates to post-harvest lettuce treatment methods that use aqueous ozone to disinfect, extend vitality, and reduce the amount of lettuce used in food preparation.

BACKGROUND OF THE INVENTION

Before our invention, food washing, in particular fruits and vegetables in restaurants was largely accomplished by merely rinsing in water. This approach while perhaps removing debris leaves largely untouched bacteria and other pathogens on the surface of the food. As such, contaminated food can easily touch other food preparation surfaces spreading pathogens that are ultimately ingested by consumers of the food.

Another shortcoming is that chemicals used on food preparation surfaces can easily be transferred to the food that is prepared on those surfaces and be ingested by consumers who then consume the food.

Another shortcoming is that many restaurants order large quantities of fruits and vegetables to accommodate food and restaurants supply delivery truck schedules. As such, often fruits and vegetables sit in refrigerators and on shelves for extended periods waiting to be used. During this wait time, bacteria and pathogens on the surface of the fruits and vegetables can accelerate the decay and reduce the freshness levels of the food.

The present invention addresses these and other shortcomings by providing aqueous ozone based disinfection treatment methods and other advantages. For these reasons and shortcomings as well as other reasons and shortcomings there is a long-felt need that gives rise to the present invention.

SUMMARY OF THE INVENTION

The shortcomings of the prior art are overcome and additional advantages are provided through the provision of a post-harvest lettuce treatment method using aqueous ozone to disinfect, extend vitality, and reduce the amount of lettuce needed during the preparation of a food item. The post-harvest lettuce treatment method comprises the steps of creating an ozonated concentrate liquid by way of an aqueous ozone generator. The aqueous ozone generator receives a water source and generates from the water source the ozonated concentrate liquid.

The method continues by removing pesticide residues from one or more lettuce by rinsing with the ozonated concentrate liquid for a pesticide residue removal treatment time. The ozonated concentrate liquid used in the rinse is not reused.

The method continues by disinfecting the lettuce by immersion in the ozonated concentrate liquid for a disinfection treatment time, the lettuce comprises a plant tissue.

The method continues by oxygenating the plant tissue by removing the lettuce from the immersion and delaying drying for an oxygenation treatment time, enhancing metabolic processes of the plant tissue, and increasing the size of the cells of the plant tissue and correspondingly the lettuce which reduces the amount of the lettuce needed in preparation of the food item.

The method continues by neutralizing the odor of the plant tissue by misting the ozonated concentrate liquid onto the plant tissue, at a periodic mist interval and for each of the periodic mist interval, a mist duration treatment time, and returning to the step of neutralizing at the periodic mist interval until the lettuce is utilized in preparation of the food item.

Additional shortcomings of the prior art are overcome and additional advantages are provided through the provision of a post-harvest lettuce treatment method using aqueous ozone to disinfect, extend vitality, and reduce the amount of lettuce needed during the preparation of a food item. The post-harvest lettuce treatment method comprises the steps of creating an ozonated concentrate liquid by way of an aqueous ozone generator. The aqueous ozone generator receives a water source and generates from the water source the ozonated concentrate liquid.

The method continues by removing one or more lettuce from a prepackaged lettuce packaging and removing pesticide residues from the lettuce by rinsing with the ozonated concentrate liquid for a pesticide residue removal treatment time.

The method continues by disinfecting the lettuce by immersion in the ozonated concentrate liquid for a disinfection treatment time. The lettuce comprises a plant tissue.

The method continues by oxygenating the plant tissue by removing the lettuce from the immersion and delaying drying for an oxygenation treatment time, enhancing metabolic processes of the plant tissue and increasing the size of the cells of the plant tissue which reduces the amount of the lettuce needed in preparation of the food item. And, returning the lettuce to the prepackaged lettuce packaging for storage until the lettuce is utilized in the preparation of the food item.

Additional shortcomings of the prior art are overcome and additional advantages are provided through the provision of a post-harvest lettuce treatment method using aqueous ozone to disinfect, extend vitality, and reduce the amount of lettuce needed during the preparation of a food item. The post-harvest lettuce treatment method comprises the steps of creating an ozonated concentrate liquid by way of an aqueous ozone generator. The aqueous ozone generator receives a water source and generates from the water source the ozonated concentrate liquid.

The method continues by removing pesticide residues from one or more lettuce by a rinse with the ozonated concentrate liquid, for a pesticide residue removal treatment time, and disinfecting the lettuce by immersion in the ozonated concentrate liquid for a disinfection treatment time. The lettuce comprises a plant tissue.

The method continues by oxygenating the plant tissue by removing the lettuce from the immersion and delaying drying for an oxygenation treatment time, enhancing metabolic processes of the plant tissue and increasing the size of the cells of the plant tissue which reduces the amount of the lettuce needed in preparation of the food item.

The method continues by neutralizing the odor of the plant tissue by misting the ozonated concentrate liquid onto the food item including the plant tissue prior to serving the food item which comprises the lettuce to a consumer.

Additional shortcomings of the prior art are overcome and additional advantages are provided through the provision of a post-harvest lettuce treatment method using aqueous ozone to disinfect, extend vitality, and reduce the amount of lettuce needed during the preparation of a food item. The post-harvest lettuce treatment method comprises the steps of creating an ozonated concentrate liquid by way of an aqueous ozone generator. The aqueous ozone generator receives a water source and generates from the water source the ozonated concentrate liquid.

The method continues by disinfecting one or more lettuce by filling a prepackaged produce packaging, which comprises the lettuce, with the ozonated concentrate liquid, immersing the lettuce in the ozonated concentrate liquid for a disinfection treatment time. Each of the lettuce comprises a plant tissue.

The method continues by oxygenating the plant tissue by draining the prepackaged produce packaging and delaying before drying the lettuce for an oxygenation treatment time, enhancing the metabolic processes of the plant tissue.

The method continues by neutralizing the odor of the plant tissue by misting the ozonated concentrate liquid onto the plant tissue, at a periodic mist interval and for each of the periodic mist intervals, a mist duration treatment time. And returning to the step of neutralizing at the periodic mist interval until the lettuce is utilized in the preparation of the food item.

System and computer program products corresponding to the above-summarized methods are also described and claimed herein.

Additional features and advantages are realized through the techniques of the present invention. Other embodiments and aspects of the invention are described in detail herein and are considered a part of the claimed invention. For a better understanding of the invention with advantages and features, refer to the description and the drawings.

BRIEF DESCRIPTION OF THE FIGURES

The subject matter which is regarded as the invention is particularly pointed out and distinctly claimed in the claims at the conclusion of the specification. The foregoing and other objects, features, and advantages of the invention are apparent from the following detailed description taken in conjunction with the accompanying drawings in which:

FIG. 1A illustrates one example of a post-harvest produce treatment table and a food preparation disinfection treatment table;

FIG. 1B illustrates one example of a restaurant environment comprising food preparation surfaces;

FIGS. 1C-1E illustrate examples of post-harvest produce which includes lettuce treatment methods;

FIGS. 1G-1H illustrates examples of disinfection by immersion and oxygenation by delayed drying;

FIG. 10 illustrates one example of mixing pulse sequence by way of transitioning between pump/valve activation pulses;

FIG. 15 illustrates one example of monitoring ozone concentration test results;

FIGS. 25-28 illustrate exemplary embodiments that can be interchangeably used with the methods of the present invention.

Figure 1D:
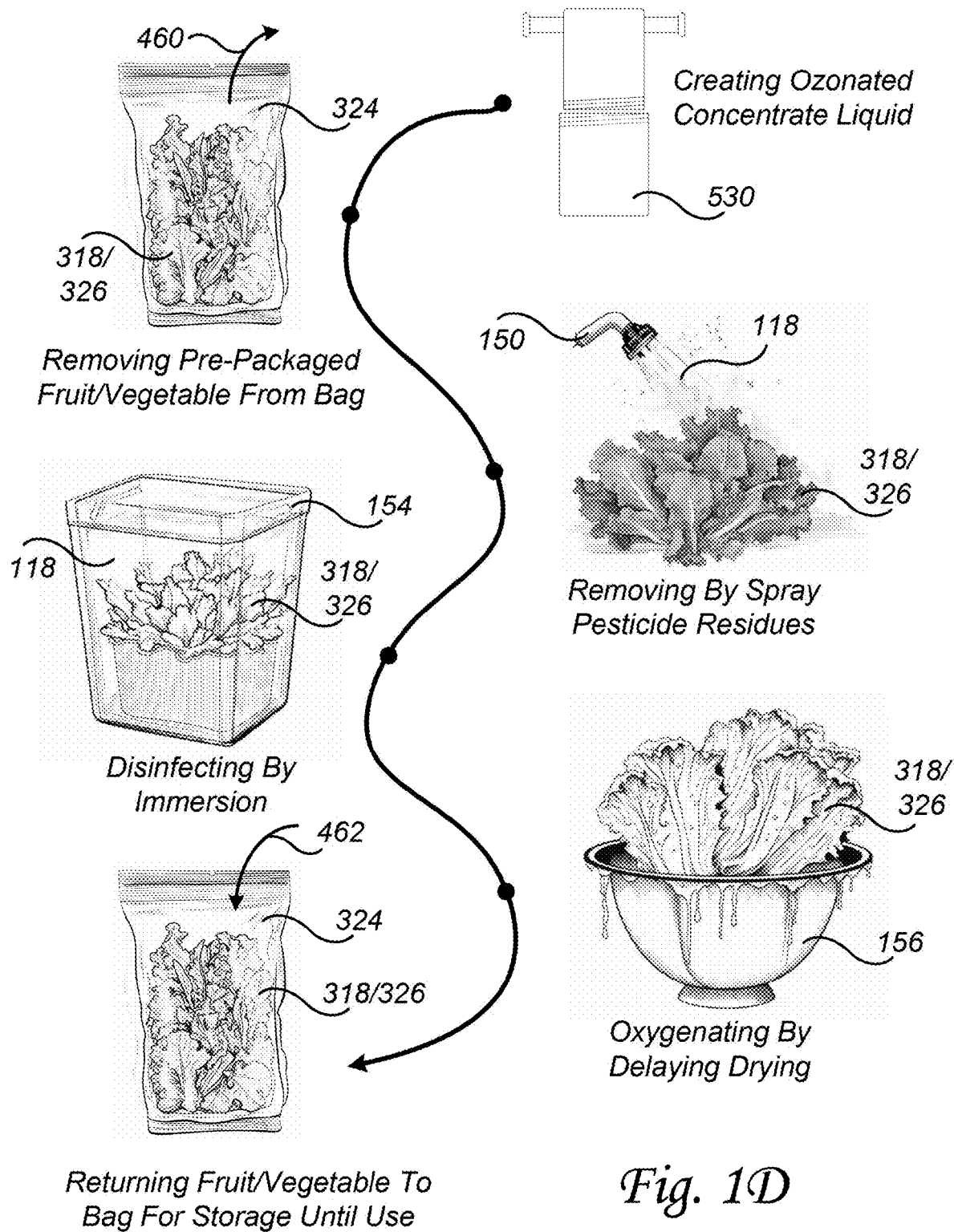

The detailed description explains the preferred embodiments of the invention, together with advantages and features, by way of example with reference to the drawings.

DETAILED DESCRIPTION OF THE INVENTION

Turning now to the drawings in greater detail, it will be seen that in FIG. 1A, there is illustrated one example of a post-harvest produce treatment table 450 and a food preparation disinfection treatment table 454.

In an exemplary embodiment and with reference to the post-harvest produce treatment table 450, reference 'A', fruits and vegetables 318 including lettuce can generally be referred to as produce 318 and can be treated with several different steps that use aqueous ozone to disinfect and extend the vitality of the produce 318. For disclosure purposes, the term "produce" or "produce 318" can generally be items found or grown on a farm which includes fruits and vegetables including lettuce and some animal products.

An advantage, in the present invention, is that with respect to lettuce, as one example, such post-harvest produce treatment 450 can increase the volume of lettuce primarily in the step of oxygenation thus requiring less lettuce in the food product 318. This can lower the daily need amount as well as reduce the cost of producing food item 328 for restaurant 312. Customer 310 also benefits as the right-sized amount of lettuce makes the final food product 318 appear and taste better versus overfilling with limp worn-out lettuce.

In an exemplary embodiment, in operation, in a series of post-harvest produce treatment steps 452, the produce is first sprayed with the ozonated concentrate liquid 118 to remove pesticide residues from the surface of the produce 318. The aqueous ozonated liquid 118 generated from the aqueous ozone generator 520 is particularly well suited to break down the pesticide compounds removing the residues as well as other contaminates from the surface of the produce 318. Such ozonated concentrate liquid 118 spray can be administered by way of a spray nozzle 150 and such a pesticide residue removal treatment time 468 can be preferable in the range of several seconds, or other suitable time range, with the runoff of the ozonated concentrate liquid 118 preferably being allowed to drain away from the produce 318 without reuse.

In a second step, the produce 318 can be disinfected by being immersed in ozonated concentrate liquid 118. In this regard, the produce 318 can be placed in an immersion container 154, and the immersion container 154 filled with the ozonated concentrate liquid 118 or by other methods. At least FIG. 1G better illustrates one example of an immersion tank 154. Such immersion better ensures that the disinfection occurs on all parts of the produce 318. In operation, the produce 318 can be immersed in the ozonated concentrate liquid 118 for a disinfection treatment time 470 in the range of less than one minute, or for other suitable duration.

In a third step, the produce 318 can be oxygenated allowing the additional oxygen molecules in the aqueous ozone ($O_3$) to permeate the produce 318 plant tissue 326 revitalizing the cellular structure of the plant tissue 326 for an oxygenation treatment time 472 before drying the produce 318. In this regard, aqueous ozone is a rich source of oxygen. In operation, when ozonated water is applied to produce 318 including lettuce, the mechanism of action of the aqueous ozone introduces additional oxygen into the plant tissues 326. This can enhance the metabolic processes within the produce cells, revitalizing the leaves and promoting overall freshness. To accomplish this, the ozonated concentrate liquid 118 can be drained away from the produce 318, and drying of the produce 318 delayed for oxygenation treatment time 472, allowing the ozonated concentrate liquid 118 to remain on the produce oxygenating the plant tissue 326 for greater than one minute, or other suitable time.

In an exemplary embodiment, such drying of the lettuce can be by blotting with a towel 320, forced air flow 322, air-drying, spinning the produce 318 in a device to use centripetal force to remove excess water, or by other suitable methods as may be required and or desired in a particular embodiment.

In a fourth step, plant tissue 326 odor from decay and other sources can be neutralized by misting the ozonated concentrate liquid onto the plant tissue onto the produce 318 at a periodic mist interval 474 in the range of hourly to daily, or other suitable time, and at each interval for a mist duration treatment time to better ensure produce 318 complete coverage and seeping of the ozonated concentrate liquid into produce 318 crevasses. The mist duration treatment time can be in the range of seconds to less than one minute or other suitable time. The neutralization step is typically repeated at the periodic mist interval 474 until the produce is used in the preparation of a food item 328.

In an exemplary embodiment, a spray bottle 152, or other suitable misting device can be used to mist ozonated concentrate liquid 118 as required and/or desired in a particular embodiment.

In a plurality of exemplary embodiment, the post-harvest produce treatment can be used steps 452 can be organized and the treatment durations adjusted based, in part, on the types and kind of produce 318, how long produce is left in trays 158, the setup of the restaurant food preparation area and processes, the types of food items 328 being prepared, and other considerations.

In an exemplary embodiment and with reference to the food preparation disinfection treatment table 454, FIG. 1A reference 'B', fruits and vegetables 318 including lettuce generally referred to as produce 318 can be treated with several different steps that use aqueous ozone to disinfect and extend the vitality of the produce 318. Additionally, steps can be taken to disinfect restaurant 312, food preparation surfaces 314 so that contamination and pathogens aren't transferred from food preparation surface 214 to food item 328 and by way of the food preparation surfaces 314 from one food item 328 to another food item 328 prepared on the same food preparation surface 314.

In an exemplary embodiment, in operation, in a series of food preparation disinfection treatment steps 456, the initial step can be to disinfect the produce 318 by immersion in ozonated concentrate liquid 118. In this regard, the produce 318 can be placed in an immersion container 154, and the immersion container 154 filled with the ozonated concentrate liquid 118 or by other methods. At least FIG. 1G better illustrates one example of an immersion tank 154. Such immersion better ensures that the disinfection occurs on all parts of the produce 318. In operation, the produce 318 can be immersed in the ozonated concentrate liquid 118 for a disinfection treatment time 470 in the range of less than one minute, or for other suitable duration.

In the second step, the food preparation surfaces 314 in restaurant 312 can be disinfected by misting the ozonated concentrate liquid onto the plant tissue on the surfaces 314. In operation, preferably the misted food preparation surfaces 314 are left for surface a disinfection treatment time to air dry for a disinfection treatment time allowing maximum time for the aqueous ozone to disinfect and inactivate pathogens. If wiping of the food preparation surface is required or desired doing so after the food preparation surface is misted and waiting a disinfection treatment time of greater than 30 seconds is preferred. In other embodiments, other suitable surface disinfection treatment times can be implemented as may be required and/or desired.

In an exemplary embodiment, a spray bottle 152, or other suitable misting device can be used to mist ozonated concentrate liquid 118 as required and/or desired in a particular embodiment.

In a third step, plant tissue 326 odor from decay and other sources can be neutralized by misting the ozonated concentrate liquid onto the plant tissue onto the produce 318 at a periodic mist interval 474 in the range of hourly to daily, or other suitable time, and at each interval for a mist duration treatment time to better ensure produce 318 complete coverage and seeping of the ozonated concentrate liquid into produce 318 crevasses. The mist duration treatment time can be in the range of seconds or other suitable time. The neutralization step is typically repeated at the periodic mist interval until the produce is used in the preparation of a food item 328.

Additionally, can be oxygenated allowing the additional oxygen molecules in the aqueous ozone to permeate the produce 318 plant tissue 326 revitalizing the cellular structure of the plant tissue 326. In this regard, aqueous ozone is a rich source of oxygen. In operation, when ozonated water is applied to produce 318 including lettuce, the mechanism of action of the aqueous ozone introduces additional oxygen into the plant tissues 326. This can enhance the metabolic processes within the produce cells, revitalizing the leaves and promoting overall freshness. To accomplish this, the ozonated concentrate liquid 118 from the neutralizing odor mist can be left on the surface of the produce 318, oxygenating the plant tissue 326 while the produce air dries.

In the fourth step, a food item 328 can be prepared on the food surface 314 that comprises the produce 318.

In a plurality of exemplary embodiments, the food preparation disinfection treatment steps 456 can be organized and the treatment durations of each step adjusted based, in part, on the types and kind of produce 318, how long produce is left in trays 158, the setup of the restaurant food preparation area and processes, the types and/or kinds of food preparation surface 314, the types of food items 328 being prepared, and other considerations.

For disclosure purposes, food preparation surfaces 314 can include tables, countertops, cooking equipment, food slicers, toasters, and other types or kinds of surfaces and equipment, as may be required and/or desired in a particular embodiment.

Referring to FIG. 1B, there is illustrated one example of a restaurant 312 environment comprising a plurality of food preparation surfaces 314. In an exemplary embodiment, customers 310 can be seated at tabled or countertops 316. For disclosure purposes tables or countertops can also be referred to as food preparation surfaces as customers 310 routines eat their food items 328 aided to hold, sort, or organize their food in other ways by on the tables or countertops 316. Additionally, spray bottle 152, or other suitable misting devices can be used to mist ozonated concentrate liquid 118 on the food preparation surfaces 314 including the countertops or tables 316 as required and/or desired in a particular embodiment.

Figure 17:
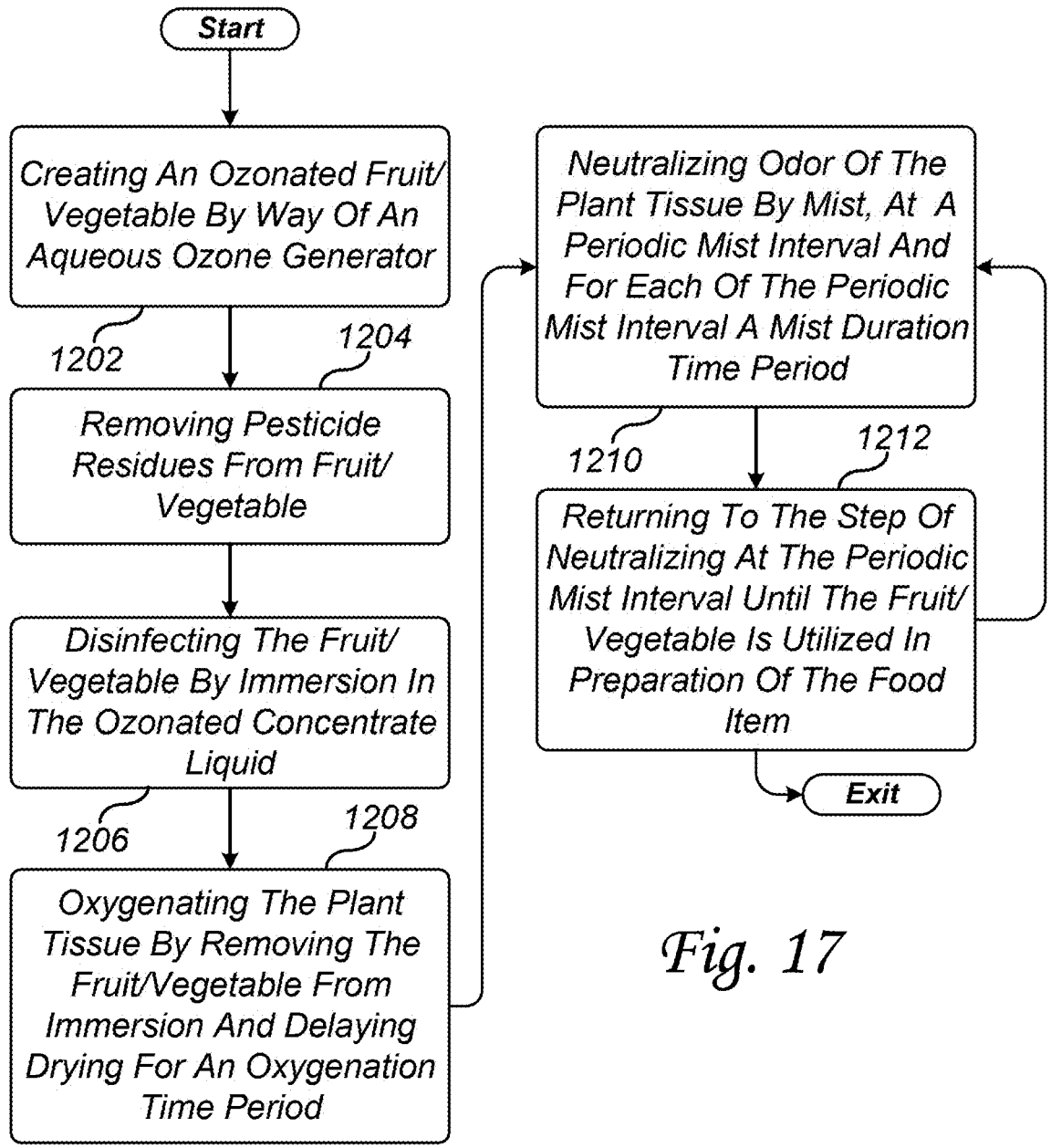
FIGS. 17-20 illustrate examples of a post-harvest lettuce treatment method.

Referring to FIGS. 1C and 17, there is illustrated one example of a post-harvest produce 318 which includes the lettuce treatment method. In an exemplary embodiment, a post-harvest produce 318 which includes the lettuce treatment method utilizes aqueous ozone to disinfect, extend vitality, and reduce the amount of produce 318 needed including lettuce during the preparation of a food item 328. The post-harvest lettuce treatment method begins in step 1202 by creating an ozonated concentrate liquid 118 by way of an aqueous ozone generator 530. The aqueous ozone generator 530 receives a water source 102 and generates from the water source 102 the ozonated concentrate liquid 118. The method then moves to step 1204.

The method continues in step 1204 by removing pesticide residues from one or more produce 318 which includes lettuce by a rinse with the ozonated concentrate liquid 118 for a pesticide residue removal treatment time 468, the ozonated concentrate liquid 118 used in the rinse can be discarded or otherwise not reused in the treatment process. The method then moves to step 1206.

The method continues in step 1206 by disinfecting produce 318 which includes lettuce by immersion in the ozonated concentrate liquid 118 for a disinfection treatment time 470. The produce 318 including the lettuce comprises a plant tissue 326. The method then moves to step 1208.

The method in step 1208 continues by oxygenating the plant tissue 326 by removing the produce 318 which includes lettuce from the immersion and delaying drying for an oxygenation treatment time 472, enhancing metabolic processes of the plant tissue 326, and increasing the size of the cells of the plant tissue 326 and correspondingly the lettuce which reduces the amount of the lettuce needed in preparation of the food item 328.

An advantage, in the present invention, is how the step of oxygenating the produce 318 which includes the lettuce revitalizes the plant tissue 326 including increasing the size of the cells of the plant tissue 326 thus requiring less lettuce (because the lettuce leaves are bigger) in the prepared food item which comprises the lettuce 318. In this regard, the lettuce 318 plant tissue 326 cell size increase when wetted with aqueous ozone and delayed drying can be attributed to several factors including:

- Cell turgor pressure: When plant cells absorb water, they become turgid due to the increased pressure within the cell known as turgor pressure. This pressure helps maintain the structural integrity of the cell and contributes to cell enlargement;
- Cell wall expansion: Aqueous ozone breaks down certain compounds in the cell wall, such as lignin and hemicellulose. This breakdown can make the cell wall more flexible, allowing it to expand more easily when water is taken up by the cell;
- Increased water uptake: Ozone enhances water uptake by plant cells. As water is absorbed, the cells expand in size. The presence of ozone facilitates the movement of water into the cells through various mechanisms, such as modifying cell membrane permeability;
- Stimulation of metabolic processes: Aqueous ozone also stimulates various metabolic processes within the plant cells. This leads to increased cellular activity, including the uptake of water and nutrients, contributing to cell enlargement;
- Cell elongation and growth: Water uptake is crucial for cell elongation, which is a key process in plant growth. The elongation of cells contributes to the overall growth of plant tissues, and the presence of ozone influences the factors that regulate cell elongation; and
- Other beneficial factors and specific effects of aqueous ozone on plant cells can vary depending on concentration, exposure time, and other environmental factors. The method then moves to step 1210.

The method continues in step 1210 by neutralizing the odor of the plant tissue 326 by misting the ozonated concentrate liquid onto the plant tissue, at a periodic mist interval 474, and for each of the periodic mist intervals 474, a mist duration treatment time. The method then moves to step 1212.

The method continues in step 1212 by returning 458 to step 1210 of neutralizing at the periodic mist interval 474 until the produce 318 which includes lettuce is utilized in the preparation of the food item 328.

Figure 18:
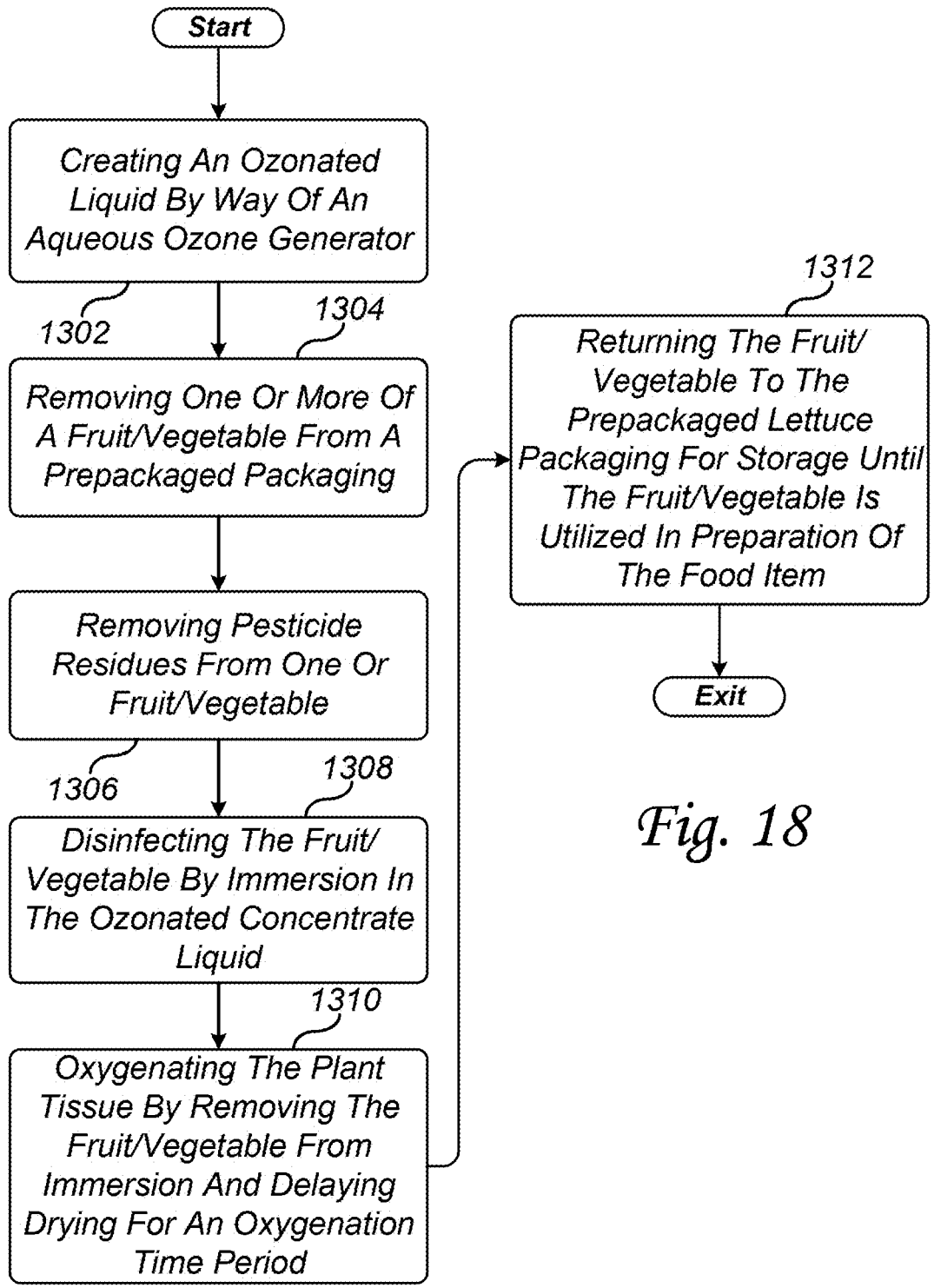

Referring to FIGS. 1D and 18, there is illustrated one example of a post-harvest produce 318 which includes the lettuce treatment method. In an exemplary embodiment, a post-harvest lettuce 318 treatment method uses aqueous ozone to disinfect, extend vitality, and reduce the amount of lettuce 318 needed during the preparation of a food item 326. The post-harvest lettuce treatment method begins in step 1302 by creating an ozonated concentrate liquid 118 by way of an aqueous ozone generator 530. The aqueous ozone generator 530 receives a water source 102 and generates from the water source 102 the ozonated concentrate liquid 118. The method then moves to step 1304.

The method continues in step 1304 by removing 460 one or more lettuce 318 from a prepackaged lettuce packaging 324. The method then moves to step 1306.

The method continues in step 1306 by removing pesticide residues from the lettuce 318 by a rinse with the ozonated concentrate liquid 118 for a pesticide residue removal treatment time 468. The method then moves to step 1308.

The method continues in step 1308 by disinfecting the lettuce 318 by immersion in the ozonated concentrate liquid 118 for a disinfection treatment time 470. The lettuce comprises a plant tissue 326. The method then moves to step 1310.

The method continues in step 1310 by oxygenating the plant tissue 326 by removing the lettuce 318 from the immersion and delaying drying for an oxygenation treatment time 472, enhancing the metabolic processes of the plant tissue and increasing the size of the cells of the plant tissue 326 which reduces the amount of the lettuce needed in the preparation of the food item 328. The method then moves to step 1312.

The method continues in step 1312 by returning 462 the lettuce 318 to the prepackaged lettuce packaging 324 for storage until the lettuce 318 is utilized in the preparation of food item 328. The method is then exited.

Figure 1E:
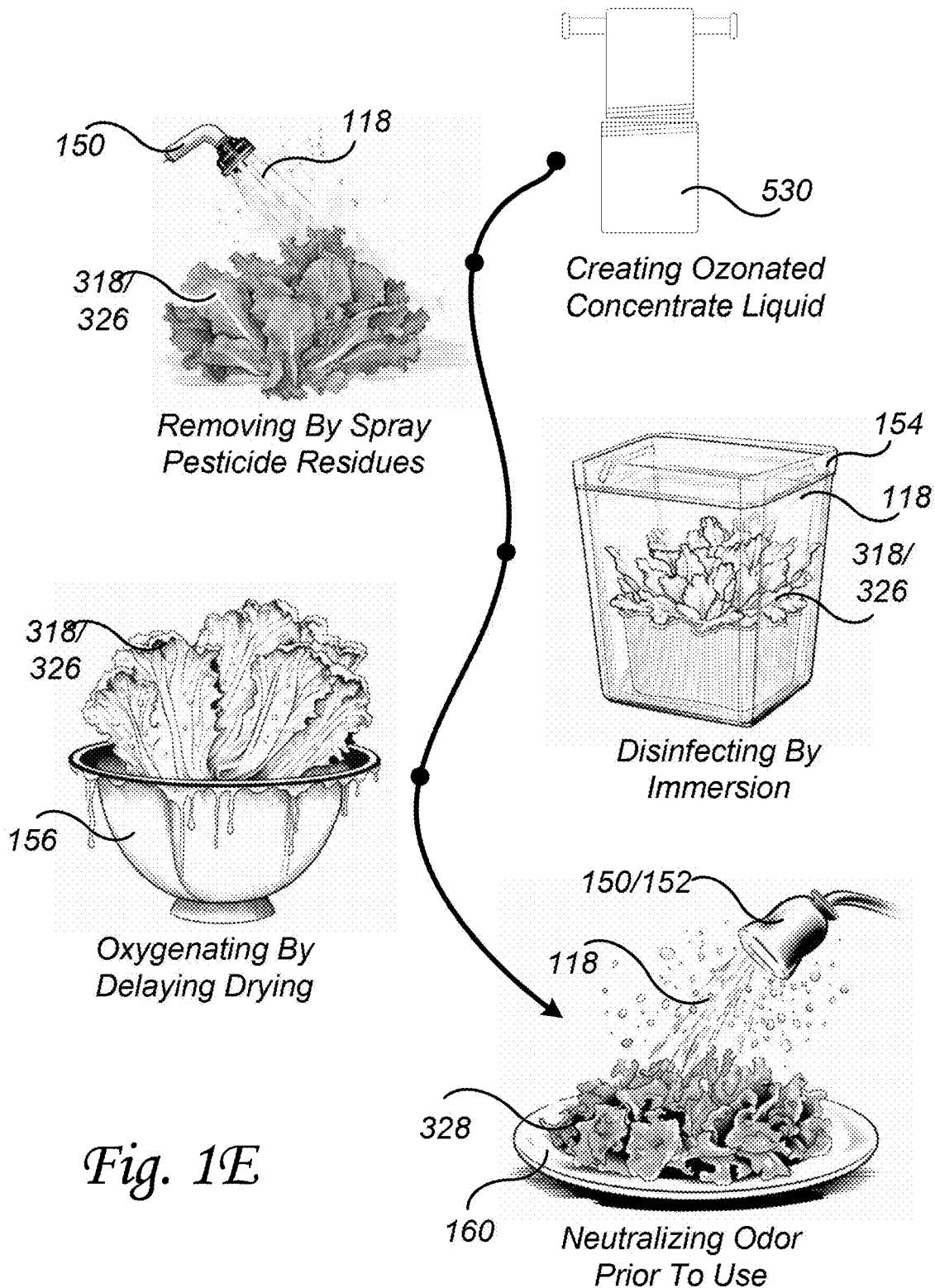
Figure 19:
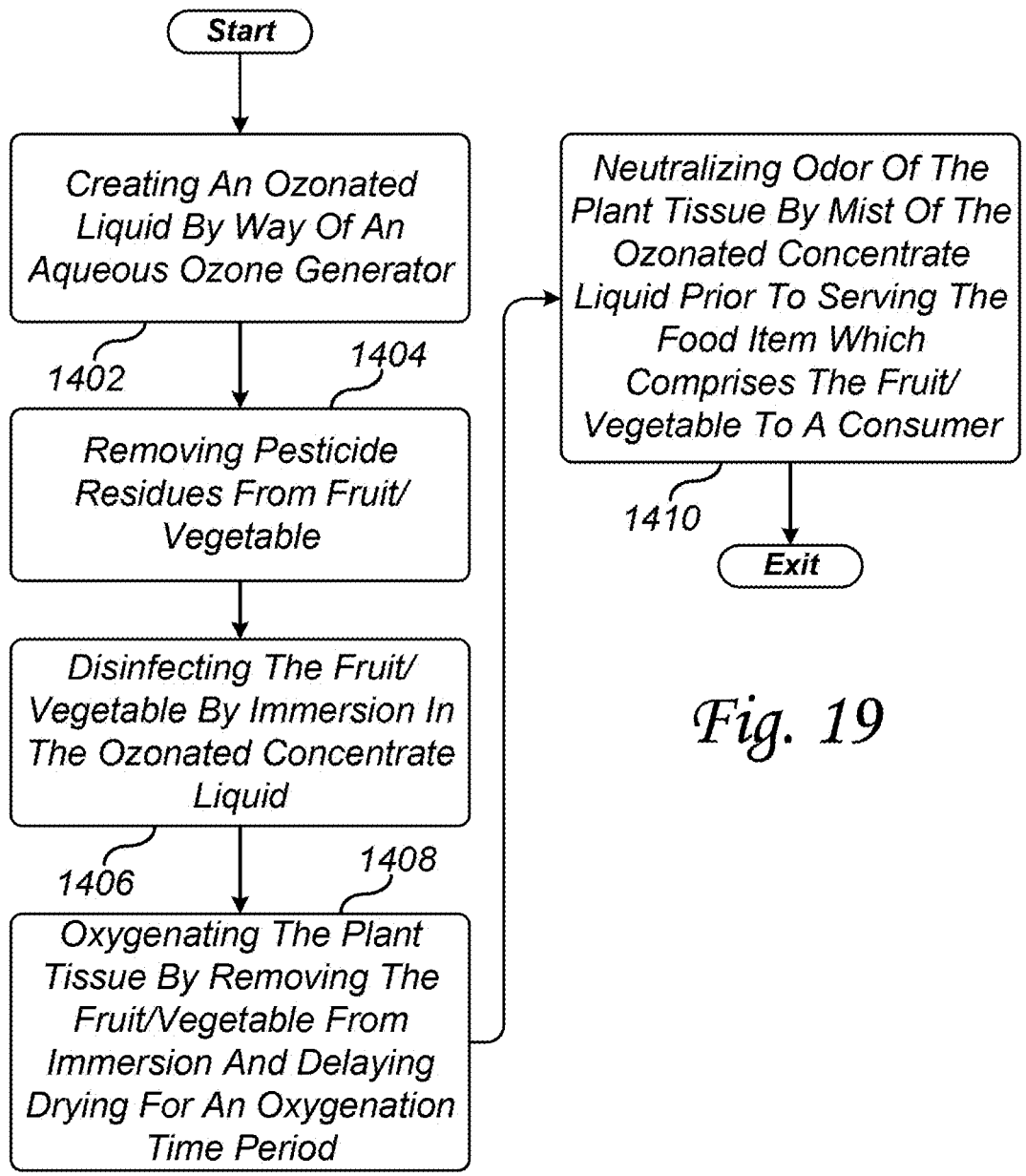

Referring to FIGS. 1E and 19, there is illustrated one example of a post-harvest produce 318 which includes the lettuce treatment method. In an exemplary embodiment, a post-harvest lettuce 318 treatment method uses aqueous ozone to disinfect, extend vitality, and reduce the amount of lettuce 318 needed during the preparation of a food item 326. The post-harvest lettuce treatment method begins in step 1402 by creating an ozonated concentrate liquid 118 by way of an aqueous ozone generator 530. The aqueous ozone generator 530 receives a water source 102 and generates from the water source 102 the ozonated concentrate liquid 118. The method then moves to step 1404.

The method continues in step 1404 by removing pesticide residues from one or more lettuce 318 by a rinse with the ozonated concentrate liquid 118, for a pesticide residue removal treatment time 468. The method then moves to step 1406.

The method continues in step 1406 by disinfecting the lettuce 318 by immersion in the ozonated concentrate liquid 118 for a disinfection treatment time 470. The lettuce 318 comprises a plant tissue 326. The method then moves to step 1408.

The method continues in step 1408 by oxygenating the plant tissue 326 by removing the lettuce 318 from the immersion and delaying drying for an oxygenation treatment time 472, enhancing metabolic processes of the plant tissue 326 and increasing the size of the cells of the plant tissue 326 which reduces the amount of the lettuce 318 needed in the preparation of the food item 328. The method then moves to step 1410.

The method continues in step 1410 by neutralizing the odor of the plant tissue 326 by misting the ozonated concentrate liquid onto the plant tissue prior to serving the food item 328 which comprises the lettuce 318 to a consumer 310.

Figure 1F:
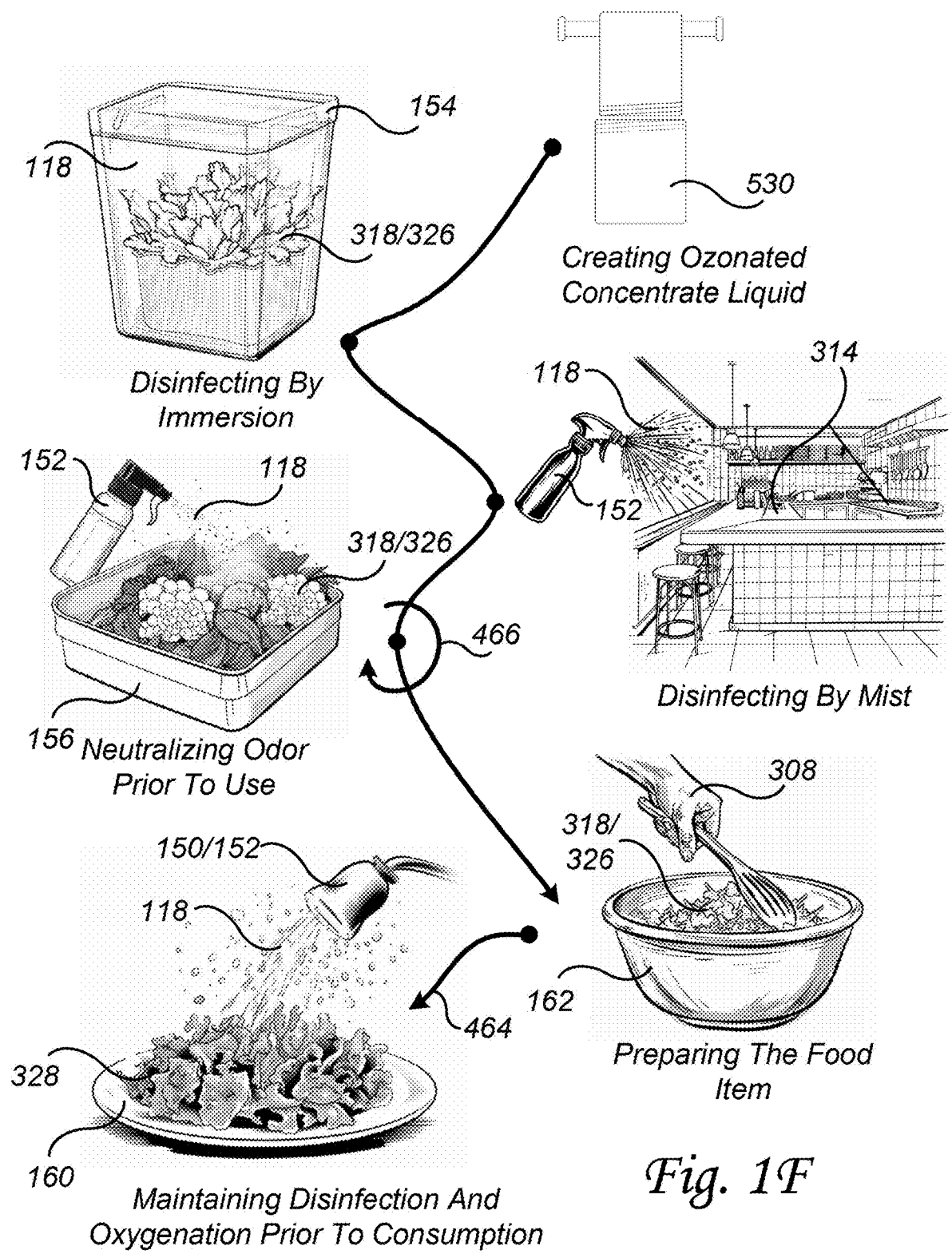
FIG. 1F illustrates one example of a food preparation disinfection treatment method.
Figure 1H:
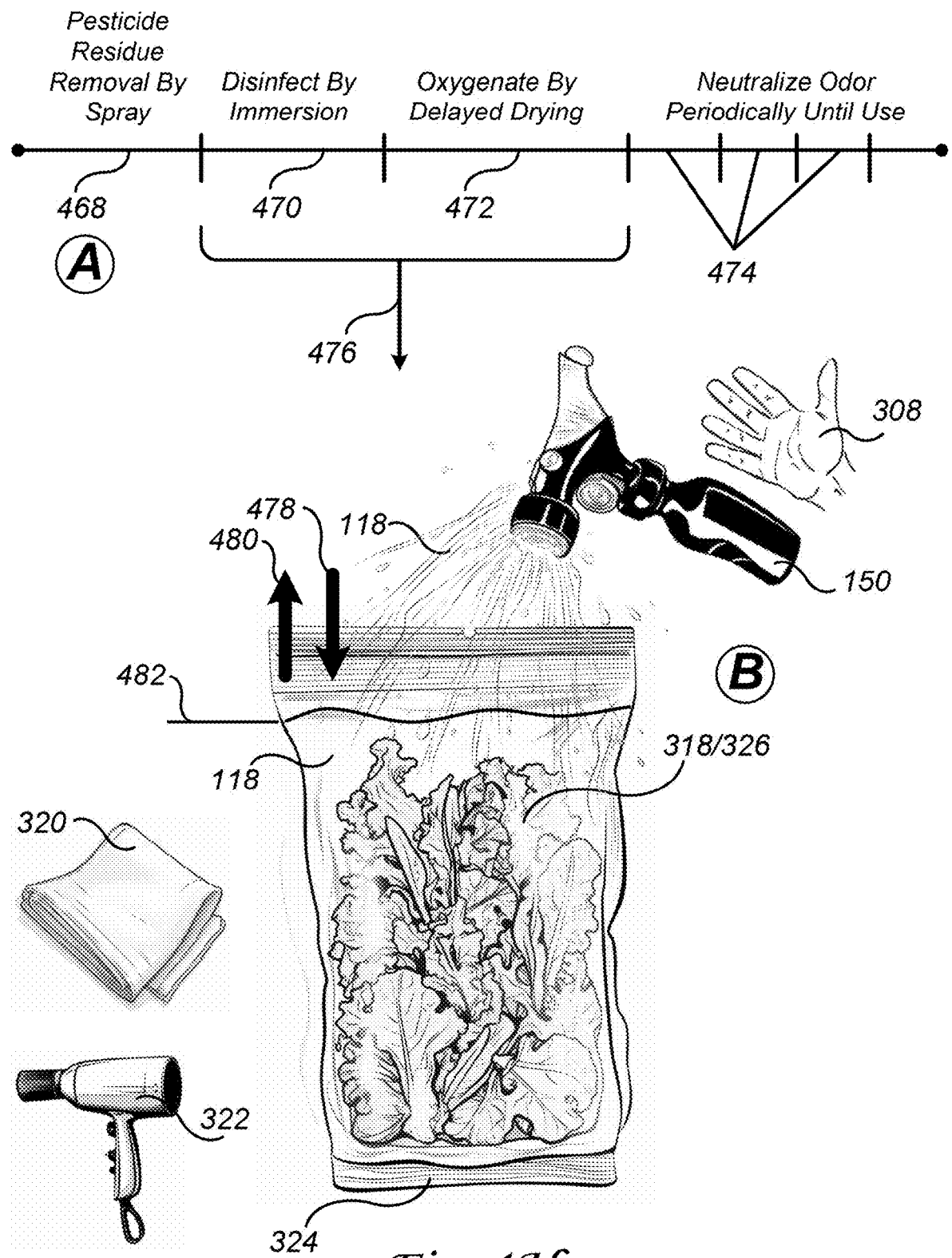
Figure 20:
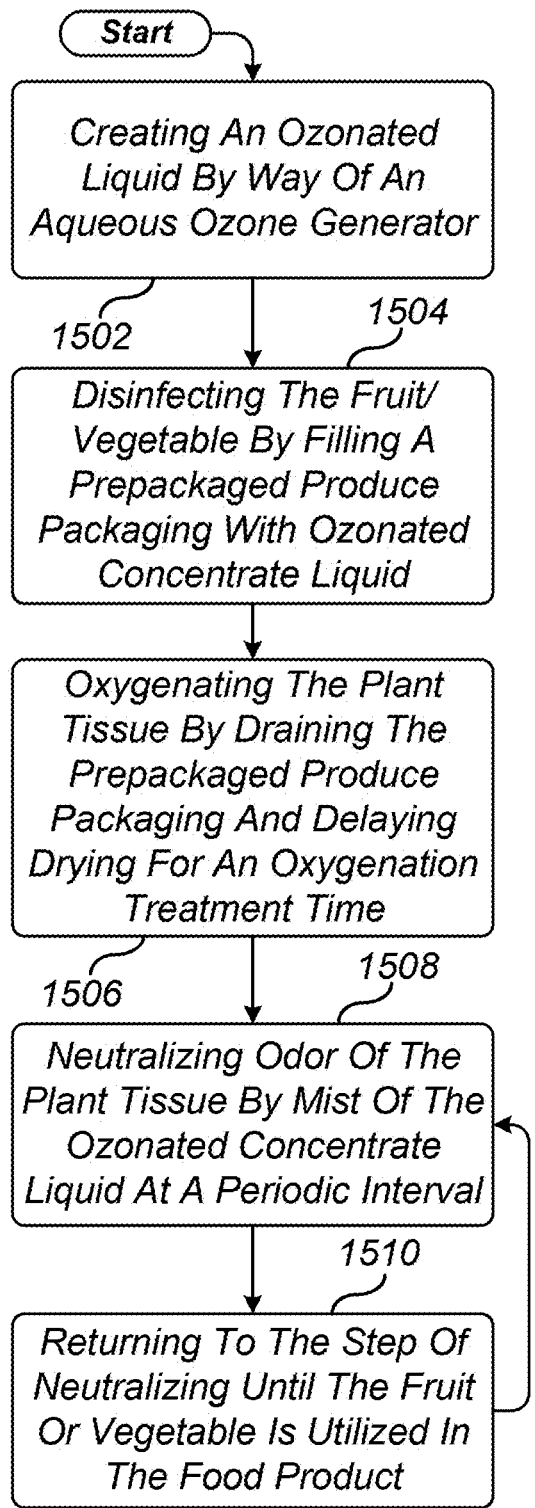

Referring to FIGS. 1H, and 20, there is illustrated one example of a post-harvest produce 318 which includes the lettuce treatment method. In an exemplary embodiment, a post-harvest lettuce 318 treatment method uses aqueous ozone to disinfect, extend vitality, and reduce the amount of lettuce 318 needed during the preparation of a food item 326. The post-harvest lettuce treatment method begins in step 1502 by creating an ozonated concentrate liquid 118 by way of an aqueous ozone generator 530. The aqueous ozone generator 530 receives a water source 102 and generates from the water source 102 the ozonated concentrate liquid 118. The method then moves to step 1504.

The method continues in step 1504 by disinfecting one or more lettuce 318 by filling 478 a prepackaged produce packaging 324, which comprises the lettuce, with the ozonated concentrate liquid 118, immersing (to fill line 482) the lettuce 318 in the ozonated concentrate liquid 118 for a disinfection treatment time 470. Each of the lettuce 318 comprises a plant tissue 326. The method then moves to step 1506.

The method continues in step 1506 by oxygenating the plant tissue 326 by draining 480 the prepackaged produce packaging and delaying before drying the lettuce 318 for an oxygenation treatment time 472, enhancing the metabolic processes of the plant tissue 326.

In an exemplary embodiment, such drying of the lettuce can be by blotting with a towel 320, forced air flow 322, air-drying, spinning the produce 318 in a device to use centripetal force to remove excess water, or by other suitable methods as may be required and or desired in a particular embodiment. The method then moves to step 1508.

The method continues in step 1508 by neutralizing the odor of the plant tissue 326 by misting the ozonated concentrate liquid 118 onto the plant tissue 326, at periodic mist intervals 474 and for each of the periodic mist intervals 472, a mist duration treatment time. The method then moves to step 1510.

The method continues in step 1510 by returning to step 1508 of neutralizing at the periodic mist interval 474 until lettuce 318 is utilized in the preparation of food item 328. The method is the exited.

Figure 21:
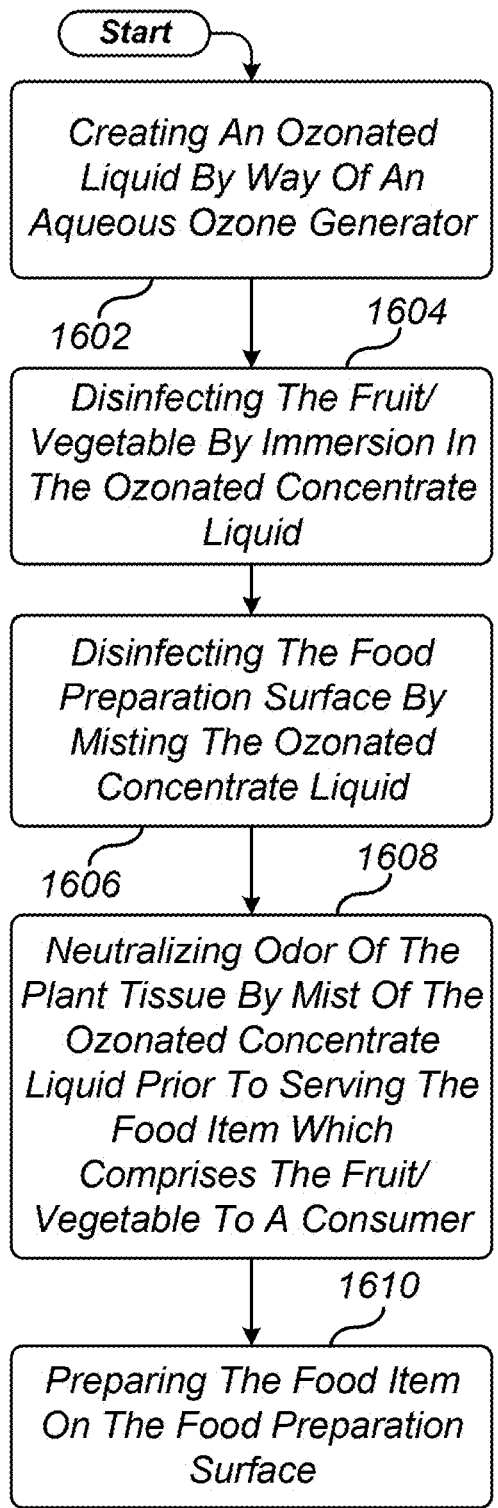
FIGS. 21-24 illustrate examples of a food preparation disinfection treatment method.

Referring to FIGS. 1F and 21, there is illustrated one example of a food preparation disinfection treatment method. In an exemplary embodiment, a food preparation disinfection treatment method disinfects fruits or vegetables 318, and food preparation surfaces 314 during the preparation of food item 328 in a restaurant 312 environment. In an exemplary embodiment, the method begins in step 1602 by creating an ozonated concentrate liquid 118 by way of an aqueous ozone generator 530. The aqueous ozone generator 530 receives a water source 102 and generates from the water source 102 the ozonated concentrate liquid 118. The method then moves to step 1604.

The method continues in step 1604 by disinfecting one or more fruits 318 or one or more vegetables 318 by immersion in the ozonated concentrate liquid 118 for a disinfection treatment time 470. Each of the fruit and the vegetable 318 comprises a plant tissue 326. The method then moves to step 1606.

The method continues in step 1606 by disinfecting one or more food preparation surface 314 by misting the ozonated concentrate liquid 118 onto the food preparation surface 314 and waiting a surface disinfection treatment time, better illustrated in at least FIG. 1A reference 'B', before using the food preparation surface 314. The method then moves to step 1608.

The method continues in step 1608 by neutralizing the odor of the plant tissue 326 by misting the ozonated concentrate liquid 118 onto the plant tissue 326, at a periodic mist interval 474 and for each of the periodic mist interval 474, a mist duration treatment time. Repeating 466, the step until the fruit or vegetable 318 is used in a food item 328. The method then moves to step 1610.

The method continues in step 1610 by preparing the food item 328 on the food preparation surface 314. Food item 328 comprises the fruit or the vegetable 318. The method is then exited.

Figure 22:
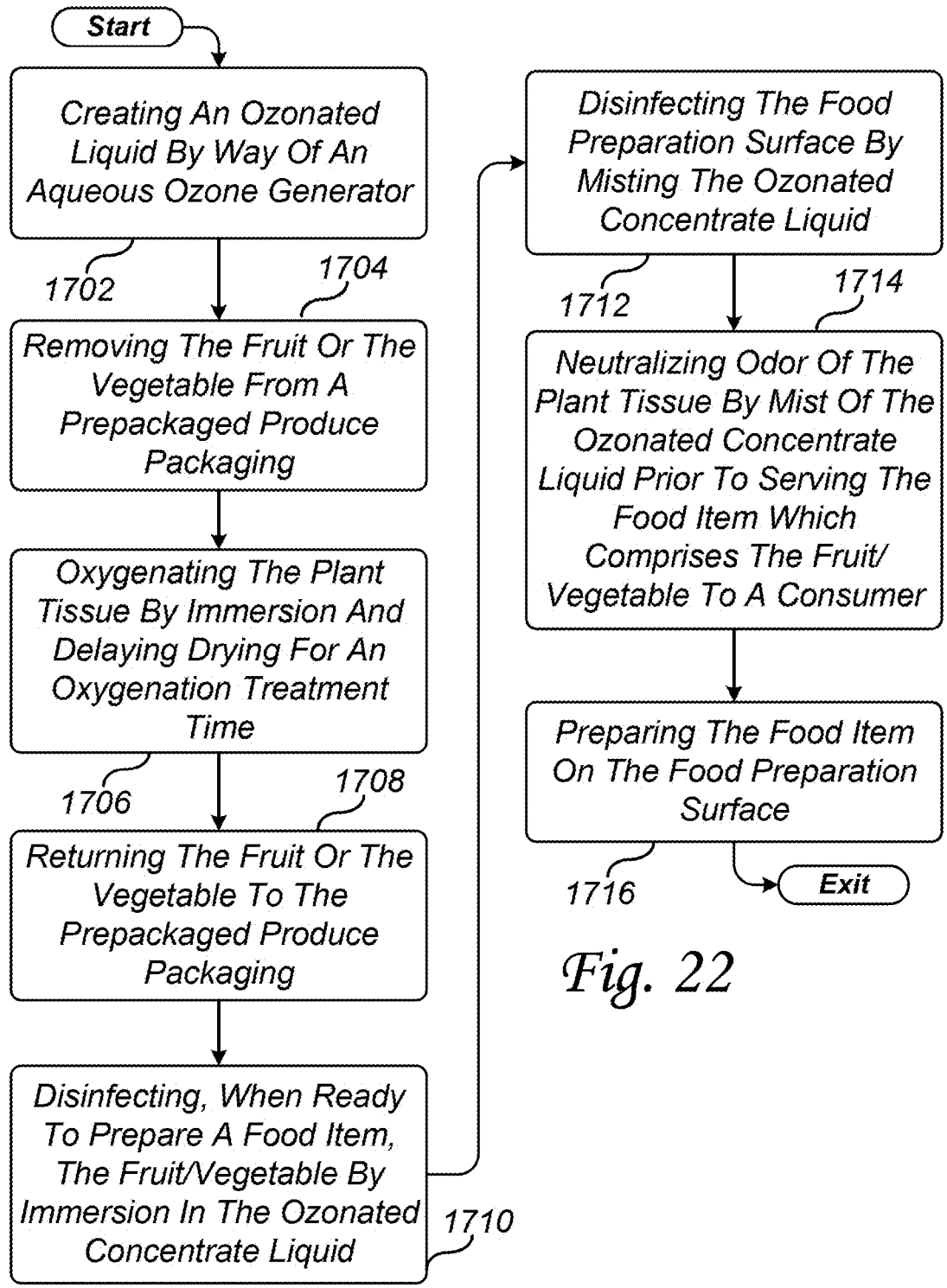

Referring to FIGS. 1F and 22, there is illustrated one example of a food preparation disinfection treatment method. In an exemplary embodiment, a food preparation disinfection treatment method disinfects fruits or vegetables 318, and food preparation surfaces 314 during the preparation of food item 328 in a restaurant 312 environment. In an exemplary embodiment, the method begins in step 1702 by creating an ozonated concentrate liquid 118 by way of an aqueous ozone generator 530. The aqueous ozone generator 530 receives a water source 102 and generates from the water source 102 the ozonated concentrate liquid 118. The method then moves to step 1704.

The method continues in step 1704 by removing one or more fruits 318 or one or more vegetables 318 from a prepackaged produce packaging 324. Each of the fruit and the vegetable 318 comprises a plant tissue 326. The method then moves to step 1706.

The method continues in step 1706 by oxygenating the plant tissue 326 by immersion and delaying drying for an oxygenation treatment time 472, enhancing the metabolic processes of the plant tissue 326. The method then moves to step 1708.

The method continues in step 1708 by returning the fruit 318 or the vegetable 318 to the prepackaged produce packaging 324 for storage until needed for preparing the food item 328. The method then moves to step 1710.

The method continues in step 1710 by disinfecting, when ready to prepare the food item 328, the fruit 318, or the vegetable 318 by immersion in the ozonated concentrate liquid 118 for a disinfection treatment time 470. The method then moves to step 1712.

The method continues in step 1712 by disinfecting one or more food preparation surface 314 by misting the ozonated concentrate liquid 118 onto the food preparation surface 314 and waiting a surface disinfection treatment time, better illustrated in at least FIG. 1A reference 'B', before using the food preparation surface 314. The method then moves to step 1714.

The method continues in step 1714 by neutralizing the odor of the plant tissue 326 by misting the ozonated concentrate liquid 118 onto the plant tissue 326, at a periodic mist interval 474 and for each of the periodic mist interval 474, a mist duration treatment time. Repeating 466, the step until the fruit or vegetable 318 is used in a food item 328. The method then moves to step 1716.

The method continues in step 1716 by preparing the food item 328 on the food preparation surface 314. The food item 328 comprises the fruit 318 or the vegetable 318. The method is the exited.

Figure 23:
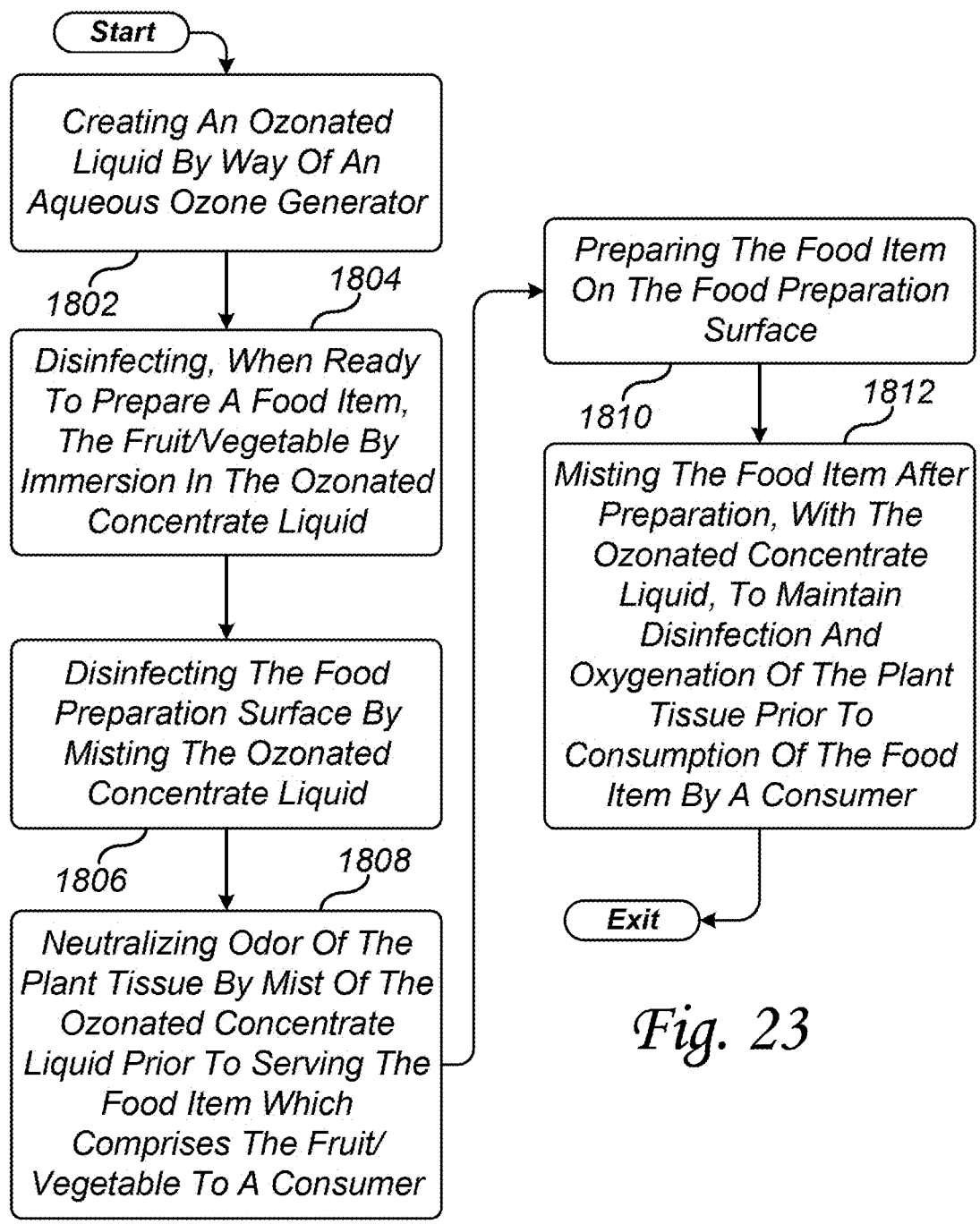

Referring to FIGS. 1F and 23, there are illustrated examples of a food preparation disinfection treatment method. In an exemplary embodiment, a food preparation disinfection treatment method disinfects fruits or vegetables 318, and food preparation surfaces 314 during the preparation of food item 328 in a restaurant 312 environment. In an exemplary embodiment, the method begins in step 1802 by creating an ozonated concentrate liquid 118 by way of an aqueous ozone generator 530. The aqueous ozone generator 530 receives a water source 102 and generates from the water source 102 the ozonated concentrate liquid 118. The method then moves to step 1804.

The method continues in step 1804 by disinfecting one or more fruits 318 or one or more vegetables 318 by immersion in the ozonated concentrate liquid 118 for a disinfection treatment time 470. Each of the fruit 318 and the vegetable 318 comprises a plant tissue 326. The method then moves to step 1806.

The method continues in step 1806 by disinfecting one or more food preparation surface 314 by misting the ozonated concentrate liquid 118 onto the food preparation surface 314 and waiting a surface disinfection treatment time, better illustrated in at least FIG. 1A reference 'B', before using the food preparation surface 314. The method then moves to step 1808.

The method continues in step 1808 by neutralizing the odor of the plant tissue 326 by misting the ozonated concentrate liquid 118 onto the plant tissue 326, at a periodic mist interval 474 and for each of the periodic mist interval 474, a mist duration treatment time. The method then moves to step 1810.

The method continues in step 1810 by preparing the food item 328 on the food preparation surface 314. The food item 328 comprises the fruit 318 or the vegetable 318. The method then moves 464 to step 1812.

The method continues in step 1812 by maintaining disinfection and oxygenation of the plant tissue 326 by misting the food item 328, with the ozonated concentrate liquid 118, after preparation and prior to consumption of the food item 328 by a consumer 310. The method is the exited.

Figure 24:
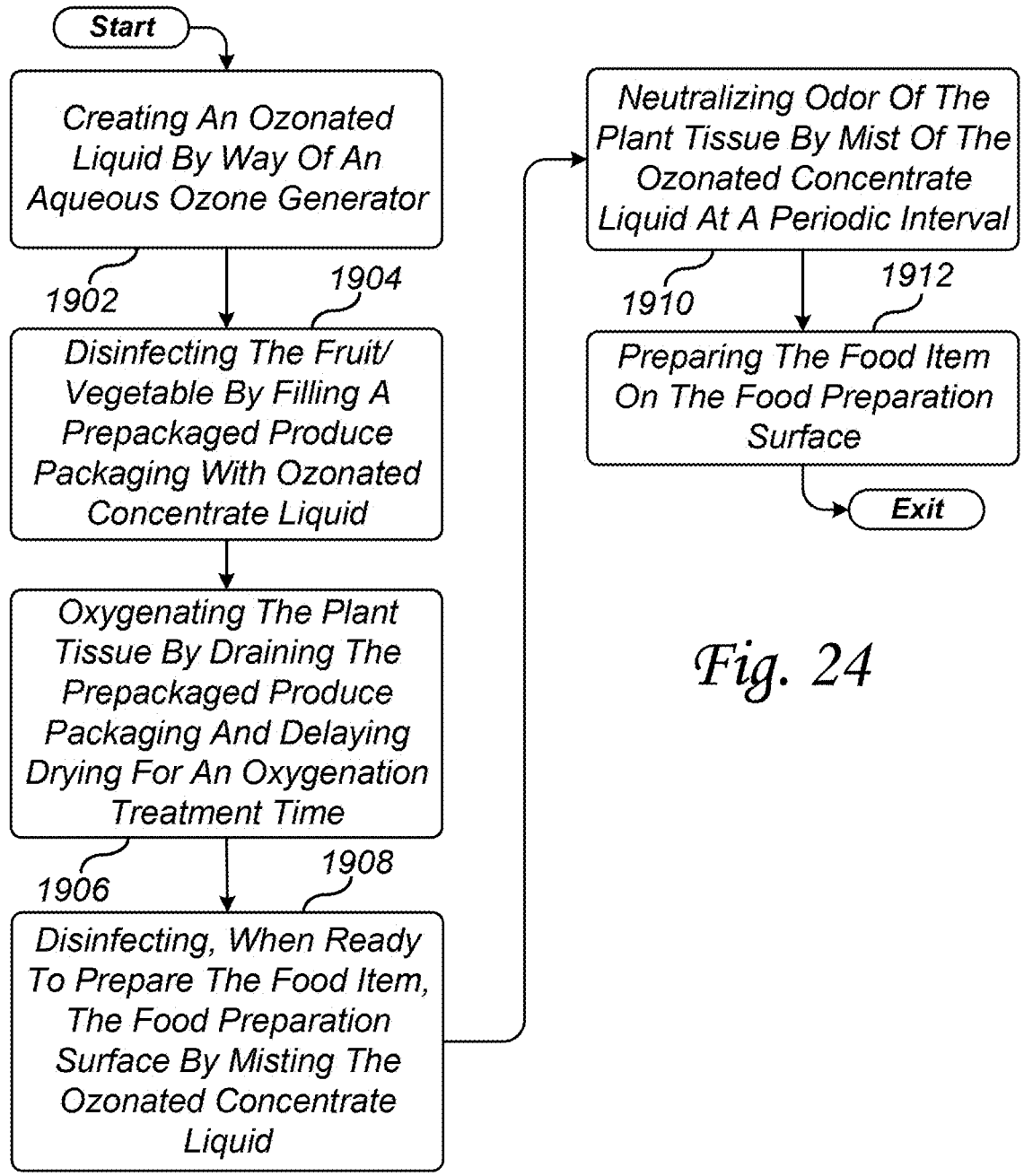

Referring to FIGS. 1H and 24, there is illustrated one example of a food preparation disinfection treatment method. In an exemplary embodiment, a food preparation disinfection treatment method disinfects fruits or vegetables 318, and food preparation surfaces 314 during the preparation of food item 328 in a restaurant 312 environment. In an exemplary embodiment, the method begins in step 1902 by creating an ozonated concentrate liquid 118 by way of an aqueous ozone generator 530. The aqueous ozone generator 530 receives a water source 102 and generates from the water source 102 the ozonated concentrate liquid 118. The method then moves to step 1904.

The method continues in step 1904 by disinfecting one or more fruit 318 or one or more vegetable 318 by filling 478 a prepackaged produce packaging 324, which comprises the fruit 318 or the vegetable 318, with the ozonated concentrate liquid 118, immersing (to fill line 482) the fruit 318 or the vegetable 318 in the ozonated concentrate liquid 118 for a disinfection treatment time 470. Each of the fruit 318 and the vegetable 318 comprises a plant tissue 326. The method then moves to step 1906.

The method continues in step 1906 by oxygenating the plant tissue 326 by draining 480 the prepackaged produce packaging 324 and delaying before drying the fruit 318 or the vegetable 318 for an oxygenation treatment time 472, enhancing metabolic processes of the plant tissue 326. The method then moves to step 1908.

The method continues in step 1908 by disinfecting, when ready to prepare the food item 328, one or more food preparation surface 314 by misting the ozonated concentrate liquid 118 onto the food preparation surface 314 and waiting a surface disinfection treatment time, better illustrated in at least FIG. 1A reference 'B', before using the food preparation surface 314. The method then moves to step 1910.

The method continues in step 1910 by neutralizing the odor of the plant tissue 326 by misting the ozonated concentrate liquid 118 onto the plant tissue 326, at a periodic mist interval 474 and for each of the periodic mist interval 474, a mist duration treatment time. The method then moves to step 1912.

The method continues in step 1912 by preparing the food item 328 on the food preparation surface 314. The food item 328 comprises the fruit 318 or the vegetable 318. The method is then exited.

Referring to FIGS. 1G and 1H, there are illustrated examples of disinfection by immersion and oxygenation by delayed drying. In an exemplary embodiment, FIG. 1G, reference 'A' illustrates a timeline that details how a pesticide residue removal from produce 318 can occur by spraying with the ozonated concentrate liquid 118 for a pesticide residue removal treatment time 468 and that the pesticide residue removal treatment time 468 can be in the range of a few seconds. The produce 318 can then be disinfected by immersion in the ozonated concentrate liquid for disinfection treatment time 470 and the disinfection treatment time can be in the range of less than one minute. The produce 318 can then be oxygenated by delay drying allowing the ozonated concentrate liquid to rest on the plant tissue 326 absent agitation or removal for an oxygenation treatment time 472 and that the oxygenation treatment time 472 can be in the range of greater than one minute and then the produce 318 can be dried. Finally, the produce 318 is misted with the ozonated concentrate liquid at a periodic mist interval 474 and for each of the periodic mist intervals 474, a mist duration treatment time. In an exemplary embodiment, the periodic mist interval 474 can be in the range of hourly to daily or even extending to every two or three days depending on the environmental condition the produce 318 is kept prior to use in a food item 328. Additionally, the mist duration treatment time which is the duration of misting the ozonated concentrated liquid onto the plant tissue 326 can be in the range of a few seconds. In a plurality of exemplary embodiment, treatment time of the various steps above can be adjusted based on the environment and other factors the produce is stored or otherwise maintained prior to use in a food item 328 as may be required and/or desired in a particular embodiment.

An advantage, in the present invention, in an exemplary embodiment, with regards to the steps of disinfection by immersion for a disinfection treatment time 470 and oxygenating by delayed drying for an oxygenation treatment time 472 these steps can be combined 476 with the aid of an immersion bucket 154.

In this regard, and as illustrated in reference 'B' the produce 318 can be placed into the immersion bucket 154 up to the produce fill line 168. The immersion bucket 154 can then be filled with the ozonated concentrate liquid 118 up to the ozonated concentrate liquid fill line 166. In operation, an egress port 164 in the bottom 170 of the immersion bucket 154 is adjustable and configured to allow the ozonated concentrate liquid to drain from the immersion bucket 154 at a time rate 478 which is equivalent to the disinfection treatment time 470. In this regard, without operator intervention the immersion bucket 154 self-drains through the egress port 164 moving 478 the water line from the ozonated concentrate liquid fill line 166 to the produce fill line 168 in the time period equivalent to disinfection treatment time 470 thus keeping the produce 318 immersed in the ozonate concentrate liquid for the disinfection treatment time 470.

The immersion bucket 154 continues to self-drain until all of the ozonated concentrate liquid is drained leaving the produce 318 to rest in a wetted state absent agitation or removal of the surface coating of the ozonated concentrate liquid 118 for the oxygenation treatment time 472. Food service personnel can then remove and dry the produce 318 ready for storage and/or use in preparing food items 328.

Referring to FIG. 1H, reference 'A' a timeline that details how a pesticide residue removal from produce 318 can occur by spraying with the ozonated concentrate liquid 118 for a pesticide residue removal treatment time 468 and that the pesticide residue removal treatment time 468 can be in the range of a few seconds. The produce 318 can then be disinfected by immersion in the ozonated concentrate liquid for disinfection treatment time 470 and the disinfection treatment time can be in the range of less than one minute. The produce 318 can then be oxygenated by delay drying allowing the ozonated concentrate liquid to rest on the plant tissue 326 absent agitation or removal for an oxygenation treatment time 472 and that the oxygenation treatment time 472 can be in the range of greater than one minute and then the produce 318 can be dried. Finally, the produce 318 is misted with the ozonated concentrate liquid at a periodic mist interval 474 and for each of the periodic mist intervals 474, a mist duration treatment time. In an exemplary embodiment, the periodic mist interval 474 can be in the range of hourly to daily or even extending to every two or three days depending on the environmental condition the produce 318 is kept prior to use in a food item 328. Additionally, the mist duration treatment time which is the duration of misting the ozonated concentrated liquid onto the plant tissue 326 can be in the range of a few seconds. In a plurality of exemplary embodiment, treatment time of the various steps above can be adjusted based on the environment and other factors the produce is stored or otherwise maintained prior to use in a food item 328 as may be required and/or desired in a particular embodiment.

An advantage, in the present invention, in an exemplary embodiment, with regards to the steps of disinfection by immersion for a disinfection treatment time 470 and oxygenating by delayed drying for an oxygenation treatment time 472 these steps can be combined 476 with the aid of an immersion bucket 154.

In this regard, prepackaged produce packaging 324 can be opened and the packaging 324 filled 478 with the ozonated concentrate liquid 118 to a fill line 482 immersing the produce 318 for a disinfection treatment time 470. At the conclusion of the disinfection treatment time 470 the packaging 324 can be drained 480 leaving the produce 318 to rest in a wetted state absent agitation or removal of the surface coating of the ozonated concentrate liquid 118 for the oxygenation treatment time 472. Food service personnel can then remove, dry, and/or reseal the produce 318 in the packaging 324 ready for storage and/or use in preparing food items 328.

In an exemplary embodiment, such drying of the lettuce can be by blotting with a towel 320, forced air flow 322, air-drying, spinning the produce 318 in a device to use centripetal force to remove excess water, or by other suitable methods as may be required and or desired in a particular embodiment.

Figure 2A:
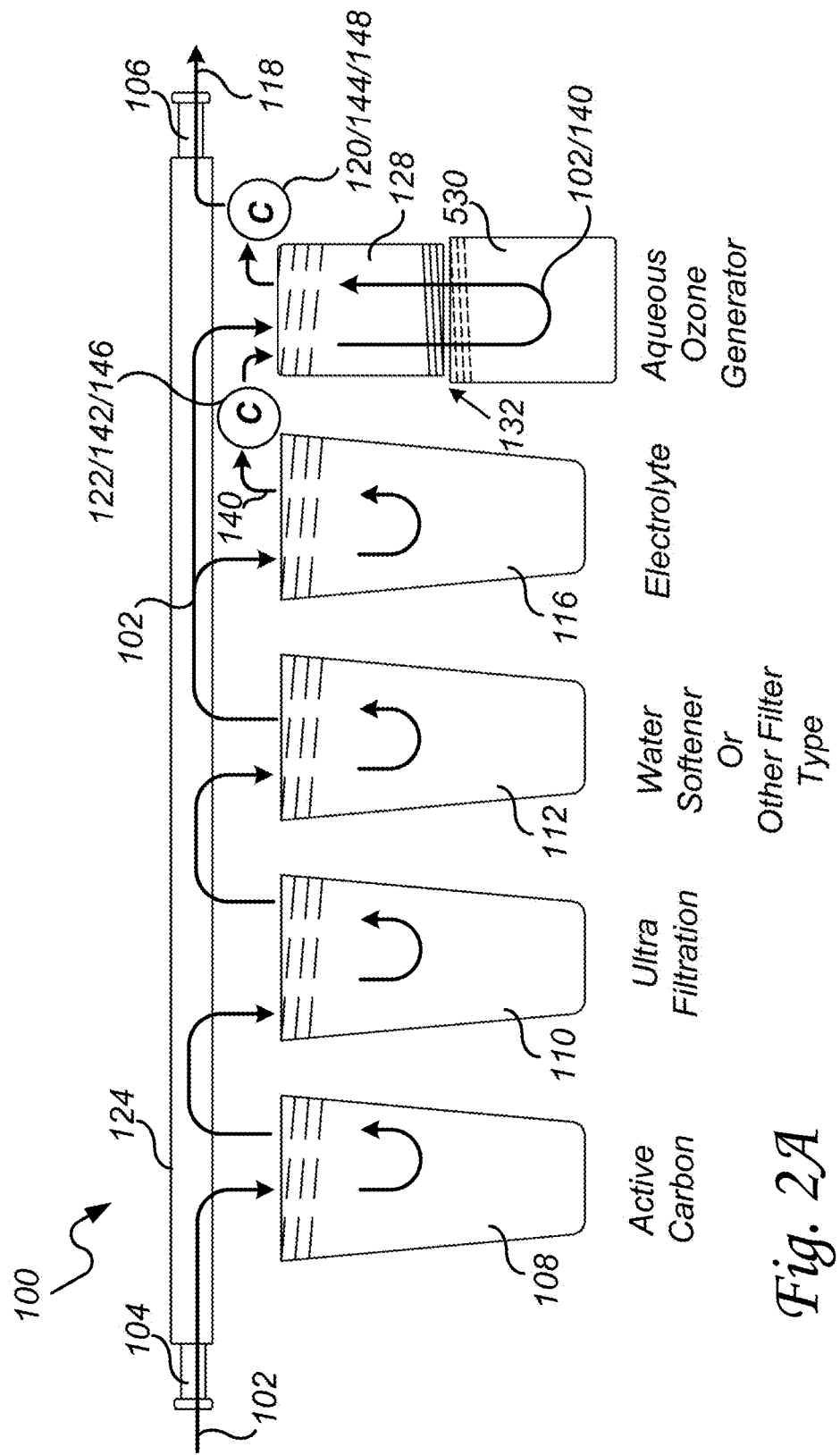
FIGS. 2A-B and 3 illustrate examples of an aqueous ozone disinfection system.

Referring to FIG. 2A, there is illustrated one example of an aqueous ozone ($O_3$) disinfection system 100. In an exemplary embodiment, in applications such as food preparation and other applications, a manifold 124 can be interconnected with a source of water 102. Since water quality can vary, other filters may be in use for various purposes, such as filters 108/110/112 electrochemical generator performance may vary based on the conductivity of the water, as well as other factors. Since electrochemical generation from the water relies, in part, on electrolysis when the water is too soft, indicating low total dissolved solids (TDS), in particular ions, the conductivity of the water between the electrochemical electrodes is poor, causing low current flow between the electrodes and as such electrochemical generation can be impaired.

In operation, to exacerbate the shortcomings of soft water, prefiltering such as active carbon, ultrafine filtration, and other water treatments seek to remove particulates and molecules such as chlorine and others to make the water purer, chemical-free, odor-free, and pathogen-free, it does, however, make it softer (lower TDS ions and less conductive) which is even more unsuitable for electrochemical generation. Furthermore, while clean water in food contact and human consumption applications is a priority the water loses its ability to disinfect primarily by the added chlorine in municipal water. To this end, responsive to low water conductivity conditions, the present invention adjusts the conductivity of the water such that aqueous ozone can be electrochemically produced, in a continuous flow manner, in a predictable rate of production amount and dispensed at a sufficient and reliable ozone concentration level to disinfect food and surfaces that come in contact with the ozonated water.

As an example and not a limitation, such ozone concentrations suitable for food washing and food preparation surfaces can be in the range of 0.5 parts per million (PPM) to 1.5 PPM, or other suitable ozone concentration as may be required and or desired in a particular embodiment.

An advantage, in the present invention, is that soft water conditions that inhibit the electrochemical generation can be mitigated by the dosing of an electrolyte in an amount just needed to adjust the conductivity of the water in order to achieve optimal performance of the electrochemical generation. In addition, the dwell time of the mixture of water and electrolyte, within the aqueous ozone generator 530, can be adjusted to allow sufficient time in which for the electrochemical generator to ozonate the water in a continuous flow manner.

In this regard, the conductivity of the water is improved by a dosing of an electrolyte, in a ratiometric amount, in a continuous flow manner, allowing electrochemical generation of aqueous ozone to be produced at a desired concentration level with varying water input conditions. In operation, the present invention controls the dosing of the amount of electrolyte by way of an electrochemical medium catalyst governor 122/142/146. Additionally, a flow governor 120/144/148 controls the flow rate of the mixture of water and electrolyte through the aqueous ozone generator, in effect controlling the dwell time the electrochemical generator has to produce the ozone at the desired ozone concentration level. In this regard, slowing the mixture flow rate increases the dwell time, and increasing the flow rate decreases the dwell time.

Figure 5:
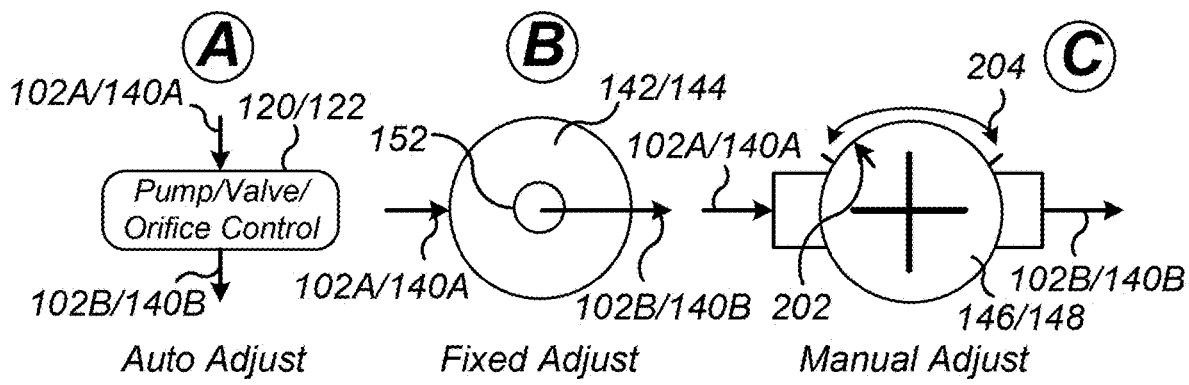
FIG. 5 illustrates examples of electrochemical medium catalyst governors and flow governors.

As better illustrated in at least FIG. 5 governers 120/122 can be an electronic pump/valve/orifice control, each 120/122 of which can be automatically adjusted by way of control system 500. Governers 142/144 can be a fixed adjust washer style with variable size orifice that self-regulated with fluid pressure. Governors 146/148 can be manually adjustable style allowing a technician 302 or other authorized person to manually adjust the dosing rate of the electrolyte 122/142/146 into the water 102 and the mixture of the water and the electrolyte flow rate 120/144/148 controlling the dwell time of the mixture within the aqueous ozone generator 530 in a continuous flow manner. Additionally, other types or kinds of suitable governors can be used, as may be required and/or desired in a particular embodiment.

Figure 2B:
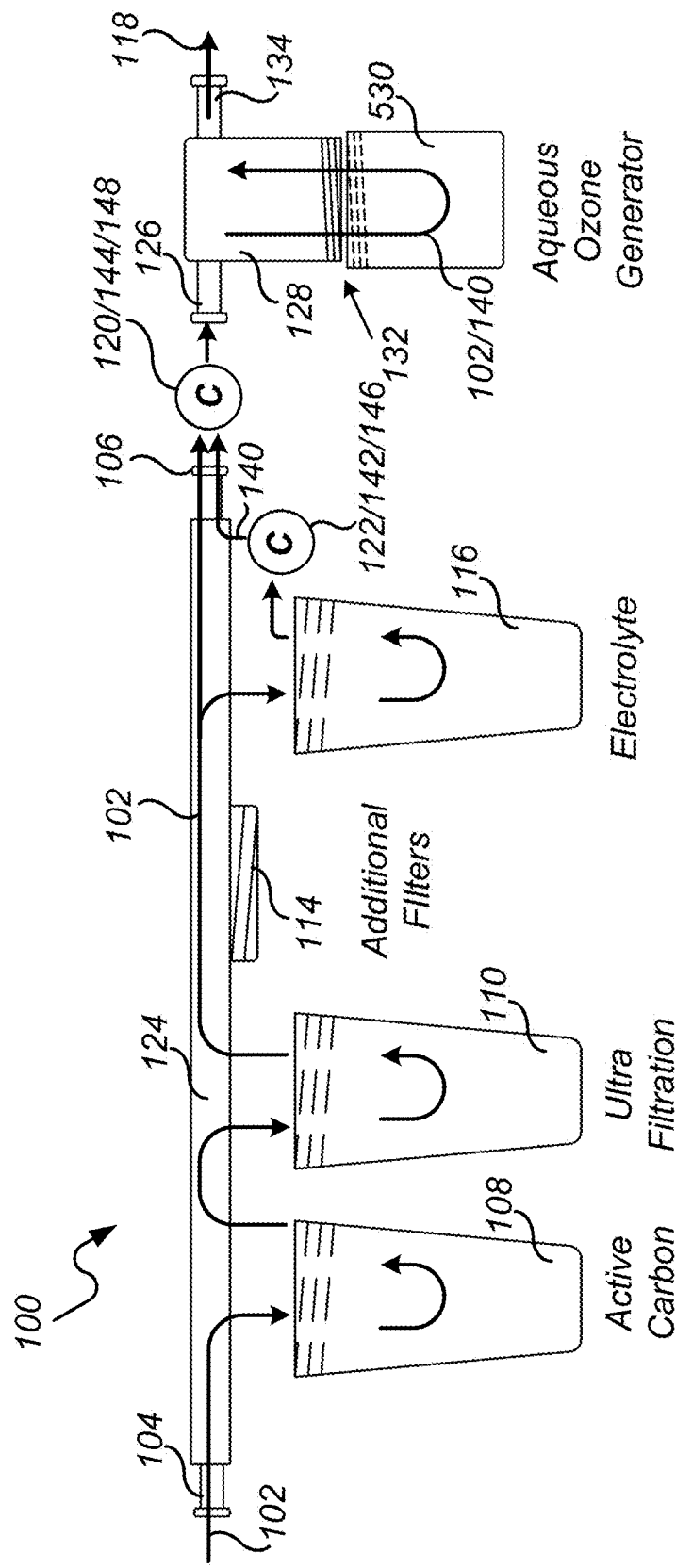

In operation, as better illustrated in at least FIG. 2B, a manifold 124 can have a plurality of cartridge receive adapters 114, in fluid communication, in which one or more compatible filters 108/110/112, electrolyte cartridges 116, aqueous ozone generators 530, or other types and or kinds of compatible cartridges and devices can be attached. In operation, water 102 can enter the manifold 124 and can sequentially pass in and out of each of the filters 108/110/112, electrolyte cartridges 116, aqueous ozone generator 530, or other cartridges. A concentrated ozone liquid 118 is dispensed, in a continuous flow manner, from the manifold 124 and can be used in a disinfecting manner for food washing, food preparation, surface cleaning, and other disinfection cleaning and washing purposes.

An advantage, in the present invention, is that aqueous ozone production happens within water and in the absence of air or oxygen gas traditionally used on corona discharge ozone production. The advantage of aqueous ozone is that it forms ozone $O_3$ molecules in large quantities on demand from the water with the help of an ion exchange material. The ozone molecules are produced in high concentration levels and well distributed throughout the water and tend not to break out of the water which makes the aqueous ozone concentration slow to dissipate with a half-life in the range of 20-30 minutes. In this regard, spraying aqueous ozone on food, food preparation areas and surfaces, food preparation equipment, and in other areas and leaving it undisturbed and/or allowing it to dry slowly means that the ozone treatment time can range from many minutes to tens of minutes. It is the long half-life time of aqueous ozone in combination with treating food and food preparation equipment and surfaces, and other areas at sufficient ozone concentration that enables the present invention to reach achieve oxidation levels in the range of 5 log reduction in pathogens including odor-causing pathogens, disease-causing pathogens, and others on food, food preparation equipment and surface, and in other areas.

In contrast, corona discharge systems create ozone gas (and a bunch of human-harmful nitrogen species molecules) that then has to be dissolved or dispersed into the water at a low concentration level which easily breaks out of the water and dissipates before any real disinfection benefits can be realized on the surface. Additionally, the ozone purity level in aqueous ozone is in the range of 28% whereas corona discharge techniques yield ozone purity in the mid-single digits to low teens with corona discharge in air having lower purity than corona discharge in oxygen.

For disclosure purposes, food washing can include all types of food including vegetables, fruits, meats, and other items. In operation, washing food in ozonated water, of the present invention, disinfects the surface of the food including killing bacteria and other pathogens. An added benefit and advantage, of the present invention, is that food washed/disinfected with ozonated water tends to extend the length of time food stays fresh 1 as food-destroying surface bacteria and other organisms that can rapidly shorten the freshness and quality of the food are neutralized by the ozonated water.

For disclosure purposes food washing, food washing surfaces, and food preparation devices can be generally referred to as food preparation surfaces 204 and are not particularly limited and can include slicing machines, cutting machines, ovens, toasters, microwaves, bins, containers, refrigerators, other devices, surfaces of all kinds including tables, countertops, floors and walls around food preparation areas, and/or other types and kinds of surfaces, as may be required and/or desired in a particular embodiment.

An advantage, in the present, is that varying types of water with varying levels of TDS can be used as input water to the system. In operation, a portion of the input water 102 is mixed with a dosing of the electrolyte 140 (as needed and in an amount needed) in a ratiometrically mixed manner (ratio of water 102 and electrolyte 140) to adjust the conductivity of the mixture of the water 102 and electrolyte 140 such that the electrochemical generator 516 within the aqueous ozone generator 530 can produce aqueous ozone at a desired concentration ($O_3$ ppm) level. Even when the source of water 102 is soft, absent sufficient TDS ion the electrolyte dosing adjusts the conductivity of the water to the desired level for electrochemical production of aqueous ozone at the desired production rate so the ozonated water, in a continuous flow manner, is dispensed at the desired ozone concentration level.

In the present invention the term "ratiometric" or "ratiometrically" is intended to mean a system in which an output is directly proportional to the ratio of two or more inputs. In this regard, the input to an electrochemical generator is a mixture of electrolyte and water in a predetermined ratio and the output is an ozonated concentrate liquid at a desired ozone concentration level. An advantage, in the present invention, is the ozonated concentrate liquid can be produced from water that has low conductivity (high resistance between the electrodes) by ratiometrically mixing it with an electrolyte before electrochemical production. Additionally, the flow rate of the mixture (water and electrolyte) can be controlled to optimize the dwell time within the aqueous ozone generator allowing sufficient time for the electrochemical generator to produce the aqueous ozone at the desired ozone concentration level. This approach is also an advantage as the electrochemical generator ages with use and efficiency begins to change. In this regard, the mixture flow rate can be adjusted to set the dwell time accordingly to extend the useful life of the electrochemical generator.

Another advantage, in the present invention, is that instead of batch-type techniques, no matter what volume of outflow of ozonated water is needed ratiometrically mixing the water and electrolyte as well as controlling the mixture flow rate/dwell time, ozonated water can be produced at the needed volume at the right ozone concentration accurately at any on-demand volume level.

An advantage, in the present invention, is that the aqueous ozone generator 530 produces ozone through water electrolysis and ion exchange techniques. In this regard, part of the aqueous ozone generator 530 can comprise an electrochemical generator 516. During normal operation, the process of generating aqueous ozone can degrade the aqueous ozone generator 530. In addition, water quality can have an impact on the aqueous ozone generator 530 including causing premature scaling of certain components. This creates the need to track the service life of the aqueous ozone generator 530 and components such as the electrochemical generator 516. The present invention does this in a couple of different ways.

In an exemplary embodiment, in one example, technician 302 can test the ozonated water manually data communicating the results by way of computing device 732 such as a laptop, smartphone, tablet, or other suitable computing device for recording on a remote data processing resource 702 such as a server 702. Ozone production, use of the aqueous ozone generator, and ozone concentration levels can then be tracked remotely over time. When data shows that service or replacement is needed notification can be sent to technician 302 or administrator 304 and the aqueous ozone generator 530 serviced or replaced.

In another exemplary embodiment, the control system 500 can comprise an ozone sensor 522 and communication interface 508 that can automatically monitor ozone production and the use of the aqueous ozone generator 530. The results can be data communicated by way of the communication interface 508 to remote data processing resources 702 for recording. When data shows that service or replacement is needed notification can be sent to technician 302 or administrator 304 and the aqueous ozone generator 530 serviced or replaced.

Figure 11:
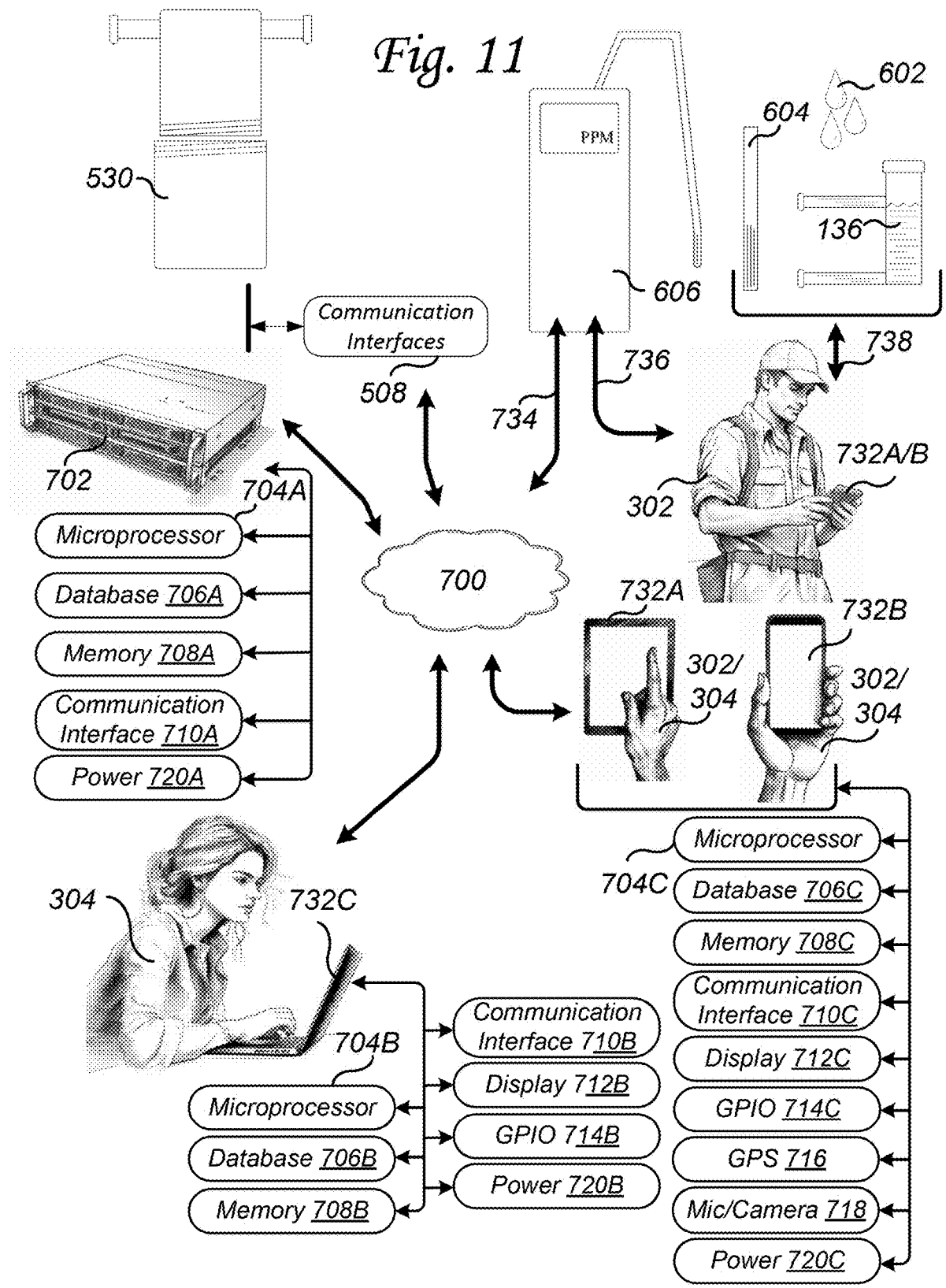
FIG. 11 illustrates one example of a system and network diagram.

Another advantage, in the present invention, and with reference to at least FIG. 11, is that the control system 500 can comprise a global positioning system (GPS) 514. In this regard, the GPS location of the aqueous ozone generator 520 can be tracked, and data communicated by way of the communication interface to the remote data processing resource 702. Reports, maps, and other information can then be used to inform where located, when/how used, and other details related to the aqueous ozone generator 530, as may be required and/or desired in a particular embodiment.

With reference to FIG. 5, there is illustrated a system diagram of the aqueous ozone disinfection system. During operation, water 102 and electrolyte 140 are routed to an aqueous ozone generator 530. Through electrolysis and ion exchange techniques the aqueous ozone generator 530 produces an ozonated concentrate liquid 118. The concentration of the ozonated concentrate liquid 118 can be dispensed through a valve, faucet, nozzle, or other, for disclosure purposes all referred to as a nozzle 142.

In an exemplary embodiment, an aqueous ozone disinfection system 100 can comprise an aqueous ozone generator 530 that receives a portion of a water source 102 and electrolyte 140 and generates from the mixture (water 102 and electrolyte 140 which improves the conductivity of the water (lower resistance between the electrodes, enabling better electrical current flow between the electrodes) and as such aqueous ozone production) an ozonated concentrate liquid 118. Such aqueous ozone production can be by way of an electrochemical generator 516. The electrochemical generator 516 can be integrated into the aqueous ozone generator 530. Additionally, the electrochemical generator 516 can comprise an ion exchange material 534 that facilitates ozone molecule formation/production. In operation, the aqueous ozone generator 530 can use electrolysis in combination with the ion exchange material 534, other coatings, electronic control signals, pulse width modulation, and/or other techniques, technologies, and signal processing to produce an ozonated concentrate liquid in the range of 1 part per million ozone (ppm) or other desired lower limit to 10 ppm or other desired upper limit depending on several factors. Such factors can include the aqueous ozone generator 530, electrochemical generator 516 construction, the quantity of ozonated concentrate liquid 118 produced at a time, the amount of time allowed (dwell time) for the aqueous ozone generator 530 to produce the ozonated concentrate liquid 518, the amount of electrical current passed between electrodes (enhanced by the electrolyte 140) and the surface area of the electrodes, and other factors.

While the type and kind of components in the aqueous ozone generator 530 and in particular the electrochemical generator 516 are selected to promote a maximum service life of the electrochemical generator 516, the process of making ozonated concentrate liquid 118 can consume certain of the materials in the aqueous ozone generator 530 and/or the electrochemical generator 516 thus there is a useful service life of the aqueous ozone generator 530 that needs to be monitored.

In addition, during normal use of the aqueous ozone generator 520 and/or electrochemical generator 517, the type or kind of water used in the generator can influence aqueous ozone production (quantity and production rate) as well as create undesirable scaling of the electrodes which to can adversely impact the production of ozonated concentrate liquid 118.

In an exemplary embodiment, the control system 500 by way of an electrical current sensor 520 can monitor and adjust the electrical current pass between electrodes. In this regard, adjustments to the amount of electrical current supplied to the aqueous ozone generated to overcome minor degradation of consumable electrodes, and other factors that would normally and through the water during aqueous ozone production.

While adjusting the electrical current aids in the generation of consistent and reliable aqueous ozone production at desired ppm concentrations, the control system 500 can determine how much it has to compensate over a nominal state, such as when the aqueous ozone generator 530 was newly installed. Such electrical current monitoring and adjustment details can be reported or otherwise data communicated, by way of communication interface 508, to a remote data processing resource 702 such as a server 702. Such monitoring and tracking of electrical current use and changes over time plus other factors can be used to predict the service life of the aqueous ozone generator 530 and provide notifications to technicians 302 or administrators 304 when it is time to schedule maintenance and/or replacement of the aqueous ozone generator 530.

In addition to predictive maintenance and service life notifications of the aqueous ozone production components, changes in water 102 quality, or detection of water mineral scale buildup on the aqueous ozone generator 530 components can be detected and technicians 302 or administrators 304 can be notified to take the necessary corrective action.

In operation, the predetermined post-hygienic ozone treatment concentration is selected to achieve sterilization or near sterilization conditions, achieving oxidation levels in the range of 5 log reduction in pathogens on the food and food preparation surfaces 204.

Figure 3:
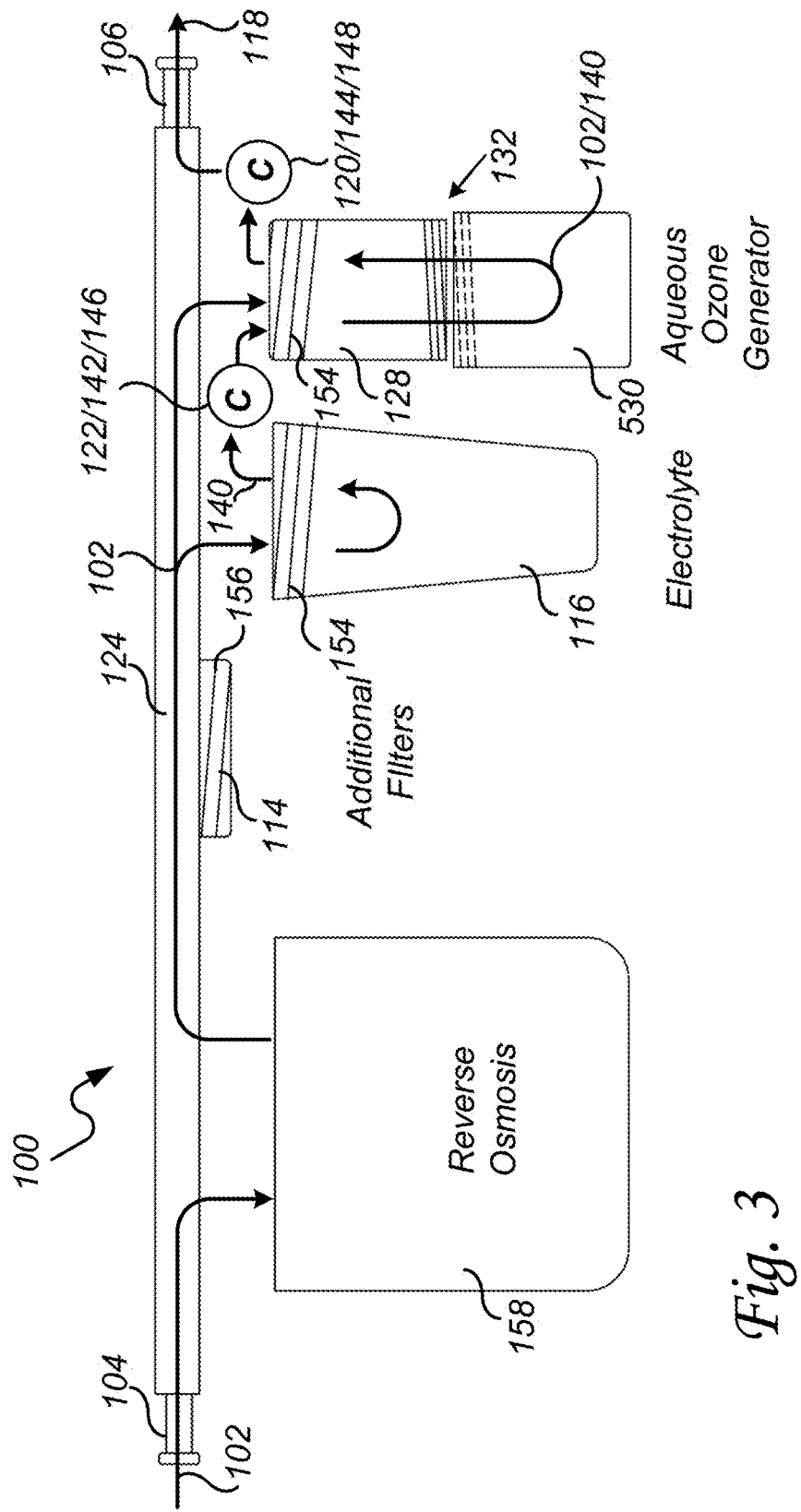

In an exemplary embodiment, and with reference to FIGS. 1-3, an aqueous ozone disinfection system 100 can comprise an aqueous ozone generator 530 that receives water 102 and an electrochemical medium catalyst 140 such as an electrolyte that is combined forming a mixture. As desired, a manifold 124 can provide fluid connectivity to a series of filters 108/110/112 as well as the electrochemical medium catalyst cartridges 116 and the aqueous ozone generator 530. At least FIG. 2B illustrates that the aqueous ozone generator can be separated from the manifold by being fluidly connected. FIG. 3 illustrates that different kinds of water filtration technology such as reverse osmosis devices 158 or other devices can be interconnected with the present invention. In a plurality of exemplary embodiment, combinations of filters 108/110/112, reverse osmosis devices 158, or other water purification and/or filtration devices can be interchangeably used with the present invention.

In operation, such filters and devices can be connected in series, as needed, allowing source water to ingress and egress from each connected filter 108/110/112, and devices 158 to process the inlet water. Once processed, the water 102 then progresses through the electrochemical medium catalyst 140 cartridges and aqueous ozone generator. The manifold 124 can aid in easy connection and disconnect of these filters 108/110/112/devices 158/electrochemical medium catalyst cartridges 116/aqueous ozone generator 530, as may be required and/or desired in a particular embodiment.

Figure 4:
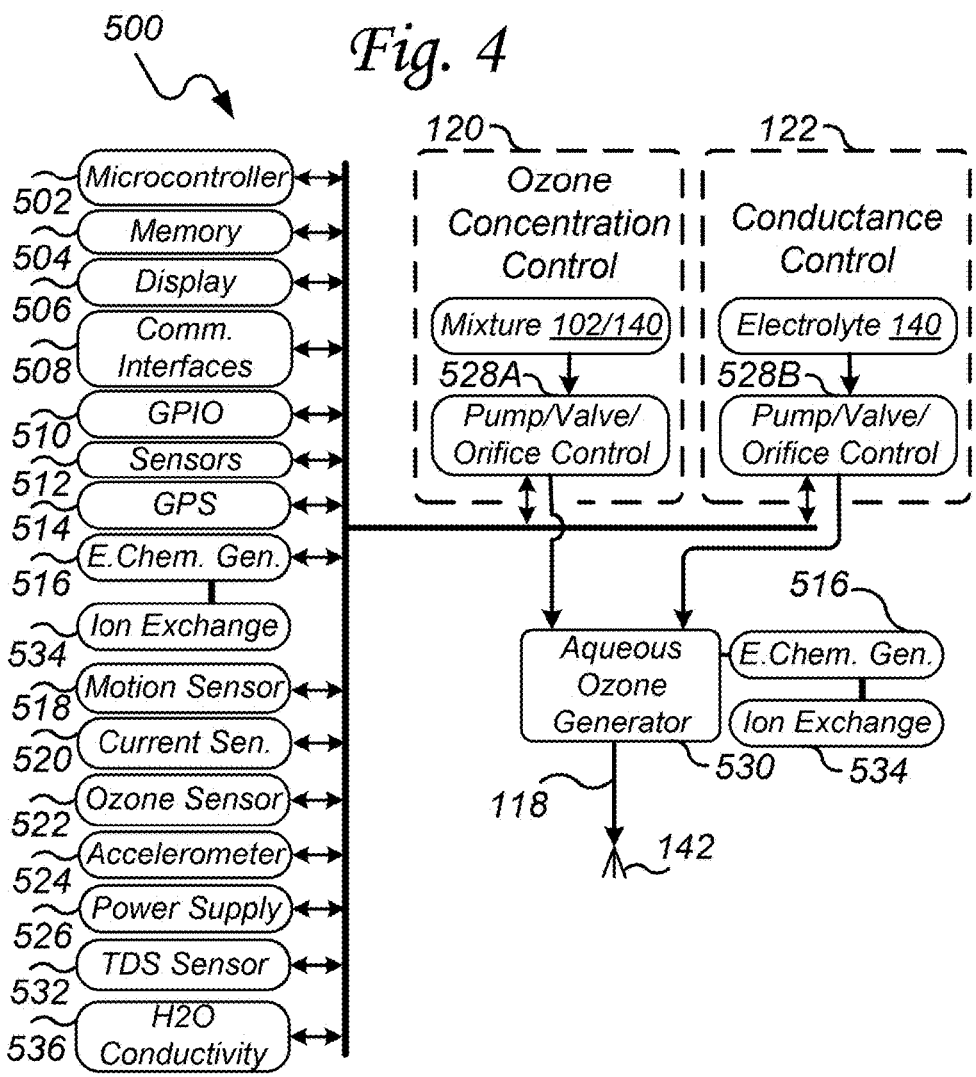
FIG. 4 illustrates one example of a control system for an aqueous ozone disinfection system.

In an exemplary embodiment, and better illustrated in at least FIG. 4, the aqueous ozone disinfection system 100 can further comprise an electrochemical generator 516. The electrochemical generator 516 operates on the mixture of water 102 and the electrochemical medium catalyst 140 to produce aqueous ozone. In this regard, the electrochemical generator 516 can comprise an ion exchange material 534. The electrochemical generator can be integrated into the aqueous ozone generator 530. In operation, the electrochemical generator 516 receives the mixture of water and electrochemical medium catalyst 140 and generates from the mixture an ozonated concentrate liquid.

In an exemplary embodiment, and with reference to FIGS. 1-3 and 5-6, the aqueous ozone disinfection system 100 can also comprise an electrochemical medium catalyst governor 122/142/146. The electrochemical medium catalyst governor 122 regulates the ratiometric mixture of the amount of the electrochemical medium catalyst 140 in the water 102. In this regard, a ratiometric mixture (electrochemical medium catalyst—electrolyte to water) controls the conductivity of the water 102, within a desired conductivity range 430, enhancing electrochemical production of aqueous ozone by the electrochemical generator 516.

In an exemplary embodiment, a flow governor 120/144/148 regulates an aqueous ozone production dwell time which is the amount of time the mixture is inside the aqueous ozone generator 530 being operated on by the electrochemical generator 516. In this regard, the dwell time is the amount of time (aqueous ozone generation time) it takes a portion of the mixture to pass through the electrochemical generator 516. In operation, the dwell time controls an ozone concentration level of the ozonated concentrate liquid within a desired ozone concentration range 440.

In an exemplary embodiment, and with reference to FIGS. 2A-B, and 3, the electrochemical medium catalyst governor 122/142/146 can be positioned to control the amount of electrolyte to flow into the aqueous ozone generator 530. Additionally, the flow governor 120/144/148 can be positioned to control the mixture (water and electrolyte) flow rate (dwell time) through the aqueous ozone generator 530.

In an exemplary embodiment, the electrochemical medium catalyst 140 can be an electrolyte. Such an electrolyte can be potassium bicarbonate KHCO3 or other suitable electrolytes such as Potassium Carbonate (K2CO3), Potassium Citrate, Sodium Bicarbonate (Baking Soda—$NaHCO_3$), or others. For disclosure purposes potassium bicarbonate KHCO3 can also be referred to as potassium hydrogen carbonate, or potassium acid carbonate.

In an exemplary embodiment, preferably potassium bicarbonate can be used. Potassium bicarbonate is an alkaline mineral. The FDA recognizes potassium bicarbonate as a safe substance in bottled water when used appropriately. There are no adverse side effects of this substance in bottled water. Potassium bicarbonate decomposes into $HCO_3^-$, $K^+$, $OH^-$, etc., in an aqueous solution. It is cheaper and more easily soluble in water than food additives containing phosphorus, and used in meat and meat products, dough, and other foods to improve their processing characteristics and flavor.

For disclosure purposes, electrochemical medium catalyst 140 can also be referred to as electrolyte 140.

With reference to FIG. 5, there are illustrated examples of electrochemical medium catalyst governors 122/144/148 controlling the flow of electrolyte 140 and flow governors 120/142/146. In an exemplary embodiment, governers 120/122 can be an electronic pump/valve/orifice control, each 120/122 of which can be automatically adjusted by way of control system 500. Governers 142/144 can be a fixed adjust washer style with variable size orifice that self-regulated with fluid pressure. Governors 146/148 can be manually adjustable style allowing a technician 302 or other authorized person to manually adjust the dosing rate of the electrolyte 122/142/146 into the water 102 and the mixture of the water and the electrolyte flow rate 120/144/148 controlling the dwell time of the mixture within the aqueous ozone generator 530 in a continuous flow manner. Additionally, other types or kinds of suitable governors can be used, as may be required and/or desired in a particular embodiment.

In operation, in an exemplary embodiment, the flow governor can be an orifice washer 142 and can have an orifice hole 152 therethrough through which the flow rate of the mixture (102A+140A) flows through (102B+140B) through the electrochemical generator 516 is controlled. The diameter of the orifice hole 152 can be decreased, resulting in increasing the aqueous ozone production dwell time 442 of the mixture through the electrochemical generator 516, which increases the ozone concentration level of the ozonated concentrate liquid to be within the desired ozone concentration range 440. The diameter can also be increased as appropriate to modulate the ozonated concentration level.

Additionally, an electrochemical medium catalyst governor can be an orifice washer 144 and can have an orifice hole 152 therethrough through which the electrochemical medium catalyst flows 140A/140B. The diameter of the orifice hole 152 can be increased responsive to a decrease in conductivity of the water resulting in an increase in conductivity of the water 102A to within the desired conductivity range 430.

The diameter can also be decreased as appropriate to modulate the conductivity of the water 102 or mixture 102/140.

In another exemplary embodiment, the flow governor 146 can be a manually adjusted valve that has a valve opening therethrough through which the flow rate of the mixture (102A+140A) through (102B+140B) the electrochemical generator 516 can controlled. The diameter of the valve opening can be decreased, by adjusting the manually adjusted valve, resulting in increasing the aqueous ozone production dwell time 442 of the mixture (102+140) through the electrochemical generator 516, which increases the ozone concentration level of the ozonated concentrate liquid to be within the desired ozone concentration range 440. The diameter can also be increased as appropriate to modulate the ozonated concentration level.

In an exemplary embodiment, the electrochemical medium catalyst governor 148 can be a manually adjusted valve that has a valve opening through which the electrochemical medium catalyst flows 140A/140B. In this regard, the valve can be opened to increase, by adjusting the manually adjusted valve 148, responsive to to a decrease in conductivity of the water 102, resulting in an increase in conductivity of the water 102 to within the desired conductivity range 430. The diameter can also be decreased as appropriate to modulate the conductivity of the water 102 or mixture 102/140.

In an exemplary embodiment, the aqueous ozone disinfection system can comprise a manifold 124. The manifold can comprise an inlet 104 that is connected to a source water 102 and more than one cartridge receiving adapter 114. Additionally, an electrolyte cartridge 116 can comprise the electrochemical medium catalyst 140. The electrolyte cartridge 116 can attach to one of the cartridge receiving adapters 114, receive a portion of the water 102, and discharge the electrochemical medium catalyst 140 into the water 102.

Referring to FIG. 4, there is illustrated one example of a control system 500 for an aqueous ozone disinfection system 100. In an exemplary embodiment, control system 500 can be integrated into and be responsive to food washing and food preparation area 204 needs including on-demand and continuous flow of ozonated water for food wash disinfection and food preparation 204 disinfection. In addition, control system 500 can be a web-enabled control system.

The term "web-enabled" or "web-enabled control system" or "web-enabled control system 500" in the present invention is intended to mean an Internet-of-things device. In this regard, a device that is capable of connecting a physical device such as an aqueous ozone disinfection system to the digital world. Stated differently, web-enabling is equipping a device with the necessary electronics to be monitored, and controlled, and data communicate locally and remotely with other data-communicating devices. Such other data-communicating devices can be smartphones, tablets, laptops, mobile communication devices, other web-enabled devices, remote data processing resources, servers, and similar devices.

In addition, and with reference to at least FIG. 11, such data communicating devices 732 can data communicate with remote data processing resources 702 and store and retrieve data from databases 706A-C, and other data processing resources, as may be required and/or desired in a particular embodiment. Laptops, smartphones, smartwatches, tablets, desktop computers, servers, mobile communication devices, and other types and kinds of data communication devices can all be data communicating devices 732 also referred to as computing devices 732.

In operation, a technician 302, an administrator 304, or other authorized people can use computing device 732 to interact with the aqueous ozone generator 100. In this regard, a technician 302 can be a person who operates, maintains, cleans, configures, repairs, and performs other functions on or with the aqueous ozone generator 100 or food wash and/or food preparation surfaces/areas 204. An administrator 304 can be a person who administers, provides remote service or technical support, or be other types or kinds of authorized user, as may be required and/or desired in a particular embodiment.

In an exemplary embodiment, technician 302 can record 736/738 ozone test results and receive data related to the aqueous ozone disinfection system 100. Such test results can be taken or otherwise generated with ozone concentration test implements 602/604/606 which can include an ozone concentration test strip 604, an ozone concentration test drops 602, or an ozone concentration test device 606 to test for dissolved ozone, or other types and/or kinds of ozone concentration test implement. Technician 302 can manually enter the test results in a computing device 732A/B. As better illustrated in at least FIG. 13, a software application or website can be used in combination with the computing device 732A/B to identify the aqueous ozone disinfection system 100, record the test results, and see other useful data by way of data communicating with a remote data processing resource 702. In some embodiments, certain ozone concentration test devices 606 may have the ability to data communicate 734 directly with a remote data processing resource 702, eliminating the need for computing device 732A/B to act as an intermediary device to record test results on the remote data processing resource 702.

Such data processing resources can be servers or other types and kinds of data processing resources. Furthermore, data communicating devices 732, remote data processing resources 702, data storage resources 706A-C, and other types and kinds of data communicating devices can data communicate over a global network 700. The Internet is a global network 700.

In an exemplary embodiment and with reference to at least FIG. 2B, the aqueous ozone generator 100 can be equipped with a web-enabled control system 500. Such a web-enabled control system 500 can comprise a microcontroller 502 which is operationally related to a memory 504, a display 506, a plurality of communication interfaces 508, general purpose input and outputs (GPIO), a plurality of sensors 512, a global position system (GPS) 514, an electrochemical generator 516, a plurality of motion sensors 518, a plurality of electrical current sensors 520, a plurality of ozone sensors 522, an accelerometer 524, a power supply 526, one or more TDS Sensor, one or more water conductivity sensor, a plurality of pumps/valves 528A-B, and an aqueous ozone generator 530.

The microcontroller 502 can be INTEL, ZILOG, MICROCHIP, AMD, ARM, and/or other types or kinds of microcontrollers.

The memory 504 can be a combination of RAM, ROM, flash, hard drives, solid-state drives, USB flash drives, and/or other types and kinds of memory.

The display 506 can be an LCD, OLED, LED, as well as have touch input capabilities and/or other types and kinds of displays and user inputs as may be required and/or desired in a particular embodiment.

The communication interface 508 can be LAN, WAN, USB, Ethernet, RS232, RS485, serial, WiFi, 802.11abgn and similar, 2G 3G 4G 5G compatible, Bluetooth, TCP, UDP, Mesh Network, Zigbee, Pico Network, LORAN, and/or other types and kinds of communication interfaces and protocols.

In an exemplary embodiment, the communication interface 508 is operationally related to the microcontroller 502. The control system by way of the communication interface 508 data communicates with the remote data processing resource 702, data communication devices 732, and other data processing resources in a local area network environment or a wide area network environment across a global network 700 in a wired or wireless manner as may be required and/or desired in a particular embodiment. The Internet is a global network 700.

The GPIO 510 can be TTL, CMOS, transistors, buffers, relays, pushbuttons, switches, and/or other types and kinds of GPIO circuits.

The sensors 512 and/motion sensor 518 can be passive infrared (PIR) motion sensors, infrared, thermal, Doppler radar, ultrasonic, capacitance, touch-type, optical, Hall effect, switch, fingerprint, and other types of biometric sensors, and/or other types and kinds of sensors. Additionally, sensor 512 can be ambient condition sensors such as temperature, moisture, humidity, sunlight, and/or other types and kinds of sensors.

In an exemplary embodiment, analog-type sensor determinations can be converted to digital values so that the microcontroller 502 can process the data. Alternatively, the microcontroller 502 can perform analog-to-digital conversions if equipped to perform such functions.

The electrochemical generator 516 can be an electrolysis-based device that utilizes ion exchange material 534 and other devices and processes to produce chemical compounds from water such as ozone $O_3$.

The current sensor 520 can be configured to measure the supply electrical current to the electrochemical generator 516, the aqueous ozone generator 530, a combination 516/530 thereof, and/or other devices and systems, as may be required and/or desired in a particular embodiment.

The ozone sensor 522 can be configured to monitor the ozone concentration of the ozonated concentrate liquid 118, as may be required and/or desired in a particular embodiment.

The accelerometer 524 can be configured to monitor the motion systems and devices, as required and/or desired in a particular embodiment.

The power supply 526 can be AC, DC, battery, solar, and/or other types and kinds of power supplies.

The total dissolved solids (TDS) sensor 532 can be a conductivity-based sensor or other types or kinds of TDS sensor, as may be required and/or desired in a particular embodiment.

The water conductivity sensor 536 can be a contacting, inductive, or other types or kinds of TDS sensor, as may be required and/or desired in a particular embodiment.

The pumps and/or valves 528A-B, in addition to performing their fluid handling tasks, can be actuated and/or controlled by way of a relay, MOSFET, or other types and kinds of controlling devices. In addition, other pumps and/or valves 528/532 can be integrated into the system as may be required and/or desired in a particular embodiment.

The aqueous ozone generator 530 receives water 102 and electrolyte 140 as an input and uses the electrochemical generator 516 which is integrated into the aqueous ozone generator 530 to produce high concentrations of aqueous ozone molecules. Such concentrations of aqueous ozone can range from 1 ppm to 10 ppm or other desired range, as may be required and/or desired in a particular embodiment.

In an exemplary embodiment, a user interface for the aqueous ozone disinfection system 100 comprises at least one of the following a display 506, a display 506 with touchscreen, a communication interface 508 configured to data communicate with a remote data processing resource 702 such as a server 702 and/or a computing device 732.

The user interface for the aqueous ozone disinfection system 100 can further comprise a plurality of button input capabilities by way of the GPIO 510, or other user interfaces. The user interface is operationally related to the microcontroller 502.

In an exemplary embodiment, and with reference to FIG. 4, the aqueous ozone disinfection system 100 can comprise a control system 500. The control system 500 can comprise a microcontroller 502, a memory 504, the electrochemical generator 516, a first orifice control 528B which controls the diameter of a first orifice through which the electrochemical medium catalyst 140 flows, and a second orifice control 528A which controls the diameter of a second orifice through which the flow rate of the mixture (water 102+ electrochemical medium catalyst 140) through the electrochemical generator 516 is controlled. The microcontroller 502 is operationally related to the memory 504, the electrochemical generator 516, the first orifice 528B, and the second orifice 528A.

In operation, the memory 504 can be encoded with instructions that when executed by the microcontroller 502 perform the steps of increasing the diameter of the first orifice by way of the first orifice control 528B, responsive to a decrease in conductivity of the water 100, resulting in an increase in the conductivity of the water 102 to within the desired conductivity range 430.

The steps continue by decreasing the diameter of the second orifice by way of the second orifice control 528A, resulting in an increase in the aqueous ozone production dwell time 442 of the mixture through the electrochemical generator 516, which increases the ozone concentration level of the ozonated concentrate liquid 118 to be within the desired ozone concentration range 440.

In another exemplary embodiment, the control system can comprise an ozone sensor 522 and a water conductivity sensor 536. The ozone sensor 522 and the water conductivity sensor 536 can be operationally related to the microcontroller 502. In operation, the memory can be encoded with instructions that when executed by the microcontroller perform the steps of determining the conductivity of the water 102 by way of the conductivity sensor 536 and determining the ozone concentration level of the ozonated concentrate liquid 118 by way of the ozone sensor 522. In this regard, both the water conductivity of the water and/or mixture (water 102+electrolyte 140) and the ozone concentration of the concentrated ozone liquid 118 can be determined by sensors, as may be required and/or desired in a particular embodiment.

In an exemplary embodiment, the control system 500 can comprise a communication interface 508 that is operationally related to the microcontroller 502. The memory 504 can be encoded with instructions that when executed by the microcontroller 502 perform the steps of data communication, by way of the communication interface 508, the ozone concentration level of the ozonated concentrate liquid 118, or conductivity of the water 102 or the mixture (water 102+electrolyte 140) to a remote data processing resource 702. The steps continue by receiving, from the remote data processing resource 702, by way of the communication interface 508 a plurality of aqueous ozone generator service life data. Such service life data can include install date, installed equipment, location, number of service hours, other operating conditions, and other types and/or kinds of service life data, as may be required and/or desired in a particular embodiment.

Figure 6:
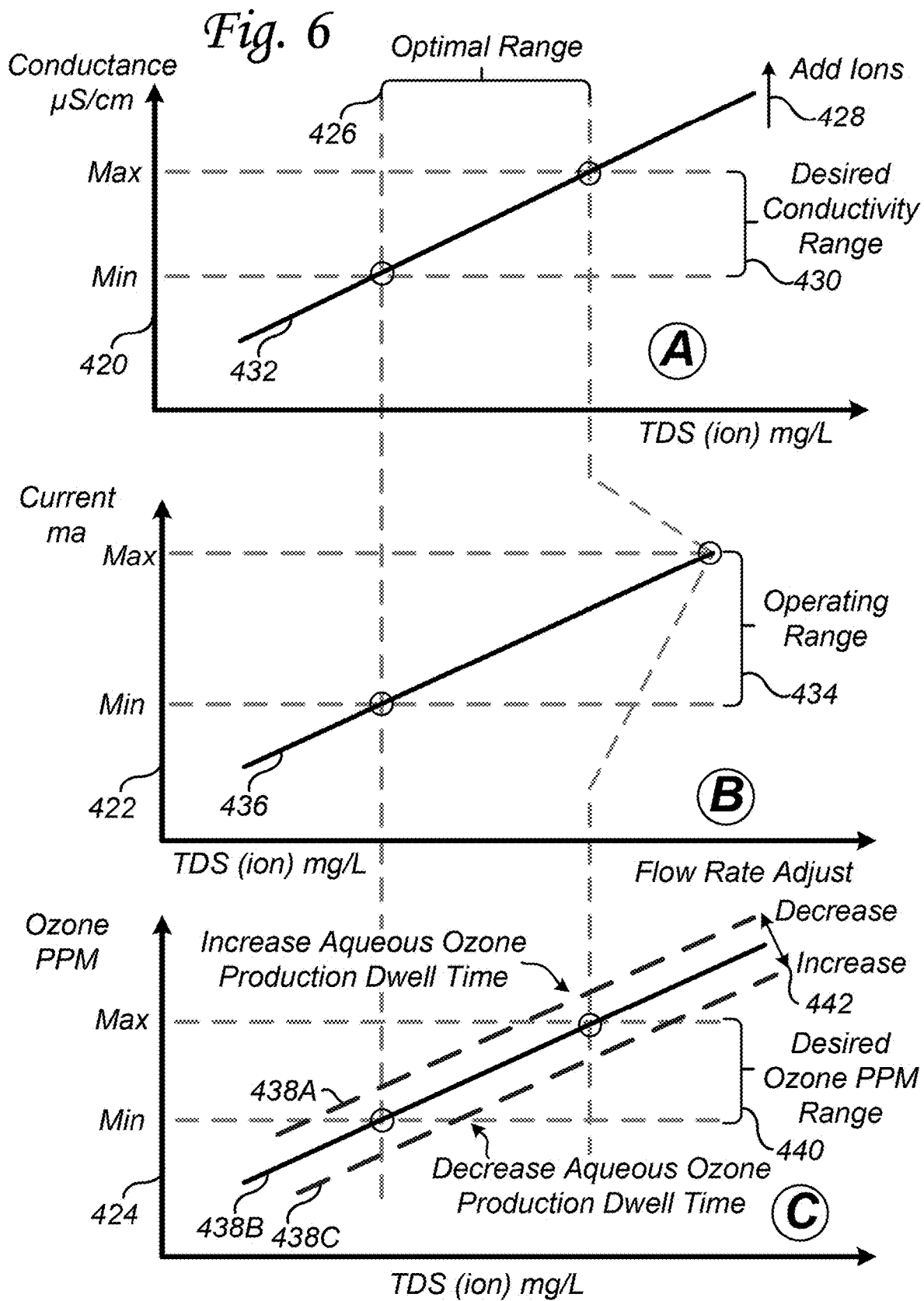
FIG. 6 illustrates one example of the relationship between water conductance, electrical current, and ozone concentration of the concentrated ozone liquid.

Referring to FIG. 6, there is illustrated one example of the relationship between water conductance 420, electrical current 422, and ozone concentration 424 of the concentrated ozone liquid. In an exemplary embodiment, there is an optimal range 426 between water conductance 420, electrical current 422 that flows between the electrochemical generator electrodes through the water, and ozone concentration 424.

In reference 'A', since input water conditions can vary and soft water (low ions) can be particularly difficult to work with, the present invention can dose an electrolyte 140 adding ions 428 into the water 102 to improve water conductivity, keeping it within a desired conductivity range 430.

In reference 'B', the control system 500 including the electrochemical generator 516 is designed to operate between a minimum and a maximum operating range 434 of electrical current that passes through the water mixture.

In reference 'C', the desired ozone ppm range 440 of the ozonated concentrate liquid 118 is selected to achieve the desired disinfection level and/or desired log reduction. As an example and not a limitation, ozonated concentrate liquid 118 with a concentration level between a minimum 0.5 ppm and a maximum 1.5 ppm is often desired for food wash and food preparation surface 204 disinfection, though other concentrations can be selected, as may be required, and/or desired in a particular embodiment. To adjust the ozonated concentration 438A-C the mixture 102/140 flow rate can be adjusted 442. In this regard, decreasing the flow rate allows the electrochemical generator 516 to operate on each portion of the mixture 102/140 longer increasing 438A the aqueous ozone concentration. Conversely, increasing the flow rate of the mixture 102/140 reduces the amount of time the electrochemical generator 516 has to operate on each portion of the mixture 102/140, decreasing 438C the aqueous ozone concentration.

In operation, the control system 500 and electrochemical generator 516 can modulate the current 436 flow through the mixture 102/140 between the minimum and maximum. In this regard, automatically adjusting, in a constant current manner, based on the conductance of the mixture 102/140.

The variable of water conductance is managed by the dosing of the electrolyte 140. As the electrical current applied by the electrochemical generator 156 begins to reach the maximum operating range 434, the control system 500 and/or orifice setting of the electrolyte 140 can be changed to add more electrolyte to the water improving mixture conductance and the control system can reduce or other modulate the electrical current applied to the mixtures to operate in range. Conversely, too much electrolyte is not needed, and as such dosing can be reduced as needed and the electrical current modulated accordingly.

The variable of ozone concentration can be controlled by adjusting the flow rate of the mixture 102/140 which adjusts the dwell time of the mixture passing through the aqueous ozone generator 530 including the electrochemical generator 516, in a continuous flow manner. Such can be controlled by modulating an orifice size either fixed, manual, or controlled by the control system 500 and associated pumps/valves/orifices.

During normal operation conditions, each of the water conductance 420, electrical current 422, and ozone concentration 424 are operating within the optimal range 426. When a circumstance occurs where the aqueous ozone disinfection system 100 can't compensate to keep the parameters within the optimal range 426 an alarm condition can be triggered, notifications displayed locally of the alarm condition, and the alarm condition can be data communicated remotely to a data processing resource 702. Such alarm conditions can occur when the supply of electrolytes runs out, the electrochemical generator is at an end or service life, scale buildup on the electrodes prevents satisfactory operation, or for other reasons.

Figure 7:
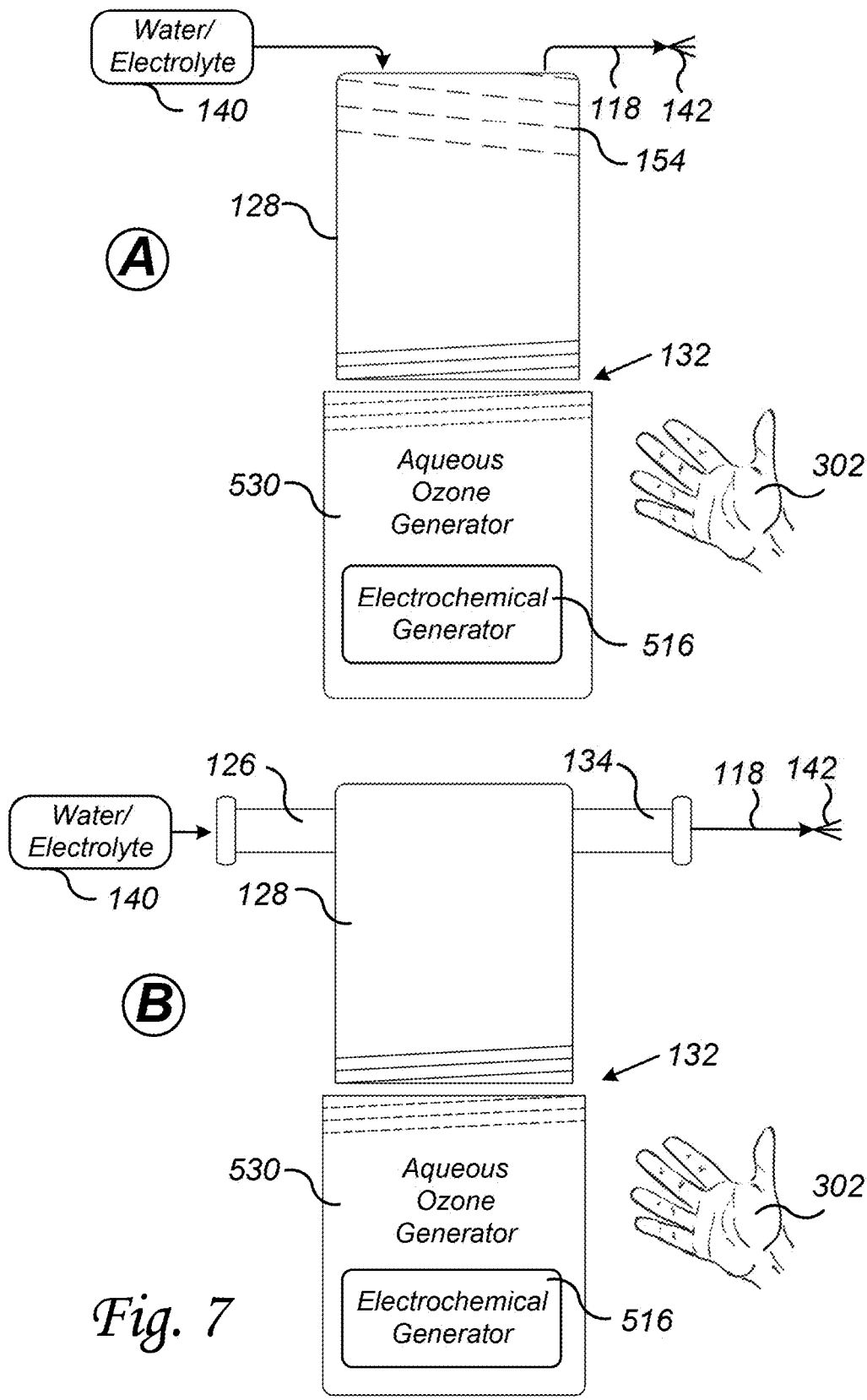
FIG. 7 illustrates one example of a plumbed housing interconnected with an aqueous ozone generator configured housing.

Referring to FIG. 7, there are illustrated examples of a plumbed housing 128 interconnected with an aqueous ozone generator 530. In an exemplary embodiment, in reference 'A' the plumbed housing 128 can be configured to attach to manifold 124 by way of a cartridge receiving adapter 114. In this regard, the filter 108/110/112, the electrochemical medium catalyst 140 cartridges, and/or the aqueous ozone generator 530 can by way of attachment threads 156/158, or other suitable methods attach, in a removable manner to the cartridge receiving adapter 114 allowing ingress and egress of fluids between the manifold and the filters/cartridges/aqueous ozone generator without leaks.

In reference 'B', In an exemplary and exemplary embodiment while some of the filters and cartridges may attached to a manifold 124 cartridge receiving adapter 114 the aqueous ozone generator 520 can be attached by inlet 126 to the manifold 124 by tube, pipe, or other suitable methods. Additionally, outlet 134 can be plumbed as necessary to deliver the concentrated ozone liquid 118 through nozzle 142 or other dispense points to effectuate food wash disinfection, food preparation surface 204 disinfection, and for other purposes, as may be required and/or desired in a particular embodiment.

In an exemplary embodiment, aqueous ozone production involves electrolysis and an ion exchange material 534 which consumes certain components and materials during the process. Thus, when the service life of the aqueous ozone generator 530 and/or electrochemical generator 516 is over the generators 516/530 need to be replaced. To ease and speed generator 516/530 exchange by technician 302 a plumbed housing 128 can be permanently plumbed or otherwise fastened in place and the aqueous ozone generator 530 screwed 132 on to or otherwise fastened 132 in a removable manner to the plumbed housing 128. In this regard, the aqueous ozone generator 530 can be easily and quickly removed and exchanged for a new aqueous ozone generator 530 and electrochemical generator 516 when the aqueous ozone generator 530 and/or electrochemical generator 516 need to be replaced.

An advantage, in the present invention, is that once the plumbed housing 128 is installed and the liquid lines connected, the liquid lines don't need to be removed or disconnected to change the aqueous ozone generator 530. This saves technician 302 time, and cost, and reduces the chance of creating leaks in the system by having to disconnect/reconnect liquid carrying hoses.

In an exemplary embodiment, in operation, a plumbed housing 128 is fastened in fluid communication pathways with the inlet of the mixture (water 102+electrolyte 140) and the outlet of the ozonated concentrate liquid 118. An electrochemical generator 516 is integrated into the aqueous ozone generator 530. The electrochemical generator 516 comprises an ion exchange material 534. The aqueous ozone generator 530 is interchangeable and removably fastened to the plumbed housing 128.

In an exemplary embodiment, an electrochemical generator 516 can be integrated into the aqueous ozone generator 530. The electrochemical generator comprises an ion exchange material 534. A computing device 732, operated by technician 302, can data communicate the test ozone concentration to a remote data processing resource 702, and receive from the remote data processing resource 702, by way of the computing device 732 a plurality of aqueous ozone generator service life data that corresponds to the remaining service life 826 of the electrochemical generator 516.

In an exemplary embodiment, the aqueous ozone generator 530 can comprise a plumbed housing 128 that is fastened in fluid communication pathways with the inlet of the water 102 or the mixture 102/140 and discharge of the ozonated concentrate liquid 118. The aqueous ozone generator 530 can be interchangeable and removably fastened to the plumbed housing 128.

Figure 8:
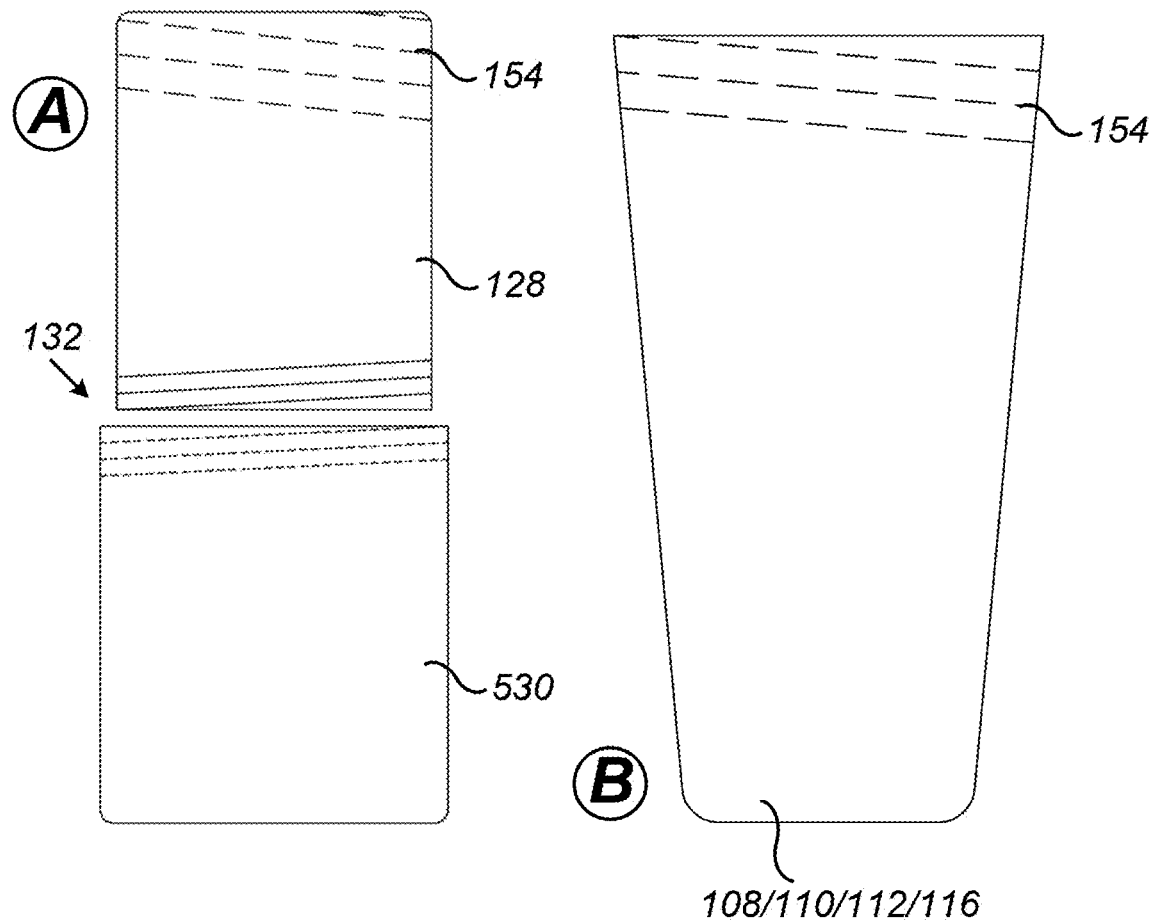
FIG. 8 illustrates examples of attaching a plumbed housing to a manifold.

Referring to FIG. 8, there is illustrated a plumbed housing 128 to a manifold. In an exemplary embodiment, in references 'A' and 'C' the aqueous ozone generator 530 plumbed housing 128 can attach 154 to the onto the manifold 124 cartridges receiving adapter 114/156 by threaded connection, lock in a bayonet style, slide on the plumbed housing and rotate to lock, or interconnect in other suitable ways, as may be required and or desired in a particular embodiment. In reference 'B', the coupling end of the plumbed housing 128/154 of the aqueous ozone generator, the cartridge receiving adapter 114/156, the filters 108/110/112/154, electrochemical medium catalyst cartridges 116/154, and other filters, devices, and components can be sized similarly and attached in a similar manner such that each can be interchangeably attached in a removable manner to the manifold 114 cartridges receiving adapter 114/156.

In an exemplary embodiment, an aqueous ozone disinfection system 100 can comprise a manifold 124. The manifold 124 can comprise an inlet 104 that receives water and more than one cartridge receiving adapter 114. Additionally, an electrolyte cartridge 116 can comprise an electrochemical medium catalyst 140. The electrolyte cartridge 116 attaches to one of the cartridges receiving adapter 114, receives a portion of the water 102, and discharges a mixture of an electrochemical medium catalyst 140 and water 102.

Continuing, an aqueous ozone generator 530 receives the mixture 102/140, and an electrochemical generator 516. The electrochemical generator 516 can comprise an ion exchange material 534. The electrochemical generator 516 can be integrated into the aqueous ozone generator 530. The electrochemical generator 516 receives the mixture 102/140 and generates from the mixture 102/140 an ozonated concentrate liquid 118.

Continuing, an electrochemical medium catalyst governor 122/144/148 regulates ratiometric mixture of the amount of the electrochemical medium catalyst 140 in the water 102, controlling the conductivity of the water 102, within a desired conductivity range 430, and enhancing the electrochemical production of aqueous ozone by the electrochemical generator 516. A flow governor 120/142/146 regulates an aqueous ozone production dwell time 442 of the mixture 102/140 through the electrochemical generator (in a continuous flow manner), controlling an ozone concentration level of the ozonated concentrate liquid 118 within a desired ozone concentration range 440.

Figure 9:
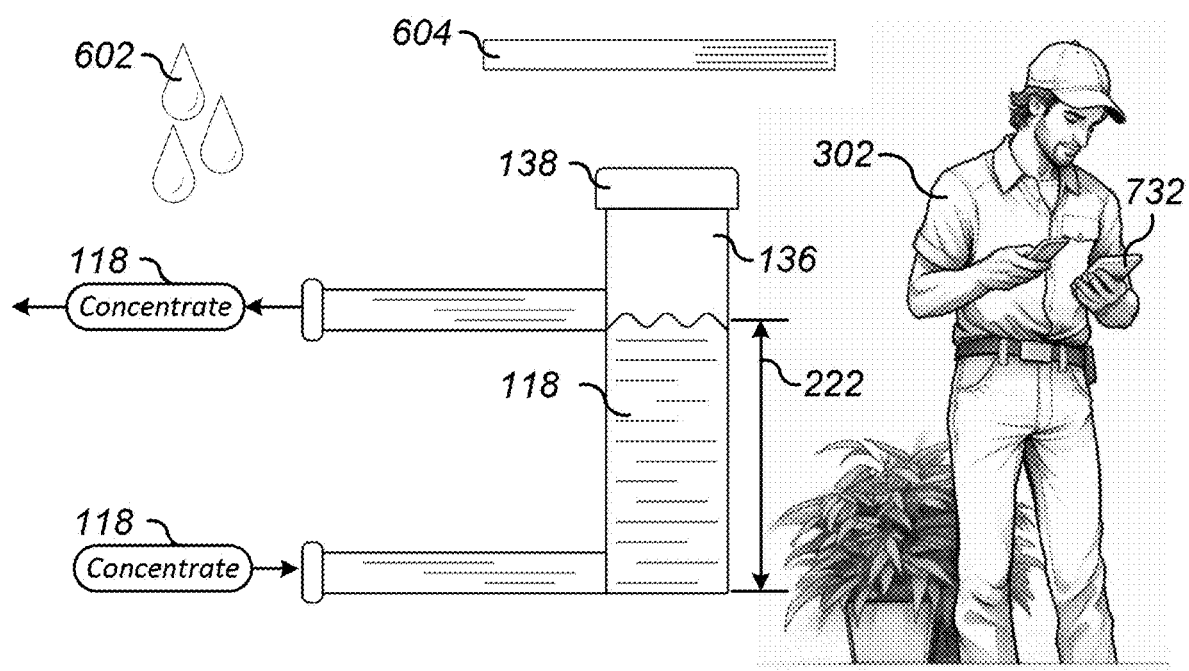
FIG. 9 illustrates one example of a fixed-volume inspection chamber.

Referring to FIG. 9, there is illustrated one example of a fixed-volume inspection chamber 136. In an exemplary embodiment, a fixed-volume inspection chamber 136 receives a continuous flow and maintains a fixed-volume portion 222 of the ozonated concentrate liquid 118, or other ozonated flow. The amount 222 of the fixed-volume is predetermined by test requirements of an ozone concentration test implement 602/604/606. Such amount 222 can be in the range of 200 milliliters (ml), or other amount as may be required and/or desired in a particular embodiment.

In a plurality of exemplary embodiments, more than one of the fixed-volume inspection chambers 136 can be used in an embodiment. In this regard, the fixed-volume inspection chambers 136 can incorporated at several places throughout the system 100 so that dissolved ozone concentrations can be checked. Such places can include ozonated concentrate liquid 118 lines or other places throughout system 100 as may be required and/or desired in a particular embodiment.

In operation, the ozone concentration test implement 602/604/606 can include an ozone concentration test strip 604, an ozone concentration test drops 602, or an ozone concentration test device 606 to test for dissolved ozone, or other types and/or kinds of ozone concentration test implement. The ozone concentration test implements 602/604/606 can be manually used by technician 302 to determine a test ozone concentration of the ozonated concentrate liquid 118 by inserting the ozone concentration implement 602/604/606 into the fixed-volume inspection chamber 136 and then reading the test ozone concentration of ozonated concentrate liquid within.

For disclosure purposes, such ozone concentration test strip 604 can be SENSAFE type or brand, MACHERY-NAGEL type or brand, or other suitable types or brands. Such ozone concentration test drops 602 can be CHEMETRICS type or brand, or other suitable types or brands.

In an exemplary embodiment, where access to the ozonated concentrate liquid 118 within the fixed-volume inspection chamber 136 is required an inspection chamber lid 138 can be configured to be open and closable as required and/or desired in a particular embodiment.

In an exemplary embodiment, a fixed-volume inspection chamber 136 receives a continuous flow and maintains a fixed-volume portion 222 of the ozonated concentrate liquid 118. The amount of the fixed-volume portion 222 is predetermined by the test requirements of an ozone concentration test implement 602/604/604.

In a plurality of exemplary embodiments, more than one of the fixed-volume inspection chambers 136 can be used in an embodiment. In this regard, the fixed-volume inspection chamber 136 can be incorporated at several places throughout system 100 so that dissolved ozone concentrations can be checked. Such places can include ozonated concentrate liquid 118 lines or other places throughout system 100 as may be required and/or desired in a particular embodiment.

In operation, the ozone concentration test implement 602/604/606 can include an ozone concentration test strip 604, an ozone concentration test drops 602, an ozone concentration test device 606 to test for dissolved ozone or other suitable ozone concentration test implement. The ozone concentration test implements 602/604/606 are manually used by technician 302 to determine a test ozone concentration of the ozonated concentrate liquid within the fixed-volume inspection chamber 136 by inserting the ozone concentration implement 602/604/606 into the fixed-volume inspection chamber 136 and then reading the test ozone concentration of ozonated concentrate liquid 118 within.

Figure 13:
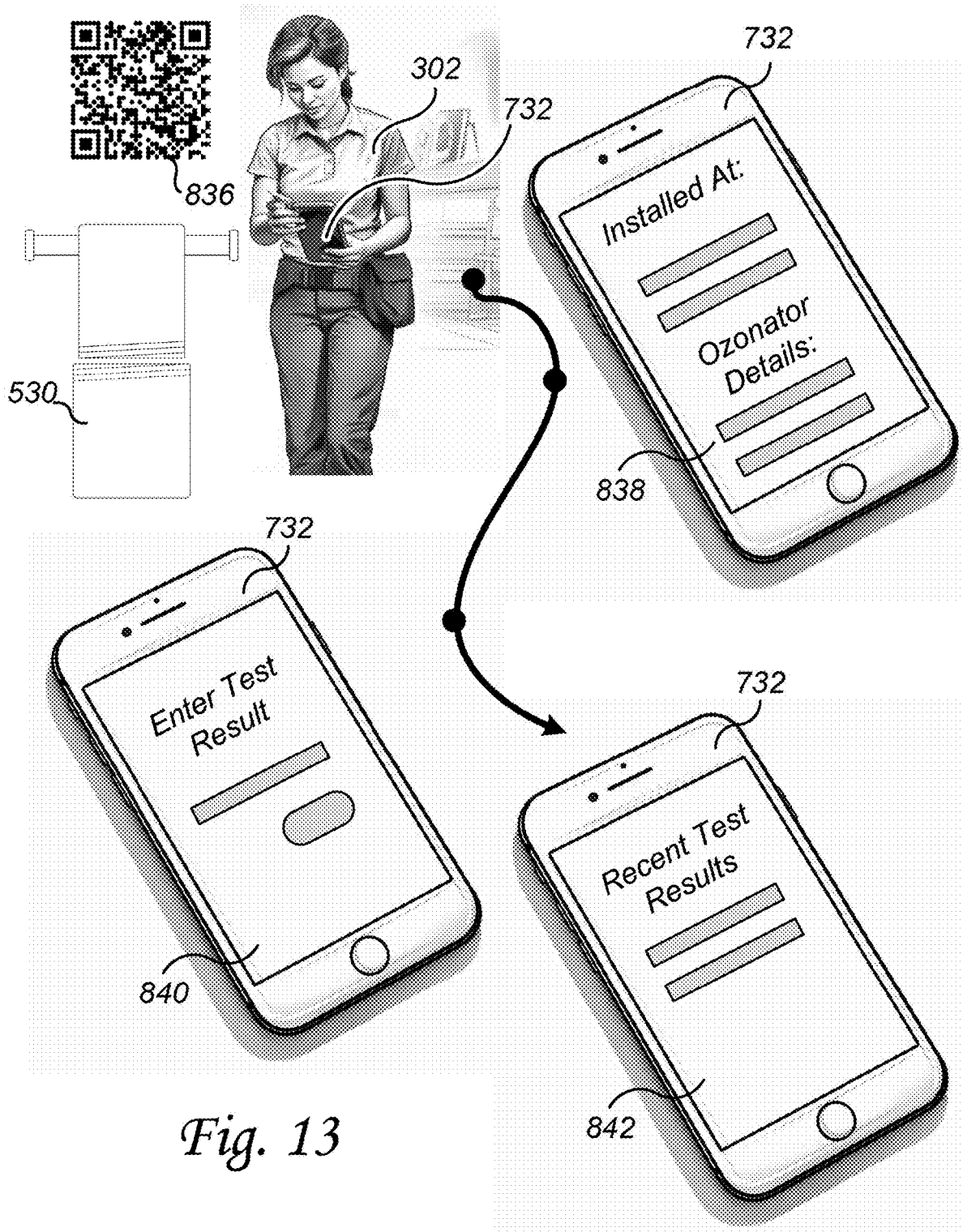
FIG. 13 illustrates one example of a technician's use of a software application.

In an exemplary embodiment and with reference to at least FIG. 13, a computing device 732, operated by technician 302, data communicates the test ozone concentration to a remote data processing resource 702, and receives from the remote data processing resource 702, by way of the computing device 732 a plurality of aqueous ozone generator service life data that corresponds to the remaining service life 826 of the electrochemical generator 516.

In an exemplary embodiment, in operation, technician 302 can scan a QR code 836 or other suitable identifier to identify the specific aqueous ozone disinfection system 100.

In screenshot 832, the specific aqueous ozone disinfection system 100 identification can be data communicated to the remote data processing resource 702 and received in return from the remote data processing resource 702 data related to where the specific aqueous ozone disinfection system 100 is installed, detailed information about the specific aqueous ozone disinfection system 100, and other relevant information, as may be required and/or desired in a particular embodiment.

In screenshot 840, technician 302 can enter the test ozone concentration reading just taken and data communicate the test ozone concentration reading to the remote data processing resource 702 where the test ozone concentration reading can be recorded.

In screenshot 842, received from the remote data processing resource is a plurality of aqueous ozone generator service life data related to specific aqueous ozone disinfection system 100. Such plurality of aqueous ozone generator service life data can comprise prior test results (time/date, ozone concentration, other data), the technicians who made those prior readings, an estimation of the remaining service life 826, maintenance information, service information, warning or alerts, and other relevant information, as may be required and/or desired in a particular embodiment.

In an exemplary embodiment, technician 302 can use an ozone sensor that is attached either temporarily or permanently to the control system 500. In this regard, in operation, a control system 500 can comprise a microcontroller 504, a memory 504, an ozone sensor 522 (attached temporarily to make a reading or permanently where test ozone readings can be initiated automatically and/or remotely), and a communication interface 508. The microcontroller 502 is operationally related to the memory 504, the ozone sensor 522, and the communication interface 508.

The memory 504 can be encoded with instructions that when executed by the microcontroller 502 perform the steps of recording, by way of the ozone sensor 522, a test ozone concentration of the ozonated concentrate liquid. By way of the communication interface, the test ozone concentration can be data communicated to a remote data processing resource 702. Confirmation of the recording of the test result by the remote data processing resource 702 can be the receiving, by way of the communication interface 508 of a plurality of aqueous ozone generator service life data. Such plurality of aqueous ozone generator service life data can comprise prior test results (time/date, ozone concentration, other data), the technicians who made those prior readings, an estimation of the remaining service life 826, maintenance information, service information, warning or alerts, and other relevant information, as may be required and/or desired in a particular embodiment.

In an exemplary embodiment, a fixed-volume inspection chamber 136 can receive a continuous flow and maintain a fixed-volume portion 222 of the ozonated concentrate liquid 118. The amount of the fixed-volume portion 222 can be predetermined by one of the test requirements of an ozone concentration test implement 602/604/606. In operation, the ozone concentration test implements 602/604/606 can include an ozone concentration test strip 604, an ozone concentration test drop 602, an ozone concentration test device 606, or other suitable test implements. The ozone concentration test implements 602/604/606 can be manually used by a technician 302 to determine a test ozone concentration of the ozonated concentrate liquid 118 within the fixed-volume inspection chamber 136 by inserting the ozone concentration test implement 602/604/606 into the fixed-volume inspection chamber 136 and then reading the test ozone concentration of the ozonated concentrate liquid 118.

Continuing, a computing device 732, operated by technician 302, data communicates the test ozone concentration to a remote data processing resource 702, and receives from the remote data processing resource 702, by way of the computing device 732 a plurality of aqueous ozone generator service life data that corresponds to the remaining service life of the electrochemical generator 516.

Referring to FIG. 10, there is illustrated one example of mixing pulse sequence 400 by way of transitioning between pump/valve 528A and 528B activation pulses. The mixer pulse sequence 400 can be represented as a square wave 402/404 that indicated a time period 418 that an electronic pump/valve 528A is energized 'ON' or 'OPEN' 410/412 to control the ozone concentration of the ozonated liquid 118 by controlling the flow rate of the mixture 102/140 through the aqueous ozone generator 530 or in standby 'OFF' or "CLOSED" abating mixture 102/140 flow.

In an exemplary embodiment, the mixing pulse sequence 400 is one or more of the pump/valves 528B being energized and/or otherwise 'OPENED' for a predetermined amount of time to allow electrolyte 140 to be dosed into the water 102. A longer 'OPEN' increases the dosing of electrolyte 140. In operation, the dosing amount of the electrolyte is determined to be the amount needed to modify the conductivity of the mixture (water 102+electrolyte 140) to within the desired conductivity range 430.

In an exemplary embodiment, in reference 'A' 414 initially electronic pump/valve 528A is energized allowing the water source 102 to enter the aqueous ozone generator 530. The mixer pulse sequence 400 then continues in reference 'B' 416 by energizing electronic pump/valve 528B allowing the electrolyte 140 to enter the inlet water stream and enter as a mixture 102/140 into the aqueous ozone generator for a predetermined time period 412.

The mixer pulse sequence 400 repeats as needed. Each mixer pulse sequence 400 ratiometrically blends the water source 102 and the electrolyte 140 as well as controls the dwell time of the mixture 120/140 within the aqueous ozone generator 530.

In an exemplary embodiment, a pressure equalization pause 406 can be inserted between transition signals 402/404. In this regard, each time a pump/valve 528A-B is turned 'OFF' or 'CLOSED' a pressure equalization pause 406 can occur before turning the next pump/valve 528A-B 'ON' or 'OPENING'. This pressure equalization pause 406 allows pressures in the coupled lines to the pump/valve 528A-B and system, in general, to stabilize so that when the next pump/valve 528A-B is turned 'ON' or 'OPENED' the pressure is the same as prior sequence cycle and the flow during the timing sequence is predictable and accurate each sequence cycle for the water 120, electrolyte 140, mixture 102/140, and the ozonated concentrate liquid 118 being passed into and through the system 100.

In another exemplary embodiment, the memory 504 can be encoded with instructions that when executed by the microcontroller 502 perform the steps of mixing the water 102 and electrolyte 140 in the predetermined mixture by transitioning between activating the pump 528A for a mixture dwell time pulse 402 width period 410, allowing the mixture 102/140 to flow into/through the aqueous ozone generator 530 during the pulse 402 width period 410. And, activating the electrolyte pump 532B for a pulse 404 width period 412, dosing the water 102 with a predetermined amount of electrolyte 140 during the pulse width 404 period 412. In operation, the pulse 402 width period 410 and the pulse 404 width period 412 are selected to produce a mixture 102/140 at a predetermined desired conductivity range and to control the flow (establishing a desired dwell time for the mixture 102/140 within the aqueous ozone generator in a continuous flow manner) of the mixture 102/140 to a generate a predetermined desired ozone PPM range.

Referring to FIG. 11, there is illustrated one example of a system and network diagram. In an exemplary embodiment, users of the platform and network can include technicians 302, administrators 304, or other authorized persons.

Each of the users uses computing devices 732A-C to data communicate over a global communication network 700 with one or more data processing resources 702. The computing devices 732A-C can be laptop computers, desktop computers, smartphones, tablets, or other types and kinds of computing devices, as may be required and/or desired in a particular embodiment. For disclosure purposes, computing devices 732A-C can be referred to as computing devices 732. Additionally, laptop and desktop types of computing devices 732 can be referred to as computing devices 712C, computing devices 732 such as smartphones can be referred to as computing devices 732B, and computing devices 732 such as tablets can be referred to as computing devices 732A. In operation, any of the users can use any of the types of computing devices 732A-C, without limitation to the type or kind of computing device 732, as may be required and/or desired in a particular embodiment. The global communication network 700 can be the Internet.

The computing devices 732 can comprise a microprocessor 704B/704C, a database 706B/706C, memory 208C, a communication interface 710B/710C, a display 712B/712C, and a plurality of general-purpose inputs and outputs (GPIO) 714B/714C.

Additionally, mobile type of computing device 732A/732B (tablets, smartphones, and others) can comprise a global positioning system (GPS) 716, and a microphone and/or camera 718.

In general, computing devices 232 can be configured with other functions and features, as may be required and/or desired in a particular embodiment.

In an exemplary embodiment, the microprocessor 704B is operationally related to database 706B, memory 708B, communication interface 710B, display 712B, and GPIO 714B In an exemplary embodiment, the microprocessor 704C is operationally related to database 706C, memory 708C, communication interface 710C, display 712C, GPIO 714C, and if equipped with GPS 716, and microphone and/or camera 718. The computing devices 732 each rely on a suitable power source 720B/720C which can include a rechargeable battery, external power supply, or other types and/or kinds of power sources.

Microprocessor 704B/704C can be INTEL, ZILOG, MICROCHIP, AMD, ARM, and/or other types or kinds of microprocessors.

Database 706B/706C can be SQL, MYSQL, MARIADB, ORACLE, MS ACCESS, network-accessible storage, flat files, a combination thereof, or other types and kinds of databases.

Memory 708B/708C can be a combination of RAM, ROM, flash, hard drives, solid-state drives, USB flash drives, micro-SD cards, or other types of removable memory, and/or other types and kinds of memory.

The communication interfaces 710B/710C can be LAN, WAN, USB, Ethernet, RS232, RS485, serial, Wi-Fi, 802.11abgn and similar, 2G 3G 4G 5G compatible, Bluetooth, TCP, UDP, Mesh Network, Zigbee, Pico Network, LORAN, and/or other types and kinds of communication interfaces and protocols.

Display 712B/712C can be a liquid crystal display (LCD), light emitting diode (LED), organic light emitting diode (OLED), or other types and kinds of displays.

The general-purpose inputs and outputs (GPIO) 714B/714C can be TTL, CMOS, MOSFET, transistors, buffers, relays, pushbuttons, switches, and/or other types and kinds of GPIO circuits. In an exemplary embodiment, some of the GPIO 214 lines can be used to drive a touch screen input, biometric input devices, keyboards, and/or types and kinds of computing device input devices.

Global positioning system (GPS) device 716 can be used to determine the geographic location of technician 302 and others who are carrying a computing device 732 equipped with a GPS 716. In this regard, such computing devices 732 are typically mobile computing devices such as tablets 732A, smartphones 732B, and other similar types and/or kinds of mobile computing devices 732.

Microphone and/or camera 718 can be used to record audio, and video, and take pictures. In this regard, users 304/306 can use their computing devices equipped with a microphone and/or camera 718 to make digital media records that can be selectively shared as appropriate including on social media and other digital media outlet locations.

With reference to FIG. 11, the data processing resource 702 can be a server, network storage device, or other types and kinds of data processing resources. Such data processing resources can be AMAZON WEB SERVICES (AWS), MICROSOFT AZURE, or other types and kinds of hosted data processing resource services. For disclosure purposes, a remote data processing resource 702 can also be referred to as server 702.

The data processing resource 702 can comprise a microprocessor 704A, a database 706A, memory 708A, and a communication interface 710A. The microprocessor 704A is operationally related to database 706A, memory 708A, and communication interface 710A.

The microprocessor 704A can be INTEL, ZILOG, MICROCHIP, AMD, ARM, and/or other types or kinds of microprocessors.

The database 706A can be SQL, MYSQL, MARIADB, ORACLE, MS ACCESS, network accessible storage, flat files, a combination thereof, or other types and kinds of databases.

The memory 708A can be a combination of RAM, ROM, flash, hard drives, solid-state drives, USB flash drives, micro-SD cards, or other types of removable memory, and/or other types and kinds of memory.

The communication interfaces 710A can be LAN, WAN, USB, Ethernet, RS232, RS485, serial, Wi-Fi, 802.11abgn and similar, 2G 3G 4G 5G compatible, Bluetooth, TCP, UDP, Mesh Network, Zigbee, Pico Network, LORAN, and/or other types and kinds of communication interfaces and protocols.

Figure 12:
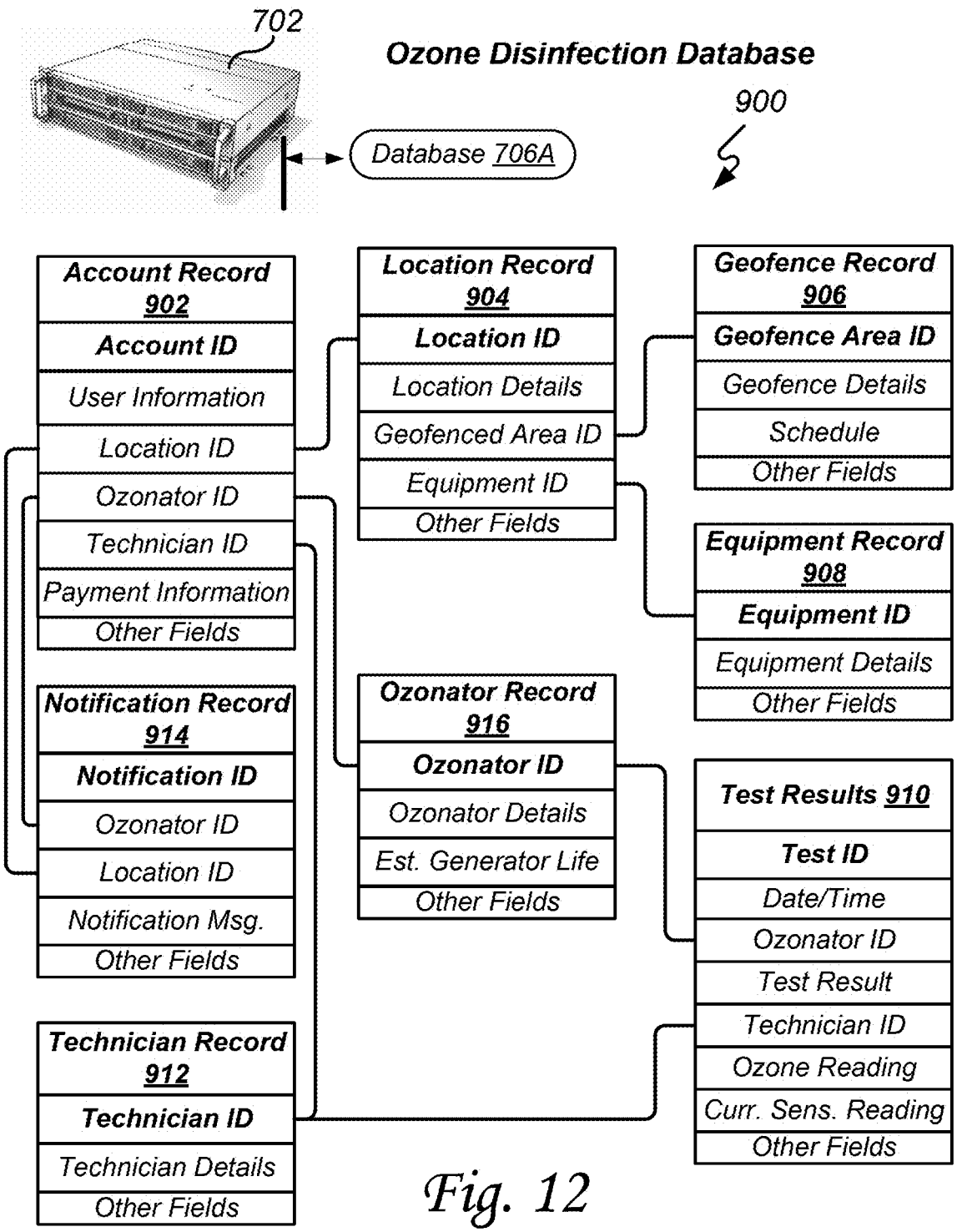
FIG. 12 illustrates one example of an ozone disinfection database structure.

Referring to FIG. 12, there is illustrated one example of an ozone disinfection database structure 900. In an exemplary embodiment, at least one database 706A/706B/706C can be implemented on at least one of the data processing resources 702 also referred to as server 702, or computing devices 732. In operation, one or more databases 706A/706B/706C can be accessed/created/managed/maintained as appropriate by more than one stakeholder. In this regard, in addition to system administrators and other authorized persons, other stakeholders can access/create/manage/maintain as appropriate.

In an exemplary embodiment, such databases 706A/706B/706C can be SQL, MYSQL, MARIADB, ORACLE, MS ACCESS, network-accessible storage, flat files, a combination thereof, or other types and kinds of databases.

In an exemplary embodiment, the ozone disinfection database 900 can reside on a remote data processing resource 702 in database 706A. In this regard, the ozone disinfection database 900 can comprise a series of tables, records, fields, and accounts that include account record 902, location record 904, geofence record 906, equipment record 908, test results 910, technician record 912, notification record 914, ozonator record 916, and/or other types or kinds of records as may be required and/or desired in a particular embodiment. The database structure illustrated in FIG. 12 also illustrates the relationship between the various tables.

In an exemplary embodiment, the data structure of account record 902 is illustrative and can be expanded and modified without particular limitation as needed and as appropriate to support the functionality and methods of the present invention and to support future functionality and methods of the present invention as it grows and evolves over time.

Figure 14:
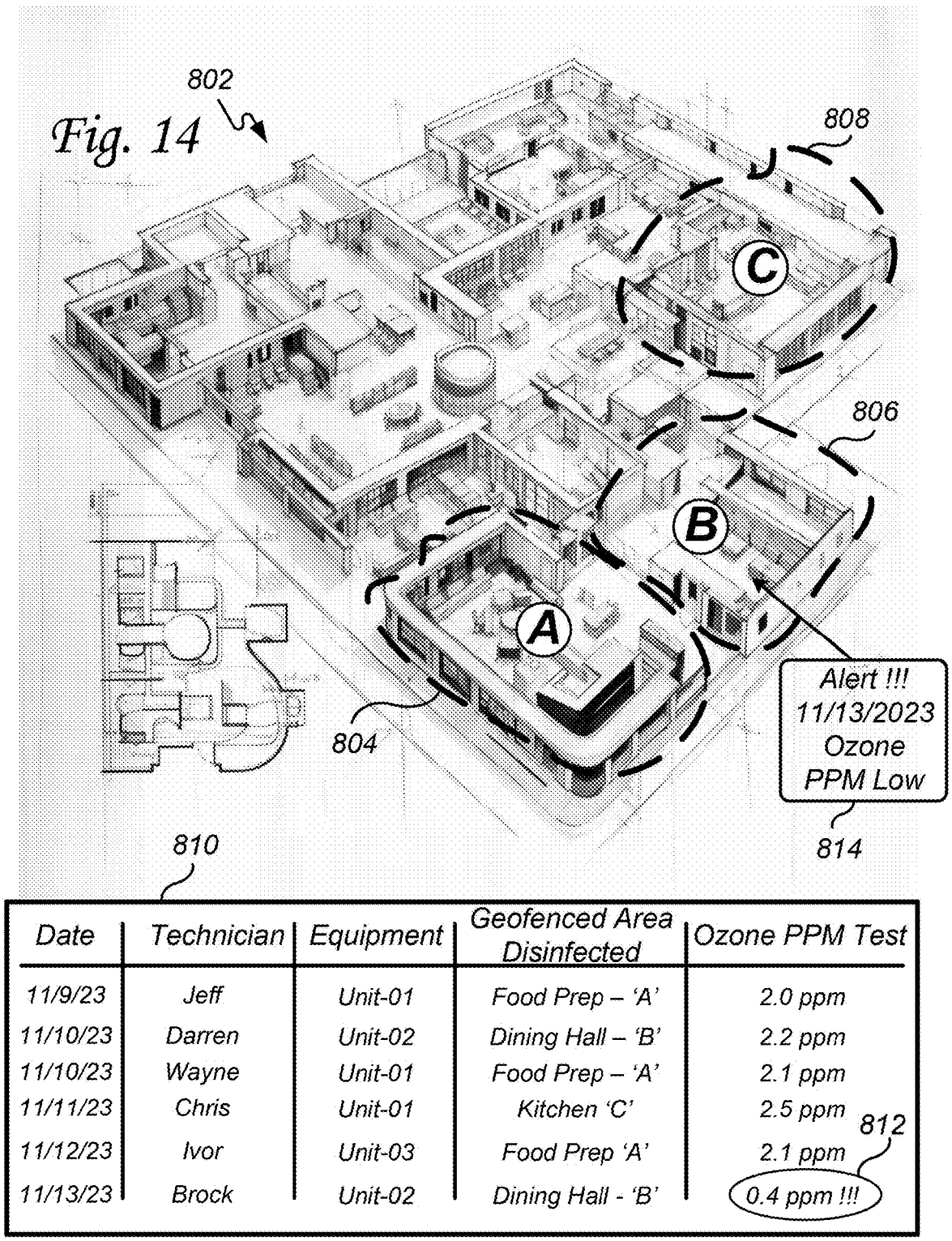
FIG. 14 illustrates one example of a floor plan to monitor geofenced areas that have been treated with the concentrated ozone liquid.

Referring to FIG. 14, there is illustrated one example of a floor plan 802 to monitor geofenced food wash areas and food preparation areas 804/806/808 that are services by a specific aqueous ozone generator 530. In an exemplary embodiment, by way of a global position system (GPS), 514 geofence areas 804/806/808 can be established around where the aqueous ozone generator 530 services and can be recorded. By way of the communication interface 508, the status of the aqueous ozone generator and thus the food wash and food preparation areas services by the aqueous ozone generator 530 can be monitored including the GPS location 804/806/808. This information can be data communicated to a remote data processing resource 702. In operation, the aqueous ozone generator 530, food wash, and food preparation surfaces 204 that are being treated can be remotely monitored.

Additionally, in an exemplary embodiment, alerts 812/814 can be generated when for example the aqueous ozone generator 530 and thus the food wash and/or food preparation surface are not being treated with a sufficiently high enough concentration of ozone to achieve adequate disinfection, or for other reasons as may be required and/or desired in a particular embodiment. Such alerts 812/814 can also be noted on reports 810.

In another exemplary embodiment, reports 810 can be generated to monitor, track, and summarize activities. Such reports 810 can include a plurality of aqueous ozone generator service life data, ozone concentration test results, geofenced surfaces 804/806/808 description, location, disinfection history, and other data as may be required and/or desired in a particular embodiment.

Referring to FIG. 15, there is illustrated one example of monitoring ozone concentration test results. In an exemplary embodiment in reference 'A', test ozone concentration of the ozonated concentrate liquid 118 can be generated by way of a plurality of ozone concentration test implement that include ozone concentration test strips 604, ozone concentration test drops 602, ozone concentration test device 606, and ozone sensor 520.

In reference 'B', such ozone concentration test results 816 can be recorded on a remote data processing resource and used to generate reports 818 such reports can be tailored as needed and can be referred to as a plurality of aqueous ozone generator service life data. Such plurality of aqueous ozone generator service life data can comprise prior test results (time/date, ozone concentration, other data), the technicians who made those prior readings, an estimation of the remaining service life 826, maintenance information, service information, warning or alerts, and other relevant information, as may be required and/or desired in a particular embodiment.

An advantage, in the present invention, and with reference to 'C', is that by tracking ozone concentration 822 test results over time 824 the remaining service life 826 also referred to as the service life status of the electrochemical generator 516 and/or the aqueous ozone generator 530 can be determined or otherwise predicted. In this regard, components and materials within the electrochemical generator 516 and/or the aqueous ozone generator 530 degrade over time under normal use. A metric that changes as the efficiency of the electrochemical generator 516 and/or the aqueous ozone generator 530 degrade can be the amount of ozone produced and thus changes in ozone concentrations ppm can be observed over time. This present invention can establish a range 828 where ozone concentration test results above 832 are considered acceptable and ozone concentration test results 820 are below 834 are considered unacceptable. Appropriate electrochemical generator 516 and/or the aqueous ozone generator 530 replacement notifications 830 can be sent to technician 302 and/or the administrator. Such replacement notification can inform technician 302, and/or administrator 304 that the electrochemical generator 516 and/or the aqueous ozone generator 530 need to be serviced or replaced.

In the case that the ozone concentration test results indicated premature degradation of the electrochemical generator 516 and/or the aqueous ozone generator 530 before a normal life expectance, technician 302 and/or administrator 304 can be notified to check for water mineral scaling of the electrochemical generator 516 and/or the aqueous ozone generator 530 components and clean as appropriate. The ability of the present invention to detect mineral scaling which is cleanable can save the technician 302 and/or the administrator the cost of prematurely replacing the electrochemical generator 516 and/or the aqueous ozone generator 530.

In an exemplary embodiment, in operation, the service life status of the electrochemical generator 516 and/or the aqueous ozone generator 530 can be displayed on display 506/712B/712C. The service life status is based on the plurality of aqueous ozone generator service life data received from the remote data processing resource 702.

In an exemplary embodiment, in cases where the ozone concentration test results 826 are out of range 828 and/or are below 834 which is considered unacceptable, the system can be prevented from operating. In other words, if the plurality of aqueous ozone generator service life data indicates the aqueous ozone generator has reached the end of service life the system can be prevented from working until the electrochemical generator 516 and/or aqueous ozone generator 530 is serviced or replaced.

Figure 16:
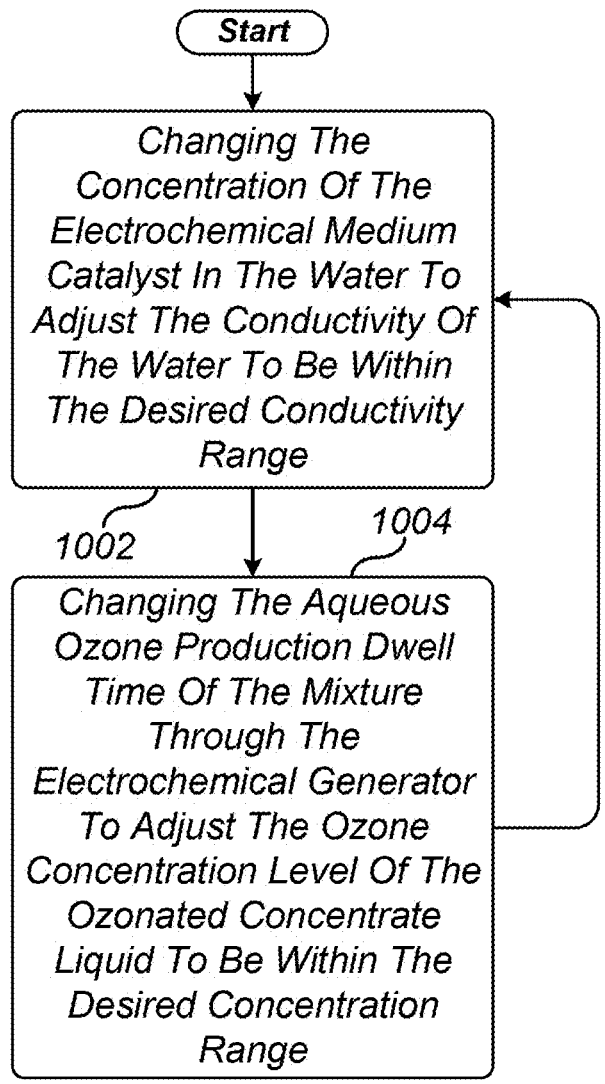
FIG. 16 illustrates one example of a method of using an aqueous ozone disinfection system.

Referring to FIG. 16, there is illustrated one example of a method of using an aqueous ozone disinfection system 100. In an exemplary embodiment, in step 1002, the method begins by changing the concentration of the electrochemical medium catalyst in the water to adjust the conductivity of the water 102 to be within the desired conductivity range 430. In this regard, water that is soft or otherwise has a below-desired conductivity can be adjusted by adding electrolyte 140 to the water 102 to improve the conductivity to within the desired conductivity range 430. Such adjustments improve or other maintain the desired electrochemical production of aqueous ozone molecules. The method then moves to step 1004.

In step 1004, the method continues by changing the aqueous ozone production dwell time 442 of the mixture through the electrochemical generator 516 to adjust the ozone concentration level of the ozonated concentrate liquid 118 to be within the desired ozone concentration range 440.

Figures 25, 26:
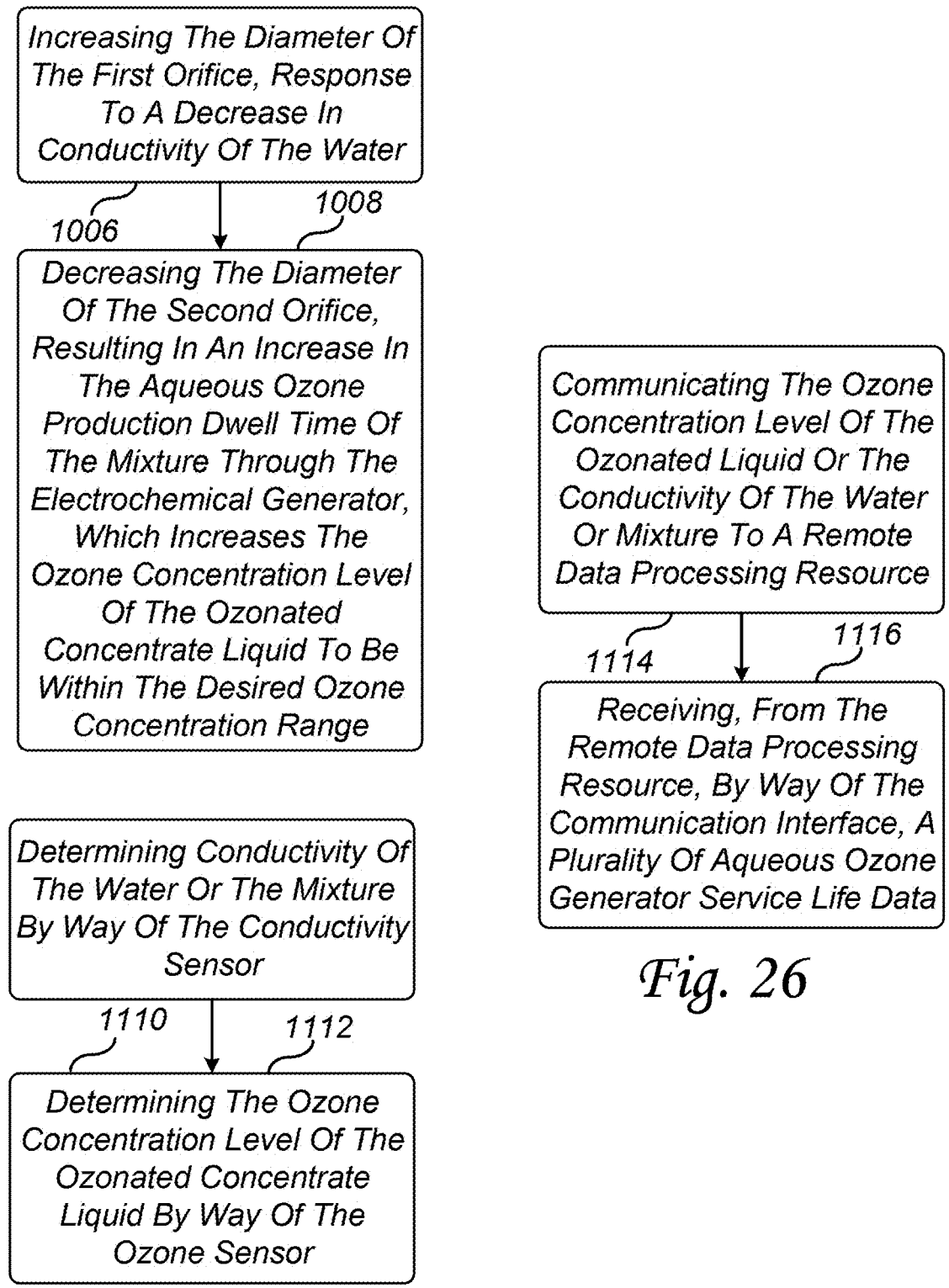

Referring to FIGS. 25-28, there are illustrated exemplary embodiments that can be interchangeably used with the methods of the present invention. With reference to FIG. 26, in an exemplary embodiment, in step 1006, the diameter of the first orifice which controls the amount of electrolyte 140 added to the water 102 can be increased, by way of the first orifice control, responsive to a decrease in the conductivity of the water 102, resulting in an increase in conductivity (lower resistance, electrical current flow more easily between the electrodes) of the water 102 to within the desired conductivity range 430. The method then moves to step 1008.

In step 1008, the diameter of the second orifice is decreased (slowing the flow of the mixture 102/140), by way of the second orifice control, resulting in an increase in the aqueous ozone production dwell time 442 of the mixture through the electrochemical generator 516, which increases the ozone concentration level of the ozonated concentrate liquid to be within the desired ozone concentration range 440.

In step 1010, the conductivity of the water 102 or the mixture 102/140 is determined by way of the conductivity sensor 532. The method then moves to step 1012.

In step 1012, the ozone concentration level of the ozonated concentrate liquid 118 is determined by way of the ozone sensor 522.

With reference to FIG. 26, in step 1014, the ozone concentration level of the ozonated concentrate liquid 118 or conductivity of the water 102 or the mixture 102/140 is data communicated, by way of the communication interface 508, to a remote data processing resource 702. The method then moves to step 1016.

In step 1016, a plurality of aqueous ozone generator service life data is received, from the remote data processing resource 702, by way of the communication interface 508.

Figure 27:
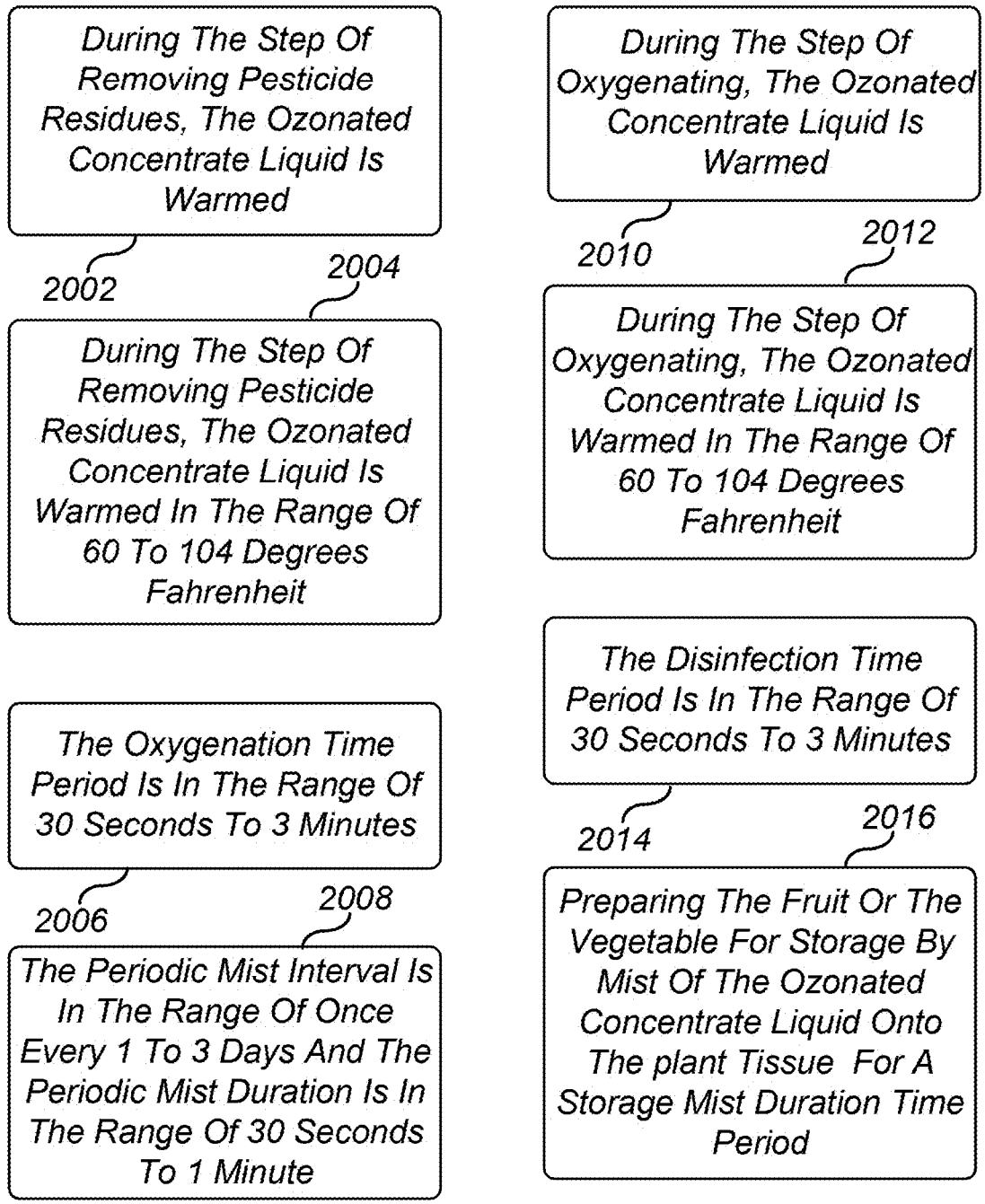

With reference to FIG. 27, in step 2002, during the step of removing pesticide residues, the ozonated concentrate liquid 118 is warmed, and in step 2004 the ozonated concentrate liquid 118 is warmed in the range of 60 to 104 degrees Fahrenheit. In operation, pesticide residue removal is enhanced, and harm to produce 318 which includes lettuce 318 is minimized.

An advantage, in the present invention, is that how warming the ozonated concentrate liquid 118 improves the efficacy in pesticide removal. Here are a few ways in which warming ozonated water may improve its efficacy:

Increased solubility: Warmer water generally has a higher solubility for gases, including ozone. This means that warmer water can dissolve more ozone, leading to a higher concentration of ozone in the water. A higher concentration of ozone results in more effective pesticide breakdown;

Enhanced chemical reactions: Temperature can influence chemical reactions, and warmer water facilitates the chemical reactions involved in the breakdown of pesticides by ozone. The increased kinetic energy of molecules at higher temperatures accelerates reaction rates; and Improved penetration: Warmer water improves the penetration of ozone into the porous surfaces of fruits and vegetables. Pesticide residues can be present not only on the surface but also within the produce. Improved penetration of ozonated water helps in reaching and breaking down residues that are more deeply embedded.

In step 2010, during the step of oxygenating, the ozonated concentrate liquid 118 is warmed, and in step 2012 the ozonated concentrate liquid 118 is warmed in the range of 60 to 104 degrees Fahrenheit. In operation, oxygenation of the plant tissue 326 is enhanced, and harm to the produce 318 which includes the lettuce 318 is minimized. Furthermore, in step 2006, the oxygenation treatment time 472 can be in the range of 30 seconds to 3 minutes, or other suitable time.

In step 2014, the disinfection treatment time 470 can be in the range of 30 seconds to 3 minutes, or other suitable time.

In step 2008, the periodic mist interval 474 can be in the range of once every 1 to 3 days and the periodic mist duration is in the range of 30 seconds to 1 minute, or other suitable times.

In step 2016, the produce 318 which includes the lettuce 318 can be prepared for storage by misting the ozonated concentrate liquid 118 onto the plant tissue 326 for a storage mist duration treatment time. Such storage mist duration treatment time can be in the range of less than one minute.

With reference to FIG. 28, in step 2102, the produce 318 which includes the lettuce 318 can be dried by air drying, salad spinning, blotting with a paper/cloth towel or clean kitchen towel, commercial salad dryers, a draining rack, or other suitable methods.

In step 2104, produce 318 which includes lettuce 318 can be spun dry prior to the step of returning the lettuce to the prepackaged lettuce packaging for storage.

In step 2106, the food item 328 can be a sandwich, a salad, a hamburger, a pizza, a taco, a burrito, or other type or kind of food item as may be required and/or desired in a particular embodiment.

In step 2108, pesticide residues can be removed from the fruit or the vegetable 318 by a rinse with the ozonated concentrate liquid for a pesticide residue removal treatment time 468. The ozonated concentrate liquid 118 used in the rinse is preferably not reused in other steps.

In step 2110, the produce 318 which includes the lettuce 318 can be removed from a prepackaged lettuce packaging 324, prior to the step of removing pesticide residues. And, in step 2112 the produce 318 which includes the lettuce 318 can be returned to the prepackaged lettuce packaging 324 for storage after the steps of removing, disinfecting, and oxygenating.

In step 2114, the plant tissue 326 can be oxygenated by removing the fruit or the vegetable from the immersion and delaying drying for an oxygenation treatment time 472, enhancing the metabolic processes of the plant tissue 326.

In step 2116, a customer 310 accessible one or more countertop 316 or one or more table 316 can be disinfected by misting the ozonated concentrate liquid 118 onto the surface of the countertop 316 or the table 316 and allowed to air drying absent agitation or removal, for at least a customer used surface treatment time. The customer-used surface treatment time can be in the range of less than one minute, or other suitable ranges.

The capabilities of the present invention can be implemented in software, firmware, hardware, or some combination thereof.

As one example, one or more aspects of the present invention can be included in an article of manufacture (e.g., one or more computer program products) having, for instance, computer-usable media. The media has embodied therein, for instance, computer-readable program code means for providing and facilitating the capabilities of the present invention. The article of manufacture can be included as a part of a computer system or sold separately.

Additionally, at least one program storage device readable by a machine, tangibly embodying at least one program of instructions executable by the machine to perform the capabilities of the present invention can be provided.

The flow diagrams depicted herein are just examples. There may be many variations to these diagrams or the steps (or operations) described therein without departing from the spirit of the invention. For instance, the steps may be performed in a differing order, or steps may be added, deleted, or modified. All of these variations are considered a part of the claimed invention.

While the preferred embodiment of the invention has been described, it will be understood that those skilled in the art, both now and in the future, may make various improvements and enhancements which fall within the scope of the claims which follow. These claims should be construed to maintain the proper protection for the invention first described.

What is claimed is:

1. A post-harvest lettuce treatment method using aqueous ozone to disinfect, extend vitality, and reduce the amount of lettuce needed during the preparation of a food item, the post-harvest lettuce treatment method comprising the steps of:
    creating an ozonated concentrate liquid by way of an aqueous ozone generator, the aqueous ozone generator receives a water source and generates from the water source the ozonated concentrate liquid;
    removing pesticide residues from one or more of a lettuce by a rinse with the ozonated concentrate liquid for a pesticide residue removal treatment time, the ozonated concentrate liquid used in the rinse is not reused;
    disinfecting the lettuce by an immersion in the ozonated concentrate liquid for a disinfection treatment time, the lettuce comprises a plant tissue;
    oxygenating the plant tissue by removing the lettuce from the immersion and delaying drying for an oxygenation treatment time, enhancing metabolic processes of the plant tissue, and increasing the size of the cells of the plant tissue and correspondingly the lettuce which reduces the amount of the lettuce needed in the preparation of the food item;
    neutralizing odor of the plant tissue by misting the ozonated concentrate liquid onto the plant tissue, at a periodic mist interval and for each of the periodic mist interval, a mist duration treatment time; and
    returning to the step of neutralizing at the periodic mist interval until the lettuce is utilized in the preparation of the food item.

2. The post-harvest lettuce treatment method in accordance with claim 1, the aqueous ozone generator comprises:
    an electrochemical generator, the electrochemical generator comprises an ion exchange material, the electrochemical generator receives the water source and an electrolyte forming a mixture, and generates from the mixture the ozonated concentrate liquid;
    an electrochemical medium catalyst governor regulates the amount of the electrochemical medium catalyst in the water, controlling the conductivity of the water, within a desired conductivity range; and
    a flow governor regulates an aqueous ozone production dwell time of the mixture through the electrochemical generator, controlling an ozone concentration level of the ozonated concentrate liquid within a desired ozone concentration range.

3. The post-harvest lettuce treatment method in accordance with claim 2, the electrochemical medium catalyst is an electrolyte.

4. The post-harvest lettuce treatment method in accordance with claim 3, the electrolyte is potassium bicarbonate KHCO3.

5. The post-harvest lettuce treatment method in accordance with claim 1, during the step of removing pesticide residues, the ozonated concentrate liquid is warmed in the range of 60 to 104 degrees Fahrenheit, wherein pesticide residue removal is enhanced and harm to the lettuce is minimized.

6. The post-harvest lettuce treatment method in accordance with claim 1, the oxygenation treatment time is in the range of 30 seconds to 3 minutes.

7. The post-harvest lettuce treatment method in accordance with claim 4, during the step of oxygenating, the ozonated concentrate liquid is warmed in the range of 60 to 104 degrees Fahrenheit, wherein oxygenation of the plant tissue is enhanced and harm to the lettuce is minimized.

8. The post-harvest lettuce treatment method in accordance with claim 1, the disinfection treatment time is in the range of 30 seconds to 3 minutes.

9. The post-harvest lettuce treatment method in accordance with claim 1, the periodic mist interval is in the range of once every 1 to 3 days and the periodic mist duration is in the range of 30 seconds to 1 minute.

10. The post-harvest lettuce treatment method in accordance with claim 1, further comprising the step of:
preparing the lettuce for storage by misting the ozonated concentrate liquid for a storage mist duration treatment time.

11. The post-harvest lettuce treatment method in accordance with claim 1, further comprising the step of:
drying the lettuce by air drying, salad spinning, blotting with paper towel or clean kitchen towel, commercial salad dryers, or a draining rack.

12. The post-harvest lettuce treatment method in accordance with claim 1, further comprising the step of:
removing the lettuce from a prepackaged lettuce packaging, prior to the step of removing pesticide residues; and
returning the lettuce to the prepackaged lettuce packaging for storage after the steps of removing, disinfecting, and oxygenating.

13. The post-harvest lettuce treatment method in accordance with claim 1, the food item is a sandwich, a salad, a hamburger, a pizza, a taco, or a burrito.

14. A post-harvest lettuce treatment method using aqueous ozone to disinfect, extend vitality, and reduce the amount of lettuce needed during the preparation of a food item, the post-harvest lettuce treatment method comprising the steps of:
creating an ozonated concentrate liquid by way of an aqueous ozone generator, the aqueous ozone generator receives a water source and generates from the water source the ozonated concentrate liquid;
removing one or more of a lettuce from a prepackaged lettuce packaging;
removing pesticide residues from the lettuce by a rinse with the ozonated concentrate liquid for a pesticide residue removal treatment time;
disinfecting the lettuce by an immersion in the ozonated concentrate liquid for a disinfection treatment time, the lettuce comprises a plant tissue;
oxygenating the plant tissue by removing the lettuce from the immersion and delaying drying for an oxygenation treatment time, enhancing metabolic processes of the plant tissue, and increasing size of the cells of the plant tissue which reduces the amount of the lettuce needed in the preparation of the food item; and
returning the lettuce to the prepackaged lettuce packaging for storage until the lettuce is utilized in the preparation of the food item.

15. The post-harvest lettuce treatment method in accordance with claim 14, the aqueous ozone generator comprises:
an electrochemical generator, the electrochemical generator comprises an ion exchange material, the electrochemical generator receives the water source and an electrolyte forming a mixture, and generates from the mixture the ozonated concentrate liquid;
an electrochemical medium catalyst governor regulates the amount of the electrochemical medium catalyst in the water, controlling the conductivity of the water, within a desired conductivity range; and
a flow governor regulates an aqueous ozone production dwell time of the mixture through the electrochemical generator, controlling an ozone concentration level of the ozonated concentrate liquid within a desired ozone concentration range.

16. The post-harvest lettuce treatment method in accordance with claim 15, the electrochemical medium catalyst is an electrolyte.

17. The post-harvest lettuce treatment method in accordance with claim 14, during the step of removing pesticide residues, the ozonated concentrate liquid is warmed in the range of 60 to 104 degrees Fahrenheit, wherein pesticide residue removal is enhanced and harm to the lettuce is avoided, and the oxygenation treatment time is in the range of 30 seconds to 3 minutes.

18. The post-harvest lettuce treatment method in accordance with claim 14, during the step of oxygenating, the ozonated concentrate liquid is warmed in the range of 60 to 104 degrees Fahrenheit, wherein oxygenation of the plant tissue is enhanced and harm to the lettuce is avoided, and the disinfection treatment time is in the range of 30 seconds to 3 minutes.

19. The post-harvest lettuce treatment method in accordance with claim 14, further comprising the step of:
spinning the lettuce dry prior to the step of returning the lettuce to the prepackaged lettuce packaging for storage.

20. A post-harvest lettuce treatment method using aqueous ozone to disinfect, extend vitality, and reduce the amount of lettuce needed during the preparation of a food item, the post-harvest lettuce treatment method comprising the steps of:
creating an ozonated concentrate liquid by way of an aqueous ozone generator, the aqueous ozone generator receives a water source and generates from the water source the ozonated concentrate liquid;
removing pesticide residues from one or more of a lettuce by a rinse with the ozonated concentrate liquid, for a pesticide residue removal treatment time;
disinfecting the lettuce by an immersion in the ozonated concentrate liquid for a disinfection treatment time, the lettuce comprises a plant tissue;
oxygenating the plant tissue by removing the lettuce from the immersion and delaying drying for an oxygenation treatment time, enhancing metabolic processes of the plant tissue and increasing size of the cells of the plant tissue which reduces the amount of the lettuce needed in the preparation of the food item; and
neutralizing odor of the plant tissue by misting the ozonated concentrate liquid onto the food item including the plant tissue prior to serving the food item which comprises the lettuce to a consumer.

21. A post-harvest lettuce treatment method using aqueous ozone to disinfect, extend vitality, and reduce the amount of lettuce needed during the preparation of a food item, the post-harvest lettuce treatment method comprising the steps of:
creating an ozonated concentrate liquid by way of an aqueous ozone generator, the aqueous ozone generator receives a water source and generates from the water source the ozonated concentrate liquid;
disinfecting one or more of a lettuce by filling a prepackaged produce packaging, which comprises the lettuce, with the ozonated concentrate liquid, immersing the lettuce in the ozonated concentrate liquid for a disinfection treatment time, each of the lettuce comprises a plant tissue;

oxygenating the plant tissue by draining the prepackaged produce packaging and delaying before drying the lettuce for an oxygenation treatment time, enhancing metabolic processes of the plant tissue;

neutralizing odor of the plant tissue by misting the ozonated concentrate liquid onto the plant tissue, at a periodic mist interval and for each of the periodic mist interval, a mist duration treatment time; and returning to the step of neutralizing at the periodic mist interval until the lettuce is utilized in the preparation of the food item.

* * * * *